(12) United States Patent
Hammond et al.

(10) Patent No.: US 9,637,750 B2
(45) Date of Patent: May 2, 2017

(54) P5SM SUICIDE EXON FOR REGULATING GENE EXPRESSION

(71) Applicant: THE REGENTS OF THE UNIVERSITY OF CALIFORNIA, Oakland, CA (US)

(72) Inventors: Ming Chen Hammond, Berkeley, CA (US); Alexander J. Westermann, Wuerzburg (DE); Qian Qin, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 872 days.

(21) Appl. No.: 13/747,395

(22) Filed: Jan. 22, 2013

(65) Prior Publication Data

US 2013/0291226 A1 Oct. 31, 2013

Related U.S. Application Data

(60) Provisional application No. 61/589,812, filed on Jan. 23, 2012.

(51) Int. Cl.
*C12N 15/82* (2006.01)
*A01H 5/10* (2006.01)

(52) U.S. Cl.
CPC ..... *C12N 15/8217* (2013.01); *C12N 15/8216* (2013.01); *C12N 15/8237* (2013.01); *C12N 15/8238* (2013.01); *C12N 15/8279* (2013.01)

(58) Field of Classification Search
None
See application file for complete search history.

(56) References Cited

U.S. PATENT DOCUMENTS 7,794,931 B2 * 9/2010 Breaker ................ A61K 31/00
435/6.11

OTHER PUBLICATIONS

Hammond et al, 2009, Nature Structural & Molecular Biology, 16:541-548.*
Ali et al., "Regulation of Alternative Splicing of Pre-mRNAs by Stresses", Current Topics in Microbiology and Immunology, vol. 326, 2008, pp. 257-275.
Aoyama et al., "A Glucocorticoid-Mediated Transcriptional induction System in Transgenic Plants", The Plant Journal, vol. 11, Issue 3, Mar. 1997, pp. 605-612.
Bocobza et al., "Riboswitch-Dependent Gene regulation and its evolution in the Plant Kingdom", Genes & Development, vol. 21, No. 22, 2007, pp. 2874-2879.
Campbell et al., "Comprehensive analysis of alternative splicing in rice and comparative analyses with Arabidopsis", BMC Genomics, vol. 7, Dec. 2006, 17 pages.

Chen et al., "Mechanisms of Alternative Splicing Regulation: Insights from Molecular and Genomics Approaches", Nature Reviews Molecular Cell Biology, vol. 10, No. 11, 2009, pp. 741-754.
Cooper et al., "RNA and Disease", Cell, vol. 136, No. 4, Feb. 2009, pp. 777-793.
Cooper, Thomas A., "Use of Minigene Systems to Dissect Alternative Splicing Elements", Methods, vol. 37, Issue 4, Dec. 2005, pp. 331-340.
Croft et al., "Thiamine Biosynthesis in Algae is regulated by Riboswitches", Proceedings of the National Academy of Sciences of the United States of America, vol. 104, No. 52, Dec. 2007, pp. 20770-20775.
Culler et al., "Reprogramming Cellular behavior with RNA Controllers Responsive to Endogenous Proteins", Science, vol. 330, No. 6008, Nov. 2010, pp. 1251-1255.
Egoavil et al., "Structural Analysis of Elements contributing to 5' Splice Site Selection in Plant Pre-mRNA Transcripts", The Plant Journal, vol. 12, No. 5, Nov. 1997, pp. 971-980.
Fu et al., "Alternative Splicing of Anciently Exonized 5S rRNA Regulates Plant Transcription Factor TFIIIA", Genome Research, vol. 19, No. 5, May 2009, pp. 913-921.
Gassmann, W., "Alternative Splicing in Plant Defense", Current Topics in Microbiology and Immunology, vol. 326, 2008, pp. 219-233.
Gusti et al., "Sequestering of the 3' Splice Site in a Theophylline-Responsive Riboswitch Allows Ligand-Dependent Control of Alternative Splicing", Oligonucleotides, vol. 18, Issue 1, Mar. 5, 2008, pp. 93-99.
Halpin, Claire, "Gene Stacking in Transgenic Plants—the Challenge for 21st Century Plant Biotechnology", Plant Biotechnology Journal, vol. 3, Issue 2, Mar. 2005, pp. 141-155.
Hammond et al., "A Plant Plant 5S Ribosomal RNA Mimic Regulates Alternative Splicing of Transcription Factor IIIA Pre-mRNAs", Nature Structural & Molecular Biology, vol. 16, No. 5, May 2009, pp. 541-549.
Hickey et al., "Transgene Regulation in Plants by Alternative Splicing of a Suicide Exon", Nucleic Acids Research, vol. 40, No. 10, 2012, pp. 4701-4710.
Hoefgen et al., "Biochemical and Genetic-Analysis of Different Patatin Isoforms Expressed in Various Organs of Potato (*Solanum-tuberosum*)", Plant Science, vol. 66, No. 2, 1990, pp. 221-230.
Horton et al., "Gene Splicing by Overlap Extension: Tailor-Made Genes using the Polymerase Chain Reaction", BioTechniques, vol. 8, No. 5, 1990, pp. 528-535; reprinted (2013), Biotechniques, 54(3), 129-133.
Kearney et al., "Widespread distribution and fitness contribution of Xanthomonas Campestris Avirulence Gene avrBs2", Nature, vol. 346, No. 6282, Jul. 1990, pp. 385-386.
Kerenyi et al., "Inter-Kingdom Conservation of Mechanism of Nonsense-Mediated mRNA Decay", The EMBO Journal, vol. 27, No. 11, Jun. 2008, pp. 1585-1595.

(Continued)

*Primary Examiner* — Jason Deveau Rosen
(74) *Attorney, Agent, or Firm* — Morrison & Foerster LLP

(57) ABSTRACT

The present disclosure relates to inducible hybrid plant 5S rRNA mimic (P5SM) RNA elements that regulate gene expression by alternative splicing, and to methods of using such RNA elements for regulating transgene expression in eukaryotic host cells and plants.

26 Claims, 20 Drawing Sheets
(15 of 20 Drawing Sheet(s) Filed in Color)

(56) References Cited

OTHER PUBLICATIONS

Kertesz et al., "Both Introns and Long 3'-UTRs Operate as Cis-Acting Elements to trigger Nonsense-Mediated Decay in Plants", Nucleic Acids Research, vol. 34, No. 21, Dec. 2006, pp. 6147-6157.

Kim et al., "Ligand-Induced Sequestering of Branchpoint Sequence allows Conditional Control of Splicing", BMC Molecular Biology, vol. 9, Feb. 12, 2008, 15 pages.

Kojima et al., "Post-Transcriptional Control of Circadian Rhythms", Journal of Cell Science, vol. 124, 2011, pp. 311-320.

Lopez, Javier A., "Alternative Splicing of Pre-mRNA: Developmental Consequences and Mechanisms of Regulation", Annual Review of Genetics, vol. 32, Dec. 1998, pp. 279-305.

Maquat et al., "The Pioneer Round of Translation: Features and Functions", Cell, vol. 143, No. 3, Aug. 2010, pp. 368-374.

Padidam, Malla, "Chemically regulated Gene Expression in Plants", Current Opinion in Plant Biology, vol. 6, Issue 2, Apr. 2003, pp. 169-177.

Schuler, M. A., "Splice Site Requirements and Switches in Plants", Current Topics in Microbiology and Immunology, vol. 326, 2008, pp. 39-59.

Schwartz et al., "Large-Scale Comparative Analysis of Splicing Signals and their Corresponding Splicing Factors in Eukaryotes", Genome Research, vol. 18, No. 1, Jan. 2008, pp. 88-103.

Singer et al., "Enhancer-Promoter interference and its prevention in Transgenic Plants", Plant Cell Reports, vol. 30, Issue 5, May 2011, pp. 723-731.

Sudarsan et al., "Metabolite-Binding RNA domains are present in the Genes of Eukaryotes", RNA, vol. 9, No. 6, Jun. 2003, pp. 644-647.

Tai et al., "Expression of the Bs2 Pepper Gene Confers Resistance to Bacterial Spot Disease in Tomato", Proceedings of the National Academy of Sciences of the USA, vol. 96, No. 24, Nov. 1999, pp. 14153-14158.

Terzi et al., "Regulation of Flowering Time by RNA Processing", Current Topics in Microbiology and Immunology, vol. 326, 2008, pp. 201-218.

Wachter et al., "Riboswitch Control of Gene Expression in Plants by Splicing and Alternative 3' End Processing of mRNAs", Plant Cell, vol. 19, No. 11, Nov. 2007, pp. 3437-3450.

Wang et al., "Genomewide Comparative Analysis of Alternative Splicing in Plants", Proceedings of the National Academy of Sciences of USA, vol. 103, No. 18, 2006, pp. 7175-7180.

Weigand et al., "Tetracycline Aptamer-Controlled Regulation of Pre-mRNA Splicing in Yeast", Nucleic Acids Research, vol. 35, No. 12, 2007, pp. 4179-4185.

Yoine et al., "The Iba1 Mutation of UPF1 RNA Helicase involved in Nonsense-Mediated mRNA Decay Causes Pleiotropic Phenotypic Changes and Altered Signalling in Arabidopsis", The Plant Journal, vol. 47, Issue 1, Jul. 2006, pp. 49-62.

* cited by examiner

Without dexamethasone, GVG transcription factor is localized in the cytoplasm:

Promoter is "off." Leaky transcript pre-mRNA will splice to retain HyP5SM. This splice product does not lead to protein.

With dexamethasone, GVG localizes to the nucleus:

Productive splice product leads to AvrBs2 protein.

| Single | Constitutive:*Bs2-HA* (resistance gene), Inducible:*avrBs2-HA* (bacterial effector), Inducible:*OsL5* | (a) | (b) |
|---|---|---|---|
| Dual | Constitutive:*Bs2-HA*, Inducible:*avrBs2-HyP5SM-HA*, Inducible:*OsL5* (for HyP5SM skipping) | (c) | (d) |
| | Hypersensitive response | −Dex | +Dex (3μM) |

Figure 19

P5SM SUICIDE EXON FOR REGULATING GENE EXPRESSION

CROSS-REFERENCE TO RELATED APPLICATION

This application claims the benefit of U.S. Provisional Application No. 61/589,812, filed Jan. 23, 2012, which is hereby incorporated by reference, in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 416272009600SubSeqList.txt, date recorded: Jun. 27, 2013, size: 32 KB).

FIELD OF THE INVENTION

The present disclosure relates to inducible hybrid plant 5S rRNA mimic (P5SM) RNA elements that regulate gene expression by alternative splicing, and to methods of using such RNA elements for regulating transgene expression in eukaryotic host cells and plants.

BACKGROUND OF THE INVENTION

Alternative splicing of precursor mRNAs (pre-mRNAs) is an important and widely conserved mechanism for increasing protein diversity and for gene regulation. In plants and other eukaryotes, tissue-specific and development-specific expression of genes is regulated by alternative splicing (1-3). Changes in pre-mRNA splicing of plant transcripts have been observed in response to stress conditions, including growth in cold temperature or under drought conditions (4). Alternative splicing also has been shown to contribute to diverse physiological processes in plants, including regulation of circadian rhythm and the defense response to pathogens (5, 6). Altogether, it has been estimated that between 20-30% of expressed genes are alternatively spliced in *Arabidopsis thaliana* and *Oryza sativa* (rice) (7, 8).

While alternative splicing appears to be extensively employed in natural regulatory systems, it has not been generally applied to the conditional expression of transgenes. Currently, transgene regulation is based almost exclusively on transcriptional activation. This is due, in no small part, to the ease of placing a promoter sequence upstream of any gene of interest, which requires little to no characterization of promoter elements and no alteration of the coding sequence. However, many conditional promoters suffer from issues such as leaky basal expression, pleiotropic effects, and species specificity (9). Promoters are also difficult to combine serially in order to generate complex regulatory patterns, as cross-talk between different promoter elements often leads to unpredictable effects on gene expression (10). Furthermore, use of multiple copies of identical promoters to coordinate regulation of several genes can trigger gene silencing (11). Thus, one reason for developing techniques based on alternative splicing for transgene regulation is that problems with existing conditional promoters may be ameliorated by combining DNA- and RNA-level regulation. Another advantage of a conditional splicing system is that the gene can be regulated and still remain under the control of its endogenous promoter.

Similar to conditional promoters that do not change the sequence of a translated ORF, alternative splicing of a cassette harboring a suicide exon can also be considered to operate in a traceless manner. Exon skipping would generate a productively translated spliced product (SP-I) with the suicide exon cleanly excised from the sequence of the ORF. Alternatively, exon inclusion would introduce a premature termination codon that targets the spliced product (SP-II) for nonsense-mediated decay (NMD) instead of undergoing translation (12). Thus, the presence of a suicide exon effectively eliminates gene expression, and its conditional splicing regulates expression of the encoded ORF. The coupling of alternative splicing to mRNA quality control pathways is conserved as a regulatory mechanism in diverse eukaryotic organisms, including plants, fungi, and metazoans (13), so this method for transgene regulation could have broad applicability.

Currently, only a few conditional splicing systems have been constructed that regulate gene expression in eukaryotic cells such as budding yeast (14) and mammalian cells (15, 16). These studies were performed either on single reporter constructs or in the context of gene fusions which introduced extraneous sequences to the N-terminus of the ORF, similar to minigene reporters used in splicing assays (17). In addition, a natural riboswitch has been discovered that regulates gene expression through alternative splicing in response to thiamine pyrophosphate (TPP) in plants and filamentous fungi (18-21). The untranslated regions (UTRs) containing the TPP riboswitch have been appended to reporter constructs. However, one problem with this riboswitch is that the level of gene activation is only modest even in thiamine-deficient plant lines, as levels of the spliced product which gives higher gene expression was increased ~7-fold upon thiamine depletion (20). Thus, it has remained unclear whether conditionally spliced transgenes can be reliably designed for robust gene activation, such that this method is generalizable to any gene of interest.

Moreover, pre-mRNA splicing reactions can be sensitive to sequence context, as even single nucleotide polymorphisms have been shown to cause aberrant splicing in some genes (22). Thus, maintaining the fidelity and regulation of alternative splicing within diverse coding sequences can also be quite challenging.

Accordingly, a need exists for conditional splicing systems that provide robust gene activation for any gene of interest, and that maintain the fidelity and regulation of alternative splicing within diverse coding sequences.

BRIEF SUMMARY

In order to meet the above needs, the present disclosure provides novel hybrid plant 5S rRNA mimic (P5SM) RNA elements, and methods of using such RNA elements for regulating expression of transgenes in eukaryotic organisms, such as yeast, mammalian cells, and plants. Moreover, the present disclosure is based, at least in part, on the discovery of a natural splicing cassette that contains a P5SM suicide exon that was successfully inserted into various genes to regulate their expression in plants. Advantageously, the splicing cassette function was shown to only require conservation of two upstream nucleotides in the coding sequence of the gene of interest to maintain splicing fidelity. This allows the P5SM suicide exon to be quite general. Additionally, it was shown that plants having transgenes containing a hybrid P5SM suicide exon had robust gene activation of the transgene (up to 97-fold) without any background expression when the splicing cassette was induced.

Accordingly, certain aspects of the present disclosure relate to an isolated DNA encoding a plant 5S rRNA mimic (P5SM) containing pairing elements P1, P2, P3a, P3b, and P3c; and loops L2 and L3, where the P1, P2, P3a, P3b, and P3c pairing elements, and the L3 loop are derived from a first plant species; and the L2 loop is derived from a second plant species.

In certain embodiments, the first plant species is a monocotyledonous plant species. In certain embodiments, the monocotyledon plant species is *Oryza sativa*. In certain embodiments that may be combined with any of the above embodiments, the L2 loop contains an extended purine-rich sequence. In certain embodiments that may be combined with any of the above embodiments, the second plant species is a dicotyledonous plant species. In certain embodiments, the dicotyledonous plant species is *Arabidopsis thaliana*. In certain embodiments that may be combined with any of the above embodiments, the P5SM contains at least one nucleotide substitution in one or more pairing elements selected from P1, P2, P3a, P3b, and P3c; or one or more of loops selected from L2 and L3. In certain embodiments that may be combined with any of the above embodiments, the isolated DNA further contains a nucleotide aptamer that binds a chemical inducer. In certain embodiments that may be combined with any of the above embodiments, binding of the chemical inducer to the nucleotide aptamer induces excision of the modified P5SM from a gene transcript when the modified P5SM is incorporated into a gene in a host organism. In certain embodiments that may be combined with any of the above embodiments, binding of the chemical inducer to the nucleotide aptamer inhibits excision of the modified P5SM from a gene transcript when the modified P5SM is incorporated into a gene in a host organism. In certain embodiments that may be combined with any of the above embodiments, the P5SM contains a nucleotide sequence that is at least 70%, at least 75%, at least 80%, at least 85%, at least 90%, at least 95%, at least 96%, at least 97%, at least 98%, at least 99%, or 100% identical to SEQ ID NO: 1 (HyP5SM). In certain embodiments that may be combined with any of the above embodiments, the P5SM contains SEQ ID NO: 1.

Other aspects of the present disclosure relate to a vector containing a transgene operably linked to a regulatory sequence, where the transgene contains the isolated DNA of any of the above embodiments. In certain embodiments, the transgene contains an Adenine nucleotide at position −2 of the 5' splice site of the P5SM, and a Guanine nucleotide at position −1 of the 5' splice site of the P5SM. In certain embodiments that may be combined with any of the above embodiments, the regulatory sequence is selected from a constitutive promoter sequence, an inducible promoter sequence, and the endogenous promoter sequence of the transgene. In certain embodiments that may be combined with any of the above embodiments, the regulatory sequence is the endogenous promoter sequence of the transgene. In certain embodiments that may be combined with any of the above embodiments, the regulatory sequence is a constitutive promoter sequence or an inducible promoter sequence.

Other aspects of the present disclosure relate to a host cell containing the vector of any of the above embodiments. In certain embodiments, transgene protein expression is inhibited by the presence of the P5SM. In certain embodiments that may be combined with any of the above embodiments, excision of the P5SM allows transgene protein expression.

In certain embodiments that may be combined with any of the above embodiments, the host cell further contains a second vector operably linked to an inducible promoter sequence, where the second vector contains a recombinant nucleotide encoding an L5 ribosomal protein. In certain embodiments, the L5 ribosomal protein is derived from the first plant species. In certain embodiments that may be combined with any of the above embodiments, the L5 ribosomal protein is a transgenic L5 ribosomal protein. In certain embodiments that may be combined with any of the above embodiments, the L5 ribosomal protein induces excision of the P5SM. In certain embodiments that may be combined with any of the above embodiments, the host cell is a eukaryotic cell selected from a fungal cell, a yeast cell, a plant cell, an insect cell, and a mammalian cell. Other aspects of the present disclosure relate to a transgenic plant containing the vector of any of the above embodiments. Other aspects of the present disclosure relate to seed of the transgenic plant of the above embodiment.

Other aspects of the present disclosure relate to a method of regulating transgene expression in a eukaryotic cell, by: (a) providing a eukaryotic cell containing a first vector and a second vector, where the first vector is the vector of any of the above embodiments, and the second vector contains a recombinant polynucleotide encoding an L5 ribosomal protein, where the second vector is operably linked to an inducible promoter sequence; (b) culturing the eukaryotic cell under conditions whereby the first vector is expressed to produce mRNA comprising the P5SM; and (c) inducing expression of the L5 ribosomal protein in the eukaryotic cell, where the L5 ribosomal protein induces excision of the P5SM from the mRNA, thereby allowing transgene protein expression. In certain embodiments, the eukaryotic cell selected from a fungal cell, a yeast cell, a plant cell, an insect cell, and a mammalian cell.

Other aspects of the present disclosure relate to a method of regulating transgene expression in a plant, by: (a) providing a plant containing a first vector and a second vector, where the first vector is the vector of any of the above embodiments, and the second vector contains a recombinant polynucleotide encoding an L5 ribosomal protein, where the second vector is operably linked to an inducible promoter sequence; (b) growing the plant under conditions whereby the first vector is expressed to produce mRNA comprising the P5SM; and (c) inducing the expression of the L5 ribosomal protein in the plant, where the L5 ribosomal protein induces excision of the P5SM from the mRNA, thereby allowing transgene protein expression.

In certain embodiments that may be combined with any of the above embodiments, transgene protein expression is inhibited by the presence of the P5SM. In certain embodiments that may be combined with any of the above embodiments, the L5 ribosomal protein is derived from monocotyledonous plant species. In certain embodiments, the monocotyledon plant species is *Oryza sativa*. In certain embodiments that may be combined with any of the above embodiments, the L5 ribosomal protein is a transgenic L5 ribosomal protein.

Other aspects of the present disclosure relate to an isolated DNA encoding a plant 5S rRNA mimic (P5SM) containing pairing elements P1, P2, P3a, P3b, and P3c; and loops L2 and L3, where the P5SM is capable of binding to an L5 ribosomal protein resulting in excision of the P5SM from a gene transcript when the P5SM is incorporated into a gene in a host organism; where the P5SM contains at least one modification in one or more of the pairing elements and/or one or more of the loops; where the modified P5SM is incapable of binding to an L5 ribosomal protein and excising from a gene transcript in response to L5 ribosomal protein binding when the modified P5SM is incorporated into a gene in a host organism; and where the isolated DNA further contains a nucleotide aptamer.

In certain embodiments, the isolated DNA further contains a 5' splice site and a 3' splice site. In certain embodiments, the nucleotide aptamer overlaps the 5' splice site or the 3' splice site. In certain embodiments, the nucleotide aptamer binds a chemical inducer. In certain embodiments, binding of the chemical inducer to the nucleotide aptamer induces excision of the modified P5SM from a gene transcript when the modified P5SM is incorporated into a gene in a host organism. In certain embodiments that may be combined with any of the above embodiments, the P5SM contains a modification in the P2 pairing element. In certain embodiments, the modification is a nucleotide substitution in at least one, at least two, at least three, at least four, at least five, or at least six nucleotides within the P2 pairing element.

Other aspects of the present disclosure relate to an isolated DNA encoding a plant 5S rRNA mimic (P5SM) containing pairing elements P1, P2, P3a, P3b, and P3c; and loops L2 and L3, where the P5SM is capable of binding to an L5 ribosomal protein resulting in excision of the P5SM from a gene transcript when the P5SM is incorporated into a gene in a host organism; where the P5SM contains at least one modification in one or more of the pairing elements and/or one or more of the loops; where the modified P5SM is incapable of responding to an L5 ribosomal protein resulting in constitutive excision from a gene transcript when the modified P5SM is incorporated into a gene in a host organism; and where the isolated DNA further contains a nucleotide aptamer.

In certain embodiments, the isolated DNA further contains a 5' splice site and a 3' splice site. In certain embodiments, the nucleotide aptamer overlaps the 5' splice site or the 3' splice site. In certain embodiments, the nucleotide aptamer binds a chemical inducer. In certain embodiments, binding of the chemical inducer to the nucleotide aptamer inhibits excision of the modified P5SM from a gene transcript when the modified P5SM is incorporated into a gene in a host organism. In certain embodiments that may be combined with any of the above embodiments, the P5SM contains a modification in the P2 pairing element or a modification in the L2 loop. In certain embodiments, the modification is a nucleotide substitution in at least one, at least two, at least three, at least four, at least five, or at least six nucleotides within the P2 pairing element or the L2 loop.

In certain embodiments that may be combined with any of the above embodiments, the chemical inducer is theophylline or tetracycline. In certain embodiments that may be combined with any of the above embodiments, the P5SM contains at least two, at least three, at least four, or at least five modifications in one or more of the pairing elements and/or one or more of the loops. In certain embodiments that may be combined with any of the above embodiments, the P5SM further contains a second modification, where the second modification is an extended purine-rich sequence in the L2 loop. In certain embodiments that may be combined with any of the above embodiments, the L2 loop is derived from a dicotyledonous plant species. In certain embodiments, the dicotyledonous plant species is *Arabidopsis thaliana*.

Other aspects of the present disclosure, relate to a vector containing a transgene operably linked to a regulatory sequence, where the transgene contains the isolated DNA of any of the above embodiments containing a modified P5SM that is incapable of binding to an L5 ribosomal protein and excising from a gene transcript in response to L5 ribosomal protein binding when the modified P5SM is incorporated into a gene in a host organism. In certain embodiments, the transgene contains an Adenine nucleotide at position −2 of the 5' splice site of the modified P5SM, and a Guanine nucleotide at position −1 of the 5' splice site of the modified P5SM. In certain embodiments that may be combined with any of the above embodiments, the regulatory sequence is the endogenous promoter sequence of the transgene. In certain embodiments that may be combined with any of the above embodiments, the regulatory sequence is a constitutive promoter sequence or an inducible promoter sequence. In certain embodiments that may be combined with any of the above embodiments, the where the P5SM further contains a second modification, where the second modification is an extended purine-rich sequence in the L2 loop.

Other aspects of the present disclosure, relate to a vector containing a transgene operably linked to a regulatory sequence, where the transgene contains the isolated DNA of any of the above embodiments containing a modified P5SM that is incapable of responding to an L5 ribosomal protein resulting in constitutive excision from a gene transcript when the modified P5SM is incorporated into a gene in a host organism. In certain embodiments, the transgene contains an Adenine nucleotide at position −2 of the 5' splice site of the modified P5SM, and a Guanine nucleotide at position −1 of the 5' splice site of the modified P5SM. In certain embodiments that may be combined with any of the above embodiments, the regulatory sequence is the endogenous promoter sequence of the transgene. In certain embodiments that may be combined with any of the above embodiments, the regulatory sequence is a constitutive promoter sequence or an inducible promoter sequence.

Other aspects of the present disclosure relate to a host cell containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism. In certain embodiments, protein expression of the transgene is inhibited by the presence of the isolated DNA. In certain embodiments that may be combined with any of the above embodiments, addition of a chemical inducer allows transgene protein expression. In certain embodiments that may be combined with any of the above embodiments, the chemical inducer is theophylline or tetracycline.

Other aspects of the present disclosure relate to a host cell containing the vector of any of the above embodiments, where the vector contains a modified P5SM that is incapable of responding to an L5 ribosomal protein resulting in constitutive excision from a gene transcript when the modified P5SM is incorporated into a gene in a host organism. In certain embodiments, addition of a chemical inducer inhibits transgene protein expression. In certain embodiments that may be combined with any of the above embodiments, the chemical inducer is theophylline or tetracycline.

In certain embodiments that may be combined with any of the above embodiments, the host cell is a eukaryotic cell selected from a fungal cell, a yeast cell, a plant cell, an insect cell, and a mammalian cell. Other aspects of the present disclosure relate to a transgenic plant containing the vector of any of the above embodiments. Other aspects of the present disclosure relate to seed of the transgenic plant of the above embodiment.

Other aspects of the present disclosure relate to a method of regulating transgene expression in a eukaryotic cell, by: (a) providing a eukaryotic cell containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; (b) culturing the eukaryotic cell under conditions whereby the vector is expressed to produce mRNA comprising the modified P5SM and the nucleotide aptamer; and (c) adding a chemical inducer to the eukaryotic cell, where the chemical inducer binds the nucleotide aptamer resulting in excision of the modified P5SM from the mRNA, thereby allowing transgene protein expression. In certain embodiments, the eukaryotic cell is selected from a fungal cell, a yeast cell, a plant cell, an insect cell, and a mammalian cell.

Other aspects of the present disclosure relate to a method of regulating transgene expression in a plant, by: (a) providing a plant containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; (b) growing the plant under conditions whereby the vector is expressed to produce mRNA comprising the modified P5SM and the nucleotide aptamer; and (c) adding a chemical inducer to the plant, where the chemical inducer binds the nucleotide aptamer resulting in excision of the modified P5SM from the mRNA, thereby allowing transgene protein expression.

In certain embodiments that may be combined with any of the above embodiments, transgene protein expression is inhibited by the presence of the modified P5SM.

Other aspects of the present disclosure relate to a method of regulating transgene expression in a eukaryotic cell, by: (a) providing a eukaryotic cell containing the vector of any of the above embodiments, where the vector contains a modified P5SM that is incapable of responding to an L5 ribosomal protein resulting in constitutive excision from a gene transcript when the modified P5SM is incorporated into a gene in a host organism; (b) culturing the eukaryotic cell under conditions whereby the vector is expressed to produce mRNA comprising the modified P5SM and the nucleotide aptamer; and (c) adding a chemical inducer to the eukaryotic cell, where the chemical inducer binds the nucleotide aptamer resulting in inhibition of P5SM excision from the mRNA, thereby inhibiting transgene protein expression. In certain embodiments, the eukaryotic cell is selected from a fungal cell, a yeast cell, a plant cell, an insect cell, and a mammalian cell.

Other aspects of the present disclosure relate to a method of regulating transgene expression in a plant, by: (a) providing a plant containing the vector of any of the above embodiments, where the vector contains a modified P5SM that is incapable of responding to an L5 ribosomal protein resulting in constitutive excision from a gene transcript when the modified P5SM is incorporated into a gene in a host organism; (b) growing the plant under conditions whereby the vector is expressed to produce mRNA comprising the modified P5SM and the nucleotide aptamer; and (c) adding a chemical inducer to the plant, where the chemical inducer binds the nucleotide aptamer resulting in inhibition of P5SM excision from the mRNA, thereby inhibiting transgene protein expression.

In certain embodiments that may be combined with any of the above embodiments, the chemical inducer is theophylline or tetracycline.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2 shows a sequence alignment of representative P5SM elements from various plant species. The sequence alignment shows the conservation of sequence and structure. Nucleotides forming pairing interactions P1 through P3 are highlighted in color. Each sequence is annotated with the organism code (see Legend) and the corresponding NCBI gi accession number (for ESTs/cDNAs) or gene locus id (for sequenced genomes). The *Physcomitrella patens* (moss) sequence is displayed on a separate line because it is significantly diverged from the other sequence examples, which are from angiosperms. All sequences except for the example from *P. patens* were used to calculate conservation of nucleotide identity and presence, and covariation or compatible mutations in base-pairing interactions. *Arabidopsis thaliana* genomic data was obtained from TAIR, *Oryza sativa* genomic data was obtained from RAP-DB, *Populus trichocarpa* genomic data was obtained from DoE Joint Genome Institute (JGI) and Poplar Genomic Consortium, *Vitis vinifera* genomic data was obtained from Genoscope, and *Physcomitrella patens* genomic data was obtained from Cosmoss.

FIG. 3A shows a schematic representation of the P5SM splicing cassette (boxed) within gene constructs TFIIIA-eGFP (native context, top) and eGFP-P5SM$_{E/R}$ (foreign context, bottom). The eGFP coding sequence is shaded. The cassette exon contains the P5SM RNA element and an in-frame premature termination codon (X). The splicing reactions that generate spliced products SP-I and SP-II are shown. FIG. 3B shows eGFP-P5SM$_{E/R}$ spliced products detected by RT-PCR upon induction with AtL5 (+) or LUC as a control (−). FIG. 3C shows the relative amounts of the spliced products of eGFP-P5SM$_{E/R}$ determined by RT-qPCR. Data are averaged with number of biological replicates (n) and standard deviations shown. The P-value was determined using the paired t-test. FIG. 3D shows the fold induction of protein expression quantified by eGFP fluorescence for each construct. Induction with AtL5 was measured in comparison to induction with LUC as a control. FIG. 3E shows the representative whole leaf scan of eGFP fluorescence 3 days post-infiltration for each construct. The right leaf halves co-expressed AtL5 and the left halves co-expressed LUC (control).

FIG. 5A shows a schematic representation of the TFIIIA-eGFP gene construct showing the location of the mutated bordering codons (labeled NNN). The eGFP sequence is shown in green. Aberrant spliced products (red lines) are described in the Example. FIG. 5B shows a comparison of spliced products detected by RT-PCR for select 5' ss mutations tested within the TFIIIA-eGFP context. FIG. 5C shows a comparison of spliced products detected by RT-PCR for select 3' ss mutations tested within the TFIIIA-eGFP context. Mutants were co-expressed with AtL5 (+) or LUC as a control (−). Spliced products are labeled. The mutants are categorized as fully functional (green), semi-functional (yellow), or non-functional (red). Red nucleotides indicate the mutations made to the bordering codon, and the corresponding encoded amino acid is listed below. FIG. 5D shows fold induction of protein expression quantified by eGFP fluorescence for select TFIIIA-eGFP mutants. Induction with AtL5 was measured by comparison to induction with LUC as a control. For each mutant construct, the two amino acids encoded by the 5' and 3' bordering codons are indicated.

FIGS. 6A and 6B show the spliced products detected by RT-PCR for additional TFIIIA-P5SME/R mutants, which were characterized as fully functional. Red nucleotides indicate the mutations made to the bordering codons, and the two amino acids encoded by the 5' and 3' codons are indicated. FIG. 6C shows the fold induction of protein expression determined by eGFP fluorescence for M17 and M15. Induction with AtL5 was measured in comparison to induction with LUC as a control.

FIG. 7A shows RT-PCR detection of spliced products for firefly luciferase (fLUC) and abscissic acid 8'-hydroxylase (CYP707A3) harboring the P5SM cassette inserted within the E/R, K/R, or E/S sequence contexts, upon induction with AtL5 (+) or LUC as a control (−). FIG. 7B shows relative amounts of SP-I transcript for fLUC constructs determined by RT-qPCR. Data are averages with number of biological replicates (n) and standard deviations shown. The P-value was determined using the paired t-test. FIG. 7C shows luciferase activity in relative light units of fLUC constructs normalized to total protein upon induction with AtL5 (+) or control (−). Fold induction by AtL5 is shown at the top of each bar. FIG. 7D shows RT-PCR detection of spliced products for phytoene synthase (PSY) harboring the P5SM cassette inserted within the C/R sequence context upon induction with AtL5 (+) or LUC as a control (−). A schematic representation of the identified aberrant spliced products (right) shows cryptic splicing from a proximal GU in the coding sequence.

FIG. 8A shows fold induction of protein expression quantified by eGFP fluorescence for reporters harboring the OsP5SM or HyP5SM RNA elements within the splicing cassette. Induction with AtL5 or OsL5 was each measured in comparison to induction with LUC as a control. FIG. 8B shows fluorescence of eGFP-HyP5SM without co-infiltration with DsRed2 and with subtraction of background autofluorescence for individual leaf samples. Fold induction by OsL5 relative to induction with LUC as a control is shown. Background subtraction gives a negative fluorescence value (*) for leaf 4 in the absence of OsL5 induction, so the fold induction could not be determined for this sample. FIG. 8C shows representative whole leaf scans of eGFP fluorescence for reporters harboring OsP5SM or HyP5SM. The right leaf halves co-expressed AtL5 or OsL5 and the left halves co-expressed LUC as a control. All samples except for the one labeled "No DsRed2" also co-expressed DsRed2 on both leaf halves. FIG. 8D shows RT-PCR detection of spliced products for eGFP-OsP5SM and eGFP-HyP5SM upon induction with AtL5, OsL5, or LUC as a control.

FIG. 9A shows the secondary structure and sequence of the *Arabidopsis thaliana* P5SM RNA element (SEQ ID NO: 2). FIG. 9B shows the secondary structure and sequence of the *Oryza saliva* P5SM (OsG200116000) RNA element (SEQ ID NO: 3). Red nucleotides represent sequence differences in the L2 loop, the putative binding site of an exon-defining splice factor. HyP5SM was constructed by replacing the L2 loop from OsP5SM with the L2 loop from AtP5SM by overlap extension PCR.

FIG. 10A shows fluorescence of blank (autofluorescence), LUC (control), or DsRed2 (normalization standard) measured at the wavelength used to detect eGFP fluorescence (520 nm). FIG. 10B shows raw fluorescence data for leaf samples co-expressing LUC as a control or OsL5 were corrected for the average background autofluorescence measured from blank leaf samples. FIG. 10C shows representative whole leaf scans for blank, LUC, or DsRed2 only. Also, representative whole leaf scans for the eGFP reporter harboring the HyP5SM cassette co-expressing AtL5, OsL5, or LUC as a control. Matching fluorescence scans at wavelengths for detecting eGFP (520 nm) and DsRed2 (580 nm) are shown.

FIG. 11A shows immunoblot analysis of GFP expression for four different replicate sets of crude protein extracts from *N. benthamiana* leaf halves infiltrated with the reporter construct, eGFP-HyP5SM, inducer (OsL5) or control (LUC), and DsRed2 as a normalization standard, as described for the leaf-based fluorescence assay. FIG. 11B shows gelcode Blue staining of the blot shown in A, which visualizes all proteins present on the blot. The major band in the leaf extracts corresponds to Rubisco.

FIG. 12A shows a concept for promoter stacking with the P5SM splicing cassette. Expression of a single gene is regulated directly by its own promoter (P2) and indirectly by the promoter driving expression of the inducer (P1). Introduction of additional splicing cassettes would enable stacking of more than two promoters. FIG. 12B shows a concept for coordinated regulation of transgenes with the P5SM splicing cassette. A single conditional promoter (P1) drives expression of the inducer, which can target multiple suicide exons. The DNA sequences of the splicing cassettes can be non-homologous, as the recognition element is an RNA structure, to avoid gene silencing. Different constitutive promoters (P2-P4) are used for the individual transgenes, as expression is instead coordinated by conditional alternative splicing.

FIG. 13A shows a chemical-inducible HyP5SM splicing cassette that activates gene expression in response to a chemical inducer.

FIG. 13B shows a chemical-inducible HyP5SM splicing cassette that inhibits gene expression in response to a chemical inducer.

Figure 1:
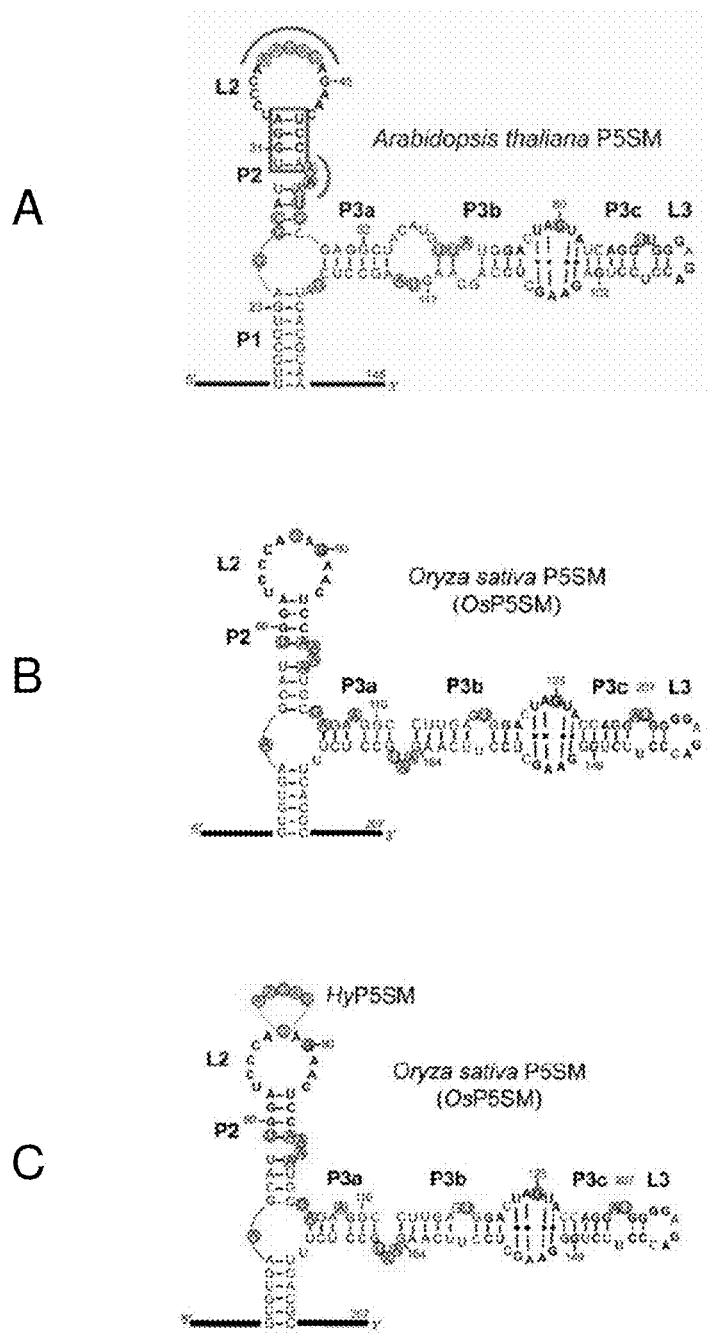
FIG. 1A shows a schematic of the secondary structure of the *Arabidopsis thaliana* P5SM (AtP5SM) cSEQ ID NO: 2).
FIG. 1B shows a schematic of the secondary structure of the *Oryza sativa* P5SM (OsP5SM) (SEQ ID NO: 4).
FIG. 1C shows a schematic of the secondary structure of the hybrid P5SM (HyP5SM) (SEQ. ID NO: 4, with sequence differencees labled "HyP5SM").

FIG. 14 shows a schematic depicting the mutations to HyP5SM (SEQ ID NO: 161). RT-PCR and eGFP expression results of M5 and M8 mutants of HyP5SM exhibit constitutive off and on gene expression irrespective of protein inducer OsL5.

FIG. 15 shows a model of Hybrid Plant 5S rRNA Mimic (HyP5SM) co-transcriptional gene regulation of the avrBs2 gene. FIG. 15A shows splicing in the absence of the OsL5 inducer. FIG. 15B shows splicing in the presence of the OsL5 inducer.

FIG. 16 shows a model of regulation of AvrBs2 protein expression using an inducible promoter and the HyP5SM exon. FIG. 16A shows expression in the absence of the chemical inducer dexamethasone. FIG. 16B shows expression in the presence of the chemical inducer dexamethasone.

FIG. 17 shows RT-PCR analysis of inducible avrBs2-HyP5SM-HA transcriptional expression.

FIG. 18A shows western blot analysis of inducible avrBs2-HyP5SM-HA protein expression. FIG. 18B shows Ponceau S protein staining of nitrocellulose membrane used for western blot analysis.

FIG. 19 shows photographs of spot infiltrations of *Nicotiana benthamiana* leaves transiently transformed with inducible avrBs2-HyP5SM-HA and OsL5 showing the inducibility of the hypersensitive response. The photographs were taken 4 days after *Agrobacterium*-mediated transient transformations.

DETAILED DESCRIPTION

Definitions

Unless defined otherwise, all scientific and technical terms are understood to have the same meaning as commonly used in the art to which they pertain. For the purpose of the present disclosure, the following terms are defined.

As used herein, "plant 5S rRNA mimic" and "P5SM" are used interchangeably and refer to an RNA element residing within a highly conserved, alternatively spliced suicide exon that controls gene expression in eukaryotic organisms, such as land plants.

As used herein, a "derived from" a plant species refers to a fragment, section, motif, or domain of a polynucleotide, such as a P5SM, that is designed, purified, and/or isolated from a plant species. For example, in certain embodiments, the L2 loop of a hybrid P5SM element is the L2 loop of the *Arabidopsis thaliana* P5SM, while the rest of the hybrid P5SM element (i.e., the P1, P2, P3a, P3b, P3c pairing elements and the L3 loop) is that of the *Oryza sativa* P5SM element.

As used herein, a "gene" refers to a polynucleotide, or fragment thereof, that includes the coding sequence of a gene product, such as a protein.

As used herein, the terms "polynucleotide", "nucleic acid", "nucleic acid sequence", "sequence of nucleic acids", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; inter-nucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochem. 9:4022, 1970).

As used herein, a "polypeptide" is an amino acid sequence containing a plurality of consecutive polymerized amino acid residues (e.g., optionally at least about 15 consecutive polymerized amino acid residues, at least about 30 consecutive polymerized amino acid residues, or at least about 50 consecutive polymerized amino acid residues). In many instances, a polypeptide contains a polymerized amino acid residue sequence that is an enzyme, a methyltransferase, a demethylase, a deacteylase, a predicted protein of unknown function, or a domain or portion or fragment thereof. The polypeptide optionally contains modified amino acid residues, naturally occurring amino acid residues not encoded by a codon, and non-naturally occurring amino acid residues.

As used herein, "protein" refers to an amino acid sequence, oligopeptide, peptide, polypeptide, or portions thereof whether naturally occurring or synthetic.

Genes and proteins that may be used in the present disclosure include genes encoding conservatively modified variants and proteins that are conservatively modified variants of those genes and proteins described throughout the application. "Conservatively modified variants" as used herein include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Homologs of the genes and proteins described herein may also be used in the present disclosure. As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity. As used herein, "orthology" refers to genes in different species that derive from a common ancestor gene.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) *J Mol Biol* 48(3):443-453, by the search for similarity method of Pearson and Lipman (1988) *Proc Natl Acad Sci USA* 85(8):2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol. Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22): 10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

Overview

The present disclosure relates to isolated DNAs encoding a plant 5S rRNA mimic (P5SM) containing pairing elements P1, P2, P3a, P3b, P3c; and loops L2 and L3, where the P1, P2, P3a, P3b, P3c pairing elements, and the L3 loop are derived from a first plant species; and the L2 loop is derived from a second plant species. The present disclosure also relates to isolated DNAs encoding a P5SM containing pairing elements P1, P2, P3a, P3b, and P3c; and loops L2 and L3, where the P5SM is capable of binding to an L5 ribosomal protein resulting in excision of the P5SM from a gene transcript when the P5SM is incorporated into a gene in a host organism; where the P5SM contains at least one modification in one or more of the pairing elements and/or one or more of the loops; where the modified P5SM is incapable of binding to an L5 ribosomal protein and excising from a gene transcript in response to L5 ribosomal protein binding when the modified P5SM is incorporated into a gene in a host organism; and where the isolated DNA further contains a nucleotide aptamer. The present disclosure further relates to isolated DNAs encoding a P5SM containing pairing elements P1, P2, P3a, P3b, and P3c; and loops L2 and L3, where the P5SM is capable of binding to an L5 ribosomal protein resulting in excision of the P5SM from a gene transcript when the P5SM is incorporated into a gene in a host organism; where the P5SM contains at least one modification in one or more of the pairing elements and/or one or more of the loops; where the modified P5SM is incapable of responding to an L5 ribosomal protein resulting in constitutive excision from a gene transcript when the modified P5SM is incorporated into a gene in a host organism; and where the isolated DNA further contains a nucleotide aptamer. The present disclosure also relates to vectors containing such isolated DNAs, host cells containing such isolated DNAs and vectors, transgenic plants containing such isolated DNAs and vectors, and seed from such transgenic plants.

The present disclosure further relates to methods of regulating transgene expression in a eukaryotic cell, by providing a eukaryotic cell containing a first vector and a second vector, where the first vector is any of the above vectors containing isolated DNAs of the present disclosure, and the second vector contains a recombinant polynucleotide encoding an L5 ribosomal protein, where the second vector is operably linked to an inducible promoter sequence; culturing the eukaryotic cell under conditions whereby the first vector is expressed to produce mRNA comprising the P5SM; and inducing expression of the L5 ribosomal protein in the eukaryotic cell, where the L5 ribosomal protein induces excision of the P5SM from the mRNA, thereby allowing transgene protein expression. The present disclosure also relates to methods of regulating transgene expression in a plant, by providing a plant containing a first vector and a second vector, where the first vector is any of the above vectors containing isolated DNAs of the present disclosure, and the second vector contains a recombinant polynucleotide encoding an L5 ribosomal protein, where the second vector is operably linked to an inducible promoter sequence; growing the plant under conditions whereby the first vector is expressed to produce mRNA comprising the P5SM; and inducing the expression of the L5 ribosomal protein in the plant, where the L5 ribosomal protein induces excision of the P5SM from the mRNA, thereby allowing transgene protein expression.

The present disclosure further relates to methods of regulating transgene expression in a eukaryotic cell, by providing a eukaryotic cell containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; culturing the eukaryotic cell under conditions whereby the vector is expressed to produce mRNA comprising the modified P5SM and the nucleotide aptamer; and adding a chemical inducer to the eukaryotic cell, where the chemical inducer binds the nucleotide aptamer resulting in excision of the modified P5SM from the mRNA, thereby allowing transgene protein expression. The present disclosure also relates to methods of regulating transgene expression in a plant, by providing a plant containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; growing the plant under conditions whereby the vector is expressed to produce mRNA comprising the modified P5SM and the nucleotide aptamer; and adding a chemical inducer to the plant, where the chemical inducer binds the nucleotide aptamer resulting in excision of the modified P5SM from the mRNA, thereby allowing transgene protein expression.

The present disclosure also relates to methods of regulating transgene expression in a eukaryotic cell, by providing a eukaryotic cell containing the vector of any of the above embodiments, where the vector contains a modified P5SM that is incapable of responding to an L5 ribosomal protein resulting in constitutive excision from a gene transcript when the modified P5SM is incorporated into a gene in a host organism; culturing the eukaryotic cell under conditions whereby the vector is expressed to produce mRNA comprising the modified P5SM and the nucleotide aptamer; and adding a chemical inducer to the eukaryotic cell, where the chemical inducer binds the nucleotide aptamer resulting in inhibition of P5SM excision from the mRNA, thereby inhibiting transgene protein expression. The present disclosure also relates to methods of regulating transgene expression in a plant, by providing a plant containing the vector of any of the above embodiments, where the vector contains a modified P5SM that is incapable of responding to an L5 ribosomal protein resulting in constitutive excision from a gene transcript when the modified P5SM is incorporated into a gene in a host organism; growing the plant under conditions whereby the vector is expressed to produce mRNA comprising the modified P5SM and the nucleotide aptamer; and adding a chemical inducer to the plant, where the chemical inducer binds the nucleotide aptamer resulting in inhibition of P5SM excision from the mRNA, thereby inhibiting transgene protein expression.

P5SM Elements of the Present Disclosure

Certain aspects of the present disclosure relate to an isolated DNA encoding a plant 5S rRNA mimic (P5SM) containing pairing elements P1, P2, P3a, P3b, P3c; and loops L2 and L3, where the P5SM contains at least one modification in one or more of the pairing elements and/or one or more of the loops; and to the use of such isolated DNAs in regulating the expression of one or more transgenes in eukaryotic organisms, such as yeast, mammalian cells, and plants. In certain embodiments, the P5SM element contains at least two, at least three, at least four, at least five, or more modifications in one or more of the pairing elements and/or one or more of the loops. As used herein, a "modification" can be the addition of one or more nucleotides, a deletion of one or more nucleotides, or a substitution of one more nucleotides. Methods of modifying nucleotide molecules, such as RNA elements, are well known in the art and include, without limitation, molecular cloning, mutagenesis and screening, site-directed mutagenesis, and PCR mutagenesis. In certain embodiments, P5SM elements of the present disclosure are modified to confer better regulatory activity.

Advantageously, P5SM elements of the present disclosure can inducibly regulate expression of a transgene of interest. When not induced, a non-modified P5SM element that has been inserted into the coding region of the transgene introduces a premature termination codon that targets the expressed mRNA transcript for nonsense-mediated decay instead of undergoing translation. However, when a P5SM-specific inducer such as the ribosomal protein L5 is introduced, it binds P5SM and induces alternative splicing that removes P5SM from the expressed transgene transcript, resulting in protein expression of the transgene. Thus, the presence of a P5SM in a transgene allows for the controlled expression of the transgene.

P5SM elements of the present disclosure are RNA elements residing within a highly conserved, alternatively spliced suicide exon that controls expression in land plants (23, 26). P5SM elements of the present disclosure have a conserved secondary structure that resembled that of 5S rRNA. The secondary structure of P5SM contains the pairing elements P1, P2, P3a, P3b, and P3c; as well as the loops L2 and L3 (FIG. 1).

Figure 2:
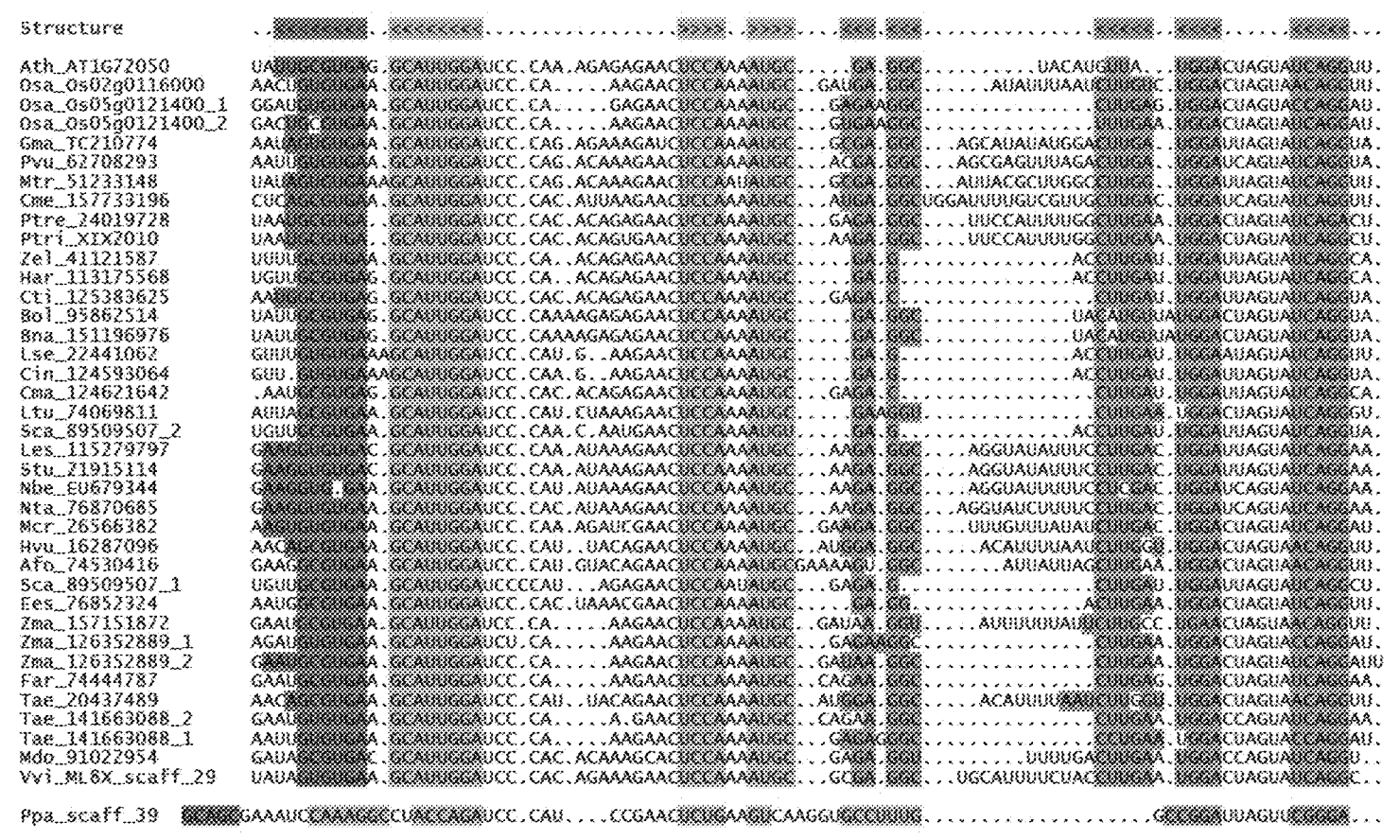
Figure 2:
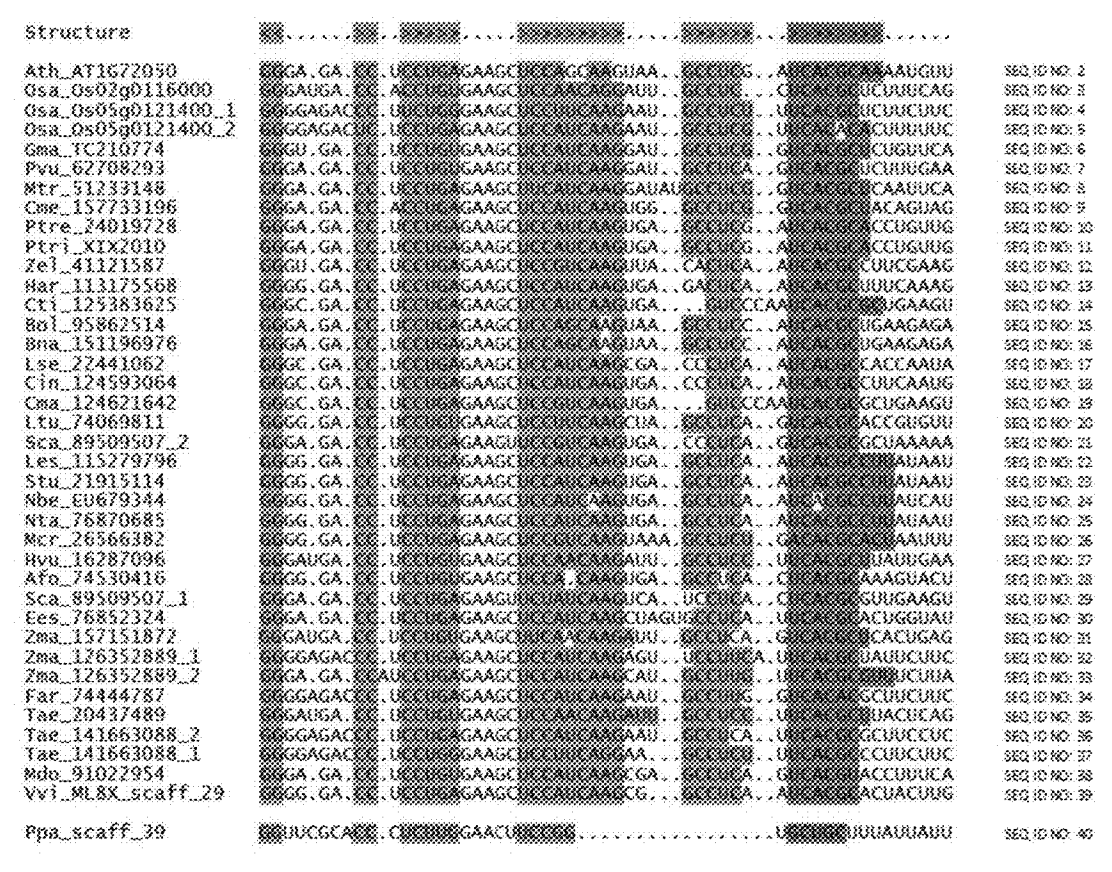

Suitable P5SM elements may be identified and isolated from monocot and dicot plants. Examples of such plants include, without limitation, *Arabidopsis* spp., *Oryza sativa*, and *Nicotiana benthamiana*. Examples of suitable P5SM elements include, without limitation, those listed in FIG. 2, homologs thereof, and orthologs thereof.

In certain embodiments, the P5SM element contains a modified L2 loop. In some embodiments, the L2 loop has been modified to contain an extended purine-rich sequence within the L2 loop. In certain preferred embodiments, the extended purine-rich sequence is the extended purine-rich sequence of L2 loop of the *A. thaliana* P5SM element.

While naturally-occurring P5SM elements maintain splicing fidelity and regulation within diverse transgene coding sequences, basal transgene activation from the endogenous expression of the P5SM induce ribosomal protein L5 contributes to background transgene expression. One solution to this problem is to use a P5SM element from a more divergent plant species from that of the host plant species containing the P5SM-inducible transgene that might be less responsive to the endogenous ribosomal L5 protein of the host plant. Accordingly, in embodiments where a transgene of interest is expressed in a plant, the P5SM element of the present disclosure is derived from a different plant species from that of the host plant species. For example, if the transgene is being expressed in a dicotyledonous plant species, then the P5SM element is may be derived from a monocotyledonous plant species.

The L2 loop of certain P5SM elements, such as the *A. thaliana* P5SM element has an extended purine-rich sequence. It had been shown that elimination of this purine-rich sequence leads to constitutive exon skipping (23). Moreover, P5SM elements from monocotyledonous plant species, such as *Oryza sativa*, do not contain an extended purine-rich sequence in the L2 loop. Accordingly, in certain embodiments, the P5SM element is a hybrid molecule that contains the P1, P2, P3a, P3b, and P3c pairing elements, and the L3 loop of a monocotyledonous plant species, such as *Oryza sativa*, and an L2 loop that contains an extended purine-rich sequence. Preferably, the L2 loop is from a dicotyledonous plant species, such as *Arabidopsis thaliana*.

In other embodiments, a P5SM element of the present disclosure has a nucleotide sequence that is at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% identical to the nucleotide sequence of HyP5SM (i.e., SEQ ID NO: 1).

Advantageously, P5SM elements of the present disclosure can require an effector protein, such that when coupled to a gene of interest expression of the gene becomes regulated by its own promoter and the promoter of the gene encoding the effector protein. Since the effector protein can control mRNA splicing and is not coupled to transcription of the gene of interest, the two promoters can be any two promoters. Accordingly, any two promoters can be stacked in parallel. Additionally, P5SM elements of the present disclosure can provide traceless regulation, as the mRNA processing step does not change or add any sequence to the open reading frame of the gene of interest.

Moreover, multiple distinct P5SM elements of the present disclosure that are recognized by the same effector protein may be used to coordinate the regulation of multiple genes of interest. This would be similar to how a transcription factor can be used to regulate a suite of genes by using the same promoter sequence over and over again. However, using the same promoter can be problematic due to homology-based gene silencing. By using P5SM elements, the splicing effector recognizes an RNA structure which can be encoded by non-homologous sequences. Thus use of the P5SM elements avoids the problem of homology-based gene silencing and genome instability.

Accordingly, P5SM elements of the present disclosure find many uses including, without limitation, regulation of gene expression, promoter stacking for RNA-based regulation of gene expression, and coordinated regulation of multiple genes.

P5SM elements of the present disclosure may also be used as tools in plant biology research, such as in the area of plant disease resistance. For example, P5SM elements may be used to elucidate the downstream signaling events in disease resistance signaling pathways, such as effector-triggered immunity signaling pathways.

Chemically Inducible P5SM Elements

P5SM elements of the present disclosure can also be modified so as to become unresponsive to the natural P5SM-specific inducer, such as the ribosomal protein L5. For example, the P2 pairing element of the P5SM element can be modified by substituting at least one, at least two, at least three, at least four, at least five, at least six, or more nucleotides such that the P5SM element can no longer binds the natural P5SM-specific inducer. Thus, when such a modified P5SM element is inserted into a transgene and the transgene is expressed, the modified P5SM element will not be excised from the mRNA transcript of the transgene in the presence of the natural P5SM-specific inducer and protein expression of the transgene will not occur.

Additionally, the P2 pairing element or the L2 loop of the P5SM element can also be modified by substituting at least one, at least two, at least three, at least four, at least five, at least six, or more nucleotides such that when the P5SM element is inserted into a transgene and the transgene is expressed, it will be excised from the mRNA transcript of the transgene in the absence of the natural P5SM-specific inducer. In this manner, the modified P5SM element is unresponsive to the natural P5SM-specific inducer, and is constitutively excised from the mRNA transcript of the transgene.

Such modified P5SM elements can be utilized in a P5SM splicing cassette that is incorporated into a gene of interest. Such a splicing cassette contains a 5' proximal splice site, a 5' distal splice site, a 3' proximal splice site, and a 3' distal splice site. When the distal splice sites are utilized, the P5SM element is excised from the mRNA of the expressed gene by spliceosomal processing of the mRNA. However, when the proximal splice sites are utilized, the P5SM element is retained in the mRNA of the expressed gene.

Such splicing cassettes containing a modified P5SM element can be adapted to be responsive to a chemical. For example, a splicing cassette containing the modified P5SM can also contain a nucleotide aptamer sequence that is specific for the chemical. In certain embodiments, the aptamer sequence is inserted to overlap the proximal 5' P5SM splice site or the proximal 3' P5SM splice site. Thus, when the chemical is introduced, the aptamer sequesters the proximal splice sites, which results in utilization of the distal splice sites and excision of the P5SM element. Advantageously, modified P5SM elements of the present disclosure that are not excised from the mRNA of an expressed transgene in the presence of the natural P5SM-specific inducer can be incorporated into a splicing cassette containing an aptamer sequence that overlaps the proximal 5' or 3' splice site in order to generate a P5SM element whose excision is induced by a chemical. Such a chemically inducible P5SM element can be incorporated into a transgene of interest so that protein expression of the transgene is induced by the chemical.

In other embodiments, the aptamer sequence is inserted to overlap the distal 5' P5SM splice site or the distal 3' P5SM splice site. Thus, when the chemical is introduced, the aptamer sequesters the distal splice sites, which results in utilization of the proximal splice sites and retention of the P5SM element. Advantageously, modified P5SM elements of the present disclosure that are constitutively excised from the mRNA of an expressed transgene can be incorporated into a splicing cassette containing an aptamer sequence that overlaps the distal 5' or 3' splice site in order to generate a P5SM element whose excision is inhibited by a chemical. Such a chemically inducible P5SM element can be incorporated into a transgene of interest so that protein expression of the transgene is inhibited by the chemical.

Suitable chemicals that can be used to induce the retention or excision of a modified P5SM element of the present disclosure include, without limitation, theophylline and tetracycline.

P5SM Induction

Other aspects of the present disclosure relate to inducing protein expression of a transgene in a host cell or plant by inducing excision of a modified P5SM element of the present disclosure from the mRNA of the expressed transgene, or inhibiting protein expression of a transgene in a host cell or plant by inducing the retention of a modified P5SM element of the present disclosure within the mRNA of the expressed transgene.

In certain embodiments, P5SM excision can be induced by the ribosomal protein L5. Generally, L5 binding to P5SM induces alternative splicing that causes the P5SM to be skipped during transcription. Accordingly, in certain embodiments, protein expression of the transgene is inhibited by the presence of the P5SM. In other embodiments, protein expression of the transgene is activated by inducing excision of the P5SM from the mRNA of the transgene. Any L5 ribosomal protein known in the art may be used to induce splicing out of the P5SM from the transgene. In certain embodiments, the L5 ribosomal protein is from the same plant species as the P1, P2, P3a, P3b, and P3c pairing elements and the L3 loop of the P5SM. Preferably, the L5 ribosomal protein is from a monocotyledonous plant species, such as *Oryza sativa*. In other embodiments, the L5 ribosomal protein is a transgenic L5 ribosomal protein.

Excision of the modified P5SM element can also be induced by a chemical inducer such as theophylline or tetracycline. Thus, in certain embodiments, transgene protein expression is induced by the chemical inducer.

In embodiments, where the P5SM is constitutively excised from the mRNA of a transgene, excision of the P5SM element can be inhibited by a chemical inducer such as theophylline or tetracycline. Thus, in certain embodiments, transgene protein expression is inhibited by the chemical inducer.

Transgenes of the Present Disclosure

Other aspects of the present disclosure relate to utilizing P5SM elements to regulate the expression of one or more transgenes of interest in eukaryotic organisms, such as yeast, mammalian cells, or plants, by inserting the P5SM element into the coding region of the one or more transgenes of interest.

As used herein, a "transgene" refers to a gene that has been modified to contain a P5SM element of the present disclosure. The "transgene" can be either endogenous or heterologous to the eukaryotic host into which the gene is transferred. Methods for inserting the P5SM element into the coding region of a gene of interest are well known in the art and include, without limitation, the methods described herein.

In certain embodiments, the one or more transgenes are derived from bacteria, fungi, algae, yeast, insects, mammals, or plants. Methods of introducing transgenes into eukaryotic hosts, such as yeast or plants, are well known in the art. Transgenes may be inserted into eukaryotic hosts in order to provide a production system for a desired protein, or may be added to the genetic compliment in order to modulate the metabolism of the eukaryotic host.

Examples of suitable transgenes include, without limitation, genes involved in lignocellulosic degradation, genes involved in lignocellulosic metabolism, genes involved in biochemical synthesis, genes involved in organic alcohol synthesis, genes involved in biofuel synthesis, genes involved in disease resistance, genes involved in pathogen resistance, genes involved in desiccation tolerance, genes involved in salt tolerance, and genes involved in fertility or sterility. In certain embodiments, the suitable genes may be genes encoding effector proteins, such as the avrBs2 gene and the ATR1Δ51 gene.

In certain embodiments, the transgene contains an Adenine nucleotide at position −2 of the 5' splice site of the P5SM, and a Guanine nucleotide at position −1 of the 5' splice site of the P5SM.

Vectors and Host Cells of the Present Disclosure

Certain aspects of the present disclosure relate to vectors containing a transgene of the present disclosure that is operably linked to a regulatory sequence, where the transgene contains a P5SM element of the present disclosure; and to host cells containing such vectors. Such host cells may be used to inducibly express the transgene. A transgene containing a P5SM element of the present disclosure may be included in an expression cassette and/or cloned into a suitable expression vector by standard molecular cloning techniques. Such expression cassettes or vectors contain regulatory sequences that assist initiation and termination of transcription (e.g., promoters and terminators), and generally contain a selectable marker.

Vectors

The expression cassette or vector is introduced in a suitable expression host cell, which then expresses the corresponding transgene containing a P5SM element of the present disclosure. Expression host cells may include, without limitation, fungal cells, yeast cells, algal cells, insect cells, mammalian cells, and plant cells. Particularly suitable yeast expression hosts such as *Saccharomyces cerevisiae, Schizosaccharomyces pombe, Yarrowia lipolytica, Hansenula polymorpha, Kluyveromyces lactis* or *Pichia pastoris*. Especially suited are fungal expression hosts such as *Aspergillus niger, Chrysosporium lucknowense, Aspergillus* (e.g., *A. oryzae, A. niger, A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the transgene containing a P5SM element of the present disclosure.

The vectors preferably contain one or more selectable markers which permit easy selection of transformed hosts. A selectable marker is a gene the product of which provides, for example, biocide or viral resistance, resistance to heavy metals, prototrophy to auxotrophs, and the like.

The vectors preferably also contain an element(s) that permits integration of the vector into the host's genome or autonomous replication of the vector in the cell independent of the genome.

Promoter sequences of the present disclosure can be the endogenous promoter sequence of the transgene containing a P5SM element of the present disclosure. Alternatively, the promoter sequence can be a heterologous promoter sequence that is either constitutive or inducible. Examples of suitable promoter sequences include any promoter sequence known in the art that drives expression of a gene in a particular host of interest.

For example, in embodiments where the transgene containing a P5SM element of the present disclosure is expressed in a plant cell, a plant promoter can be employed to control the expression of the transgene. Examples of suitable constitutive plant promoter sequences include, without limitation, the core promoter of the Rsyn7, the core CaMV 35S promoter (Odell et al., *Nature* (1985) 313:810-812), CaMV 19S (Lawton et al., 1987), rice actin (Wang et al., 1992; U.S. Pat. No. 5,641,876; and McElroy et al., *Plant Cell* (1985) 2:163-171); ubiquitin (Christensen et al., *Plant Mol. Biol.* (1989)12:619-632; and Christensen et al., *Plant Mol. Biol.* (1992) 18:675-689), pEMU (Last et al., *Theor. Appl. Genet.* (1991) 81:581-588), MAS (Velten et al., *EMBO J.* (1984) 3:2723-2730), nos (Ebert et al., 1987), Adh (Walker et al., 1987), the P- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the pEmu promoter, the rubisco promoter, the GRP 1-8 promoter, and other transcription initiation regions from various plant genes known to those of skilled artisans, and constitutive promoters described in, for example, U.S. Pat. Nos. 5,608,149; 5,608,144; 5,604,121; 5,569,597; 5,466,785; 5,399,680; 5,268,463; and 5, 608,142. Examples of inducible plant promoter sequences include, without limitation, the AdhI promoter which is inducible by hypoxia or cold stress, the Hsp70 promoter which is inducible by heat stress, and the PPDK promoter which is inducible by light.

Transgenes containing a P5SM element of the present disclosure are introduced into expression host cells by a number of transformation methods including, without limitation, electroporation, lipid-assisted transformation or transfection ("lipofection"), chemically mediated transfection (e.g., using calcium chloride and/or calcium phosphate), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

In certain embodiments, a vector of the present disclosure is a binary vector that can replicate in *E. coli* and *Agrobacterium tumefaciens*, but that only expresses the corresponding transgene containing a P5SM element of the present disclosure when introduced into plants.

Host Cells

Further aspects of the present disclosure relate to host cells containing vectors of the present disclosure that contain a transgene of interest containing a P5SM element of the present disclosure.

"Host cell" refers to a living biological eukaryotic cell that can be transformed via insertion of recombinant DNA or RNA. Such recombinant DNA or RNA can be in an expression vector. Any eukaryotic host cell may be used in the present disclosure so long as it remains viable after being transformed with a sequence of nucleic acids. Preferably, the host cell is not adversely affected by the transduction of the necessary nucleic acid sequences, the subsequent expression of the proteins or the resulting intermediates. Suitable eukaryotic cells include, without limitation, fungal, yeast, plant, insect, and mammalian cells.

Examples of suitable fungal cells include, without limitation, cells of the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as Oomycota (as cited in Hawksworth et al., 1995, supra, page 171) and all mitosporic fungi (Hawksworth et al., 1995, supra).

Examples of suitable yeast cells include, without limitation, *Candida, Hansenula, Issatchenkia, Kluyveromyces, Pichia, Saccharomyces, Schizosaccharomyces*, or *Yarrowia* strain. In other embodiments, the yeast host is a *Saccharomyces carlsbergensis* (Todkar, 2010), *Saccharomyces cerevisiae* (Duarte et al., 2009), *Saccharomyces diastaticus, Saccharomyces douglasii, Saccharomyces kluyveri, Saccharomyces norbensis, Saccharomyces monacensis* (GB-Analysts Reports, 2008), *Saccharomyces bayanus* (Kristen Publicover, 2010), *Saccharomyces pastorianus* (Nakao et al., 2007), *Saccharomyces pombe* (Mousdale, 2008), *Saccharomyces oviformis* strain, *Kluyveromyces lactis* (O. W. Merten, 2001), *Kluyveromyces fragilis* (Pestal et al., 2006; Siso, 1996), *Kluyveromyces marxiamus* (K. Kourkoutas et al., 2008), *Pichia stipitis* (Almeida et al., 2008), *Candida shehatae* (Ayhan Demirbas, 2003), or *Candida tropicalis* (Jamai et al., 2006), *Yarrowia lipolytica* (Biryukova E. N., 2009), *Brettanomyces custersii* (Spindler D. D. et al., 1992), and *Zygosaccharomyces* roux.

Examples of suitable plant cells include, without limitation, cells from plant species of the Family Gramineae, including *Sorghum bicolor* and *Zea mays*; species of the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale*, and *Triticum*.

The host cells of the present disclosure may be genetically modified in that a transgene containing a P5SM of the present disclosure has been introduced into the host cells, and as such the genetically modified host cells do not occur in nature.

In certain embodiments, protein expression of a transgene containing a P5SM element of the present disclosure is inhibited in the host cell by the presence of the P5SM. In other embodiments, protein expression of the transgene in the host cell is activated by inducing excision of the P5SM from the mRNA of the transgene. This may be accomplished by expressing an L5 ribosomal protein in the host cell. Accordingly, in certain embodiments, the host cell further contains a second vector containing a recombinant nucleotide encoding an L5 ribosomal protein, where the second vector is operably linked to an inducible promoter sequence. Any suitable inducible promoter sequence known in the art may be used.

In other embodiments, excision of the P5SM element is induced by a chemical inducer, such as theophylline or tetracycline. Thus in certain embodiments, addition of a chemical inducer to the host cell allows protein expression of the transgene.

In embodiments where the P5SM element is constitutively excised from the mRNA of the transgene, excision of the P5SM element can be inhibited by a chemical inducer, such as theophylline or tetracycline. Thus in certain embodiments, addition of a chemical inducer to the host cell inhibits protein expression of the transgene.

Plants of the Present Disclosure

Certain aspects of the present disclosure relate to transgenic plants containing a vector that expresses a transgene of interest containing a P5SM element of the present disclosure.

As used herein, a "plant" refers to any of various photosynthetic, eukaryotic multi-cellular organisms of the kingdom Plantae, characteristically producing embryos, containing chloroplasts, having cellulose cell walls and lacking locomotion. As used herein, a "plant" includes any plant or part of a plant at any stage of development, including seeds, suspension cultures, plant cells, embryos, meristematic regions, callus tissue, leaves, roots, shoots, gametophytes, sporophytes, pollen, microspores, and progeny thereof. Also included are cuttings, and cell or tissue cultures. As used in conjunction with the present disclosure, plant tissue includes, without limitation, whole plants, plant cells, plant organs, e.g., leafs, stems, roots, meristems, plant seeds, protoplasts, callus, cell cultures, and any groups of plant cells organized into structural and/or functional units.

As disclosed herein, a broad range of plant types may be modified to incorporate a transgene of interest containing a P5SM element of the present disclosure. Suitable plants that may be modified include both monocotyledonous (monocot) plants and dicotyledonous (dicot) plants.

Examples of suitable plants include, without limitation, species of the Family Gramineae, including *Sorghum bicolor* and *Zea mays*; species of the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale*, and *Triticum*.

In certain embodiments, plants may also include, without limitation, those from canola (*Brassica napus, Brassica rapa* ssp.), *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), duckweed (*Lemna*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucijra*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia* spp.), almond (*Prunus amygdalus*), sugar beets (*Beta vulgaris*), sugarcane (*Saccharum* spp.), oats, barley, vegetables, ornamentals, and conifers.

Examples of suitable vegetables plants include, without limitation, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Examples of suitable ornamental plants include, without limitation, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbiapulcherrima*), and chrysanthemum.

Examples of suitable conifer plants include, without limitation, loblolly pine (*Pinus taeda*), slash pine (*Pinus elliotii*), ponderosa pine (*Pinus ponderosa*), lodgepole pine (*Pinus contorta*), Monterey pine (*Pinus radiata*), Douglas-fir (*Pseudotsuga menziesii*), Western hemlock (*Isuga canadensis*), Sitka spruce (*Picea glauca*), redwood (*Sequoia sempervirens*), silver fir (*Abies amabilis*), balsam fir (*Abies balsamea*), Western red cedar (*Thuja plicata*), and Alaska yellow-cedar (*Chamaecyparis nootkatensis*).

Examples of suitable leguminous plants include, without limitation, guar, locust bean, fenugreek, soybean, garden beans, cowpea, mungbean, lima bean, fava bean, lentils, chickpea, peanuts (*Arachis* sp.), crown vetch (*Vicia* sp.), hairy vetch, adzuki bean, lupine (*Lupinus* sp.), *trifolium*, common bean (*Phaseolus* sp.), field bean (*Pisum* sp.), clover (*Melilotus* sp.) *Lotus*, trefoil, lens, and false indigo.

Examples of suitable forage and turf grass include, without limitation, alfalfa (*Medicago* s sp.), orchard grass, tall fescue, perennial ryegrass, creeping bent grass, and redtop.

Examples of suitable crop plants and model plants include, without limitation, *Arabidopsis*, corn, rice, alfalfa, sunflower, canola, soybean, cotton, peanut, *sorghum*, wheat, tobacco, and *lemna*.

The plants of the present disclosure may be genetically modified in that recombinant nucleic acids have been introduced into the plants, and as such the genetically modified plants do not occur in nature. A suitable plant of the present disclosure is one capable of expressing a transgene of interest containing a P5SM element of the present disclosure.

As used herein, the terms "transgenic plant" and "genetically modified plant" are used interchangeably and refer to a plant that contains within its genome a recombinant nucleic acid. Generally, the recombinant nucleic acid is stably integrated within the genome such that the polynucleotide is passed on to successive generations. However, in certain embodiments, the recombinant nucleic acid is transiently expressed in the plant. The recombinant nucleic acid may be integrated into the genome alone or as part of a recombinant expression cassette. "Transgenic" is used herein to include any cell, cell line, callus, tissue, plant part or plant, the genotype of which has been altered by the presence of exogenous nucleic acid including those transgenics initially so altered as well as those created by sexual crosses or asexual propagation from the initial transgenic.

Expression of P5SM-Regulated Transgenes in Plants

Transgenes containing a P5SM element of the present disclosure may be introduced into plant cells via any suitable methods known in the art. For example, a vector containing a transgenes containing a P5SM element of the present disclosure can be expressed in a plant with any suitable plant expression vector. Typical vectors useful for expression of recombinant nucleic acids in higher plants are well known in the art and include, without limitation, vectors derived from the tumor-inducing (Ti) plasmid of *Agrobacterium tumefaciens* (e.g., see Rogers et al., *Meth. in Enzymol.* (1987) 153:253-277). These vectors are plant integrating vectors in that on transformation, the vectors integrate a portion of vector DNA into the genome of the host plant. Exemplary *A. tumefaciens* vectors useful herein are plasmids pKYLX6 and pKYLX7 (e.g., see of Schardl et al., *Gene* (1987) 61:1-11; and Berger et al., *Proc. Natl. Acad. Sci. USA* (1989) 86:8402-8406); and plasmid pBI 101.2 that is available from Clontech Laboratories, Inc. (Palo Alto, Calif.). The vectors are operably linked to any of plant promoters known in the art or described above in the section entitled "Vectors and Host Cells of the Present Disclosure."

Plant transformation protocols as well as protocols for introducing vectors of the present disclosure containing a P5SM-regulated transgene into plants may vary depending on the type of plant or plant cell, e.g., monocot or dicot, targeted for transformation. Suitable methods of introducing vectors of the present disclosure into plant cells and subsequent insertion into the plant genome include, without limitation, microinjection (Crossway et al., *Biotechniques* (1986) 4:320-334), electroporation (Riggs et al., *Proc. Natl. Acad. Sci. USA* (1986) 83:5602-5606), *Agrobacterium*-mediated transformation (U.S. Pat. No. 5,563,055), direct gene transfer (Paszkowski et al., *EMBO J.* (1984) 3:2717-2722), and ballistic particle acceleration (U.S. Pat. No. 4,945,050; Tomes et al. (1995). "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al., *Biotechnology* (1988) 6:923-926).

Additionally, vectors of the present disclosure containing a P5SM-regulated transgene can be targeted to a specific organelle within a plant cell. Targeting can be achieved by providing the vectors with an appropriate targeting peptide sequence. Examples of such targeting peptides include, without limitation, secretory signal peptides (for secretion or cell wall or membrane targeting), plastid transit peptides, chloroplast transit peptides, mitochondrial target peptides, vacuole targeting peptides, nuclear targeting peptides, and the like (e.g., see Reiss et al., *Mol. Gen. Genet.* (1987) 209(1):116-121; Settles and Martienssen, *Trends Cell Biol* (1998) 12:494-501; Scott et al., *J Biol Chem* (2000) 10:1074; and Luque and Correas, *J Cell Sci* (2000) 113:2485-2495).

The modified plant may be grown into plants in accordance with conventional ways (e.g., see McCormick et al., *Plant Cell. Reports* (1986) 81-84.). These plants may then be grown, and pollinated with either the same transformed strain or different strains, with the resulting hybrid having the desired phenotypic characteristic. Two or more generations may be grown to ensure that the subject phenotypic characteristic is stably maintained and inherited and then seeds harvested to ensure the desired phenotype or other property has been achieved.

In addition, seed of the transgenic plant may also be obtained by any method known in the art for obtaining seed.

Methods of Regulating Gene Expression

Certain aspects of the present disclosure relate to methods of regulating expression of one or more transgenes in a eukaryotic cell or plant by utilizing P5SM elements of the present disclosure to regulate the expression of the transgene by alternative splicing. In one aspect, the present disclosure provides a method of regulating transgene expression in a eukaryotic cell, by providing a eukaryotic cell containing a first vector and a second vector, where the first vector is the vector of any of the above embodiments, and the second vector contains a recombinant polynucleotide encoding an L5 ribosomal protein, where the second vector is operably linked to an inducible promoter sequence; culturing the eukaryotic cell under conditions whereby the first vector is expressed to produce mRNA comprising the P5SM; and inducing expression of the L5 ribosomal protein in the eukaryotic cell, where the L5 ribosomal protein induces excision of the P5SM from the mRNA, thereby allowing transgene protein expression. The eukaryotic cell may be a fungal cell, a yeast cell, a plant cell, an insect cell, or a mammalian cell. In another aspect, the present disclosure provides a method of regulating transgene expression in a plant, by providing a plant containing a first vector and a second vector, where the first vector is the vector of any of the above embodiments, and the second vector contains a recombinant polynucleotide encoding an L5 ribosomal protein, where the second vector is operably linked to an inducible promoter sequence; growing the plant under conditions whereby the first vector is expressed to produce mRNA comprising the P5SM; and inducing the expression of the L5 ribosomal protein in the plant, where the L5 ribosomal protein induces excision of the P5SM from the mRNA, thereby allowing transgene protein expression.

Culturing or growing conditions sufficient for the expression of the vector containing the transgene having the P5SM element and for the induction of the L5 ribosomal protein are well known in the art and include any suitable culturing or growing conditions disclosed herein. In certain embodiments, expression of the transgene is inhibited by the presence of the P5SM. In other embodiments, the L5 ribosomal protein is derived from monocotyledonous plant species, such as *Oryza sativa*. In further embodiments, the L5 ribosomal protein is a transgenic L5 ribosomal protein.

In another aspect, the present disclosure provides a method of regulating transgene expression in a eukaryotic cell, by providing a eukaryotic cell containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; culturing the eukaryotic cell under conditions whereby the vector is expressed to produce mRNA comprising the modified P5SM and the nucleotide aptamer; and adding a chemical inducer to the eukaryotic cell, where the chemical inducer binds the nucleotide aptamer resulting in excision of the modified P5SM from the mRNA, thereby allowing transgene protein expression. The eukaryotic cell may be a fungal cell, a yeast cell, a plant cell, an insect cell, or a mammalian cell. In a further aspect, the present disclosure provides a method of regulating transgene expression in a plant, by providing a plant containing the vector of any of the above embodiments, where the vector contains a modified P5SM that is incapable of binding to an L5 ribosomal protein and excising from a gene transcript in response to L5 ribosomal protein binding when the modified P5SM is incorporated into a gene in a host organism; growing the plant under conditions whereby the vector is expressed to produce mRNA comprising the modified P5SM and the nucleotide aptamer; and adding a chemical inducer to the plant, where the chemical inducer binds the nucleotide aptamer resulting in excision of the modified P5SM from the mRNA, thereby allowing transgene protein expression. Culturing or growing conditions sufficient for the expression of the vector containing the transgene having the modified P5SM element are well known in the art and include any suitable culturing or growing conditions disclosed herein. In certain embodiments, transgene protein expression is inhibited by the presence of the modified P5SM. In other embodiments, the chemical inducer is theophylline or tetracycline In another aspect, the present disclosure provides a method of regulating transgene expression in a eukaryotic cell, by providing a eukaryotic cell containing the vector of any of the above embodiments, where the vector contains a modified P5SM that is incapable of responding to an L5 ribosomal protein resulting in constitutive excision from a gene transcript when the modified P5SM is incorporated into a gene in a host organism; culturing the eukaryotic cell under conditions whereby the vector is expressed to produce mRNA comprising the modified P5SM and the nucleotide aptamer; and adding a chemical inducer to the eukaryotic cell, where the chemical inducer binds the nucleotide aptamer resulting in inhibition of P5SM excision from the mRNA, thereby inhibiting transgene protein expression. The eukaryotic cell may be a fungal cell, a yeast cell, a plant cell, an insect cell, or a mammalian cell. The present disclosure also relates to methods of regulating transgene expression in a plant, by providing a plant containing the vector of any of the above embodiments, where the vector contains a modified P5SM that is incapable of responding to an L5 ribosomal protein resulting in constitutive excision from a gene transcript when the modified P5SM is incorporated into a gene in a host organism; growing the plant under conditions whereby the vector is expressed to produce mRNA comprising the modified P5SM and the nucleotide aptamer; and adding a chemical inducer to the plant, where the chemical inducer binds the nucleotide aptamer resulting in inhibition of P5SM excision from the mRNA, thereby inhibiting transgene protein expression. Culturing or growing conditions sufficient for the expression of the vector containing the transgene having the modified P5SM element are well known in the art and include any suitable culturing or growing conditions disclosed herein. In certain embodiments, the chemical inducer is theophylline or tetracycline It is to be understood that while the present disclosure has been described in conjunction with the preferred specific embodiments thereof, the foregoing description is intended to illustrate and not limit the scope of the present disclosure. Other aspects, advantages, and modifications within the scope of the present disclosure will be apparent to those skilled in the art to which the present disclosure pertains.

The following examples are offered to illustrate provided embodiments and are not intended to limit the scope of the present disclosure.

EXAMPLES

Example 1

The following Example relates to the characterization of a natural splicing cassette containing a plant 5S rRNA mimic (P5SM) suicide exon, and an engineered splicing cassette containing a hybrid P5SM (HyP5SM) suicide exon as regulators of gene expression.
Materials and Methods
Oligonucleotides and DNA Constructs Sequences of all synthetic primers used for making and mutagenizing DNA constructs, performing overlap extension PCR, RT-PCR, and RT-qPCR are described in Table 1. TFIIIA-eGFP (formerly called Pre-EGFP), LUC (used as a control except when assaying the fLUC reporter), AtL5, and DsRed2 constructs were described previously (23). The coding sequence of OsL5 (Os01g0896800) also was previously isolated and cloned into the pBinAR vector (23). The fLUC coding sequence was derived from the pGL3 vector (Promega). *Arabidopsis thaliana* coding sequences were amplified by PCR from cDNA (see RNA isolation methods) and cloned using the TOPO TA Cloning kit (Invitrogen). Mutations to TFIIIA-eGFP were made using the QuikChange II Site-Directed Mutagenesis (Stratagene) or QuikChange Lightning Site-Directed Mutagenesis kits (Stratagene) according to the manufacturer's instructions.

The P5SM splicing cassette sequence was inserted into constructs by overlap extension PCR (24). Briefly, the coding sequence to be modified was amplified as two DNA fragments using PCR primers that introduce a region that overlaps with the sequence of the P5SM splicing cassette. For the front fragment, the overlapping region is at the 3' end, and for the back fragment, the overlapping region is at the 5' end. The P5SM splicing cassette was amplified by PCR using TFIIIA-eGFP as the DNA template, generating a third DNA fragment. The DNA fragments were purified by agarose gel electrophoresis and then mixed in a 1:1:1 ratio as partial templates for overlap extension PCR, which uses forward and reverse primers that anneal to the 5' and 3' ends of the desired full-length construct. The PCR product containing the P5SM cassette was purified by agarose gel electrophoresis before being cloned into the TOPO vector for sequence confirmation. To generate constructs for use in plant infiltration experiments, they were re-amplified to introduce restriction sites at the ends (see Table 1), digested with the appropriate restriction enzymes, and ligated using T4 DNA ligase (NEB) into the binary vector pBinAR (25).

The sequence encoding the P5SM RNA element from *O. sativa* was derived from the genomic fragment of Os02g0116000 previously cloned into the TOPO vector (23). To generate the eGFP-OsP5SM construct, overlap extension PCR was performed to insert OsP5SM in place of the original P5SM from *A. thaliana*. To generate eGFP-HyP5SM, the purine-rich insertion was introduced directly into the primers used to amplify eGFP-OsP5SM as two DNA fragments, then the two overlapping pieces were extended by PCR. After sequence confirmation of these constructs in the TOPO vector, they were cloned into pBinAR as described above.

Leaf-Based Fluorescence Assay

In vivo reporter fluorescence assays were performed by Agrobacterium-mediated leaf infiltration in Nicotiana benthamiana as previously described (19). Briefly, each leaf half was infiltrated with a 1:1:1 mixture of Agrobacterium transformed with pBinAR plasmids carrying the reporter construct, inducer (AtL5 or OsL5) or the control (LUC), and DsRed2 as a normalization standard. For assaying the fLUC reporter, untransformed Agrobacterium was used as the control instead. In vivo fluorescence was measured 3 days post infiltration using the Typhoon laser-based scanning system (GE Healthcare) using excitation and emission wavelength settings of 488 nm/520 nm for eGFP and 532 nm/580 nm for DsRed2. The ratios of eGFP/DsRed2 fluorescence readings were taken for each leaf half in order to normalize differences in transformation efficiency. On average, ~15% difference was observed between DsRed2 fluorescence for leaf halves from the same leaf sample.

To calculate relative fold induction by AtL5 or OsL5, the eGFP/DsRed2 ratio for the leaf half co-expressing the inducer was divided by the other half co-expressing the control. The average relative fold induction was calculated from these values for several leaf samples, and the number of independent leaf samples analyzed (n) and standard deviations are as indicated. No more than two leaf samples were analyzed from the same plant. Autofluorescence (defined as fluorescence measured for uninfiltrated, or "blank", leaves) was not measured, and so was not subtracted from the eGFP fluorescence readings for all experiments except for the one showing relative fluorescence of HyP5SM without DsRed2. For this experiment, autofluorescence was measured and subtracted from the eGFP fluorescence readings of both leaf halves, and fold induction for each individual leaf was calculated by taking the ratio of the half co-expressing OsL5 versus the other co-expressing LUC (control).

RNA Isolation and RT-PCR Analyses

Total RNA was isolated from ~100 mg N. benthamiana leaf tissue collected 2 days post infiltration using the Universal RNA Purification Kit (CHIMERX) according to the manufacturer's instructions. Leaf tissue samples were immediately frozen in liquid nitrogen after being placed in microtubes, then pulverized using a bead mill (TissueLyser, Qiagen) prior to RNA extraction. The samples were kept frozen during the milling process by being placed in an adapter rack that was pre-chilled at −80° C. The entire procedure was performed as quickly as possible, and the integrity of the RNA after isolation was checked by analysis on an agarose gel.

cDNA was generated from ~1 ng RNA samples that had been treated with RQ1 DNase (Promega) using iSCRIPT reverse transcriptase (Bio-rad) and oligo d(T) primers following the manufacturer's instructions. Spliced products were amplified from cDNA samples by PCR with Taq polymerase (NEB) using target-specific primers (Table 1).

In Table 1, lowercase nucleotides represent random nucleotides; bolded lowercase nucleotides represent restriction sites; uppercase nucleotides represent primer sequences; and bolded and italicized uppercase nucleotides represent overlap with P5SM element.

TABLE 1

Sequence of DNA Primers

| NAME | EXPERIMENT | SEQ ID NO | R.E. USED |
|---|---|---|---|
| | RT-PCR analysis | | |
| | TFIIIA-eGFP | | |
| DNA1 | 5'- atgcggatccGTGCGGCGTCTTGATGGA | 41 | For, BamHI |
| DNA2 | 5'- agcttctagaATCCACATAGCAAGTAAAAGA | 42 | Rev, XbaI |
| | eGFP-P5SME/R; eGFP-*Os*P5SME/R; eGFP-*Hy*P5SME/R | | |
| DNA3 | 5'- CACCCTGACCTACGGCGT | 43 | For |
| DNA4 | 5'- CGATGCCCTTCAGCTCG | 44 | Rev |
| | fLUC-P5SME/R | | |
| DNA5 | 5'- GACATCACTTACGCTGAGTACT | 45 | For |
| DNA6 | 5'- TGCAACCCCTTTTTGGAAAC | 46 | Rev |
| | fLUC-P5SMK/R | | |
| DNA7 | 5'- CATAAAGAAAGGCCCGGC | 47 | For |
| DNA8 | 5'- ACTGCAACTCCGATAAATAACG | 48 | Rev |
| | CYP707A3-P5SME/R | | |
| DNA9 | 5'- ACCCTAATGTGTTCTTTGCAGCAA | 49 | For |
| DNA10 | 5'- TTGAGTTCCATCCCAAGAATTGA | 50 | Rev |
| | CYP707A3-P5SME/S | | |
| DNA11 | 5'- GATGATCTCGAGCCCTGAAG | 51 | For |
| DNA12 | 5'- AACCTTTCTCTAGAATGTAGTAGCA | 52 | Rev |
| | CYP707A3-P5SMK/R | | |
| DNA13 | 5'- TGCCTGATGCAATCAGAAACATGGT | 53 | For |
| DNA14 | 5'- AGGAGATCTGTGTGTGATGATGGGT | 54 | Rev |

TABLE 1-continued

Sequence of DNA Primers

| NAME | EXPERIMENT | SEQ ID NO | R.E. USED |
|------|------------|-----------|-----------|
| | PSY-P5SME/R; PSY-P5SMC/R | | |
| DNA15 | 5'- CTTGATGTGAAGAAACCACAAGATG | 55 | For |
| DNA16 | 5'- AAGCATATCGAAAGGACGACCA | 56 | Rev |
| | NCED3-P5SME/R | | |
| DNA17 | 5'- AACTTCCCGATTCCATCAAAGG | 57 | For |
| DNA18 | 5'- AAATAGACCAAACCGGCGTTAG | 58 | Rev |
| | CYP707A2-P5SME/R | | |
| DNA19 | 5'- ACACTCCGCCTCTACACAGAAAAT | 59 | For |
| DNA20 | 5'- TTTCATGTATTCGAGGGTGTTGAT | 60 | Rev |
| | qRT-PCR analysis | | |
| | eGFP-P5SME/R transcripts retaining exon (SP-II) | | |
| DNA21 | 5'- CGTCCAGGAGAGAACCATCTTC | 61 | For |
| DNA22 | 5'- CTGCTTGTCGGCCATGATATAG | 62 | Rev |
| | eGFP-P5SME/R transcripts skipping exon (SP-I) | | |
| DNA23 | 5'- CGTCCAGGAGGAAATAAATAGCC | 63 | For |
| DNA24 | 5'- CTTGAAGAAGATGGTTCTCTCAAACA | 64 | Rev |
| | fLUC-P5SME/R transcripts retaining exon (SP-II) | | |
| DNA5 | 5'- GACATCACTTACGCTGAGTACT | 65 | For |
| DNA25 | 5'- GGCTATTTATTTCCTCATTATAAATGTC | 66 | Rev |
| DNA26 | 5'- CGACATTTATAATGAGGAAATAAATAGCC | 67 | For2 |
| DNA27 | 5'- CAATTCTCTCTCAAACATTTTGCG | 68 | Rev2 |
| DNA28 | 5'- CAAAATGTTTGAGAGAGAATTGCTC | 69 | For3 |
| DNA29 | 5'- GAGGTAGATGAGATGTGACGA | 70 | Rev3 |
| | fLUC-P5SME/R transcripts skipping exon (SP-I) | | |
| DNA5 | 5'- GACATCACTTACGCTGAGTACT | 71 | For |
| DNA30 | 5'- TTGAGCAATTCTCTCTCATTATAAATG | 72 | Rev |
| DNA31 | 5'- CGACATTTATAATGAGAGAGAATTGC | 73 | For2 |
| DNA32 | 5'- GTAGATGAGATGTGACGAACGT | 74 | Rev2 |
| | fLUC-P5SMK/R transcripts retaining exon (SP-II) | | |
| DNA7 | 5'- CATAAAGAAAGGCCCGGC | 75 | For |
| DNA33 | 5'- GGCTATTTATTTCCTTCATAGCTTCT | 76 | Rev |
| | fLUC-P5SMK/R transcripts skipping exon (SP-I) | | |
| DNA7 | 5'- CATAAAGAAAGGCCCGGC | 77 | For |
| DNA34 | 5'- CAGCCCATATCTCTTCATAGCTT | 78 | Rev |
| | DsRED transcripts (reference) | | |
| DNA35 | 5'- CCGAGAACGTCATCACCG | 79 | For |
| DNA36 | 5'- CTTGGAGCCGTACTGGAACTG | 80 | Rev |
| | Cloning of reporter constructs | | |
| | P5SM insert | | |
| DNA37 | 5'- GTAGATTTATGCATCCTCTTGTCATGAG | 81 | For |
| DNA38 | 5'- CTACACACCAAAAGAGTGAAAACCAT | 82 | Rev |
| | eGFP-P5SME/R 3-piece ligation | | |
| DNA39 | 5'- gacagatctATGTCTAGAGTGAGCAAGGGCG (5'- eGFP) | 83 | For, BglII |
| DNA40 | 5'- CTCATGACAAGAGGATGCATAAATCTAC CTCCTGGACGTAGCCTTCGG (5'- P5SM overlap) | 84 | Rev |
| DNA41 | 5'- ATGGTTTTCACTCTTTTGGTGTGTAG AGAACCATCTTCTTCAAGGACGAC (3'- P5SM overlap) | 85 | For |
| DNA42 | 5'- gacgtcgacTTACTTGTACAGCTCGTCCATGC (3'- eGFP) | 86 | Rev, SalI |

TABLE 1-continued

Sequence of DNA Primers

| NAME | EXPERIMENT | SEQ ID NO | R.E. USED |
|---|---|---|---|
| | fLUC-P5SME/R 3-piece ligation | | |
| DNA43 | 5'- acgtagatctATGGAAGACGCCAAAAACATAA (5'- fLUC) | 87 | For, BglII |
| DNA44 | 5'- CTCATGACAAGAGGATGCATAAATCTACCTCATTATAAATGTCGTTCGCGG (5'- P5SM overlap) | 88 | Rev |
| DNA45 | 5'- ATGGTTTTCACTCTTTTGGTGTGTAGAGAGAATTGCTCAACAGTATGGC (3'- P5SM overlap) | 89 | For |
| DNA46 | 5'- acgtgtcgacTTACACGGCGATCTTTCCG (3'- fLUC) | 90 | Rev, SalI |
| | fLUC-P5SMK/R 3-piece ligation | | |
| DNA43 | 5'- acgtagatctATGGAAGACGCCAAAAACATAA (5'- fLUC) | 91 | For, BglII |
| DNA47 | 5'- CTCATGACAAGAGGATGCATAAATCTACCTTCATAGCTTCTGCCAACCG (5'- P5SM overlap) | 92 | Rev |
| DNA48 | 5'-ATGGTTTTCACTCTTTTGGTGTGTAGAGATATGGGCTGAATACAAATCACAG (3'- P5SM overlap) | 93 | For |
| DNA46 | 5'- acgtgtcgacTTACACGGCGATCTTTCCG (3'- fLUC) | 94 | Rev, SalI |
| | NCED3-P5SME/R 3-piece ligation | | |
| DNA49 | 5'- tgatagatctATGGCTTCTTTCACGGCAAC (5'- NCED3) | 95 | For, BglII |
| DNA50 | 5'- CTCATGACAAGAGGATGCATAAATCTACCTCCTGAACAAACCGGTTAGTCTG (5'- P5SM overlap) | 96 | Rev |
| DNA51 | 5'- ATGGTTTTCACTCTTTTGGTGTGTAGAGACAATTGGGTCGACCGGTTT (3'- P5SM overlap) | 97 | For |
| DNA52 | 5'- atcactcgagGAACTCACACGACCTGCTTCG (3'- NCED3) | 98 | Rev, XhoI |
| | CYP707A3-P5SME/R 3-piece ligation | | |
| DNA53 | 5'- tgattgatcaATGGATTTCTCCGGTTTGTTTC (5'-CYP707A3) | 99 | For, BclI |
| DNA54 | 5'- CTCATGACAAGAGGATGCATAAATCTACCTCTTTACTGGCCGGAAAAGTC (5'- P5SM overlap) | 100 | Rev |
| DNA55 | 5'- ATGGTTTTCACTCTTTTGGTGTGTAGAGAATGCTTGGAAAACAAGCC (3'- P5SM overlap) | 101 | For |
| DNA56 | 5'- atcagtcgacCTATGGTTTTCGTTCCAAGGC (3'- CYP707A3) | 102 | Rev, SalI |
| | CYP707A2-P5SME/R 3-piece ligation | | |
| DNA57 | 5'- tgatagatctATGCAAATCTCATCTTCATCGTC (5'- CYP707A2) | 103 | For, BglII |
| DNA58 | 5'- CTCATGACAAGAGGATGCATAAATCTACCTCTTTGCTTGGAGGATAAGTTGG (5'- P5SM overlap) | 104 | Rev |
| DNA59 | 5'- ATGGTTTTCACTCTTTTGGTGTGTAGAGAATGATTGGACCAGAGGCTC (3'- P5SM overlap) | 105 | For |
| DNA60 | 5'- atcagtcgacCTTAAATCGGGGTTACTCTTATTGG (3'- CYP707A2) | 106 | Rev, SalI |
| | PSY-P5SME/R 3-piece ligation | | |
| DNA61 | 5'- tgattgatcaATGTCTTCTTCTGTAGCAGTGTTATGG (5'- PSY) | 107 | For, BclI |
| DNA62 | 5'- CTCATGACAAGAGGATGCATAAATCTACCTCGGGTGTCATAAGCAAAGTTC (5'- P5SM overlap) | 108 | Rev |
| DNA63 | 5'- ATGGTTTTCACTCTTTTGGTGTGTAGAGACGAAAGGCGATTTGGG (3'- P5SM overlap) | 109 | For |
| DNA64 | 5'- atcagtcgacCGCTCTCATATCGATAGTCTTGAAC (3'- PSY) | 110 | Rev, SalI |
| | CYP707A3-P5SME/S 3-piece ligation | | |
| DNA53 | 5'- tgattgatcaATGGATTTCTCCGGTTTGTTTC (5'-CYP707A3) | 111 | For, BclI |
| DNA65 | 5'- CTCATGACAAGAGGATGCATAAATCTACCTCAATGTGAGGGACCATGTTTCTGATTGC (5'- P5SM overlap) | 112 | Rev |
| DNA66 | 5'- ATGGTTTTCACTCTTTTGGTGTGTAGAGTATTGCTCAAGAATCACTCAATTCTTGGGAT (3'- P5SM overlap) | 113 | For |
| DNA56 | 5'- atcagtcgacCTATGGTTTTCGTTCCAAGGC (3'- CYP707A3) | 114 | Rev, SalI |
| | CYP707A3-P5SMK/R 3-piece ligation | | |
| DNA53 | 5'- tgattgatcaATGGATTTCTCCGGTTTGTTTC (5'-CYP707A3) | 115 | For, BclI |
| DNA67 | 5'- CTCATGACAAGAGGATGCATAAATCTACCTTTAGATCTTCTCGGTAATAAACTTCGTCTT (5'- P5SM overlap) | 116 | Rev |

TABLE 1-continued

Sequence of DNA Primers

| NAME | EXPERIMENT | SEQ ID NO | R.E. USED |
|---|---|---|---|
| DNA68 | 5'- ATGGTTTTCACTCTTTTGGTGTGTAGAGATGCTACTACATTCTAGAGAAAGGTTACAATT (3'-P5SM overlap) | 117 | For |
| DNA56 | 5'- atcagtcgacCTATGGTTTTCGTTCCAAGGC (3'- CYP707A3) | 118 | Rev, SalI |

PSY-P5SMC/R 3-piece ligation

| DNA61 | 5'- tgattgatcaATGTCTTCTTCTGTAGCAGTGTTATGG (5'- PSY) | 119 | For, BclI |
| DNA69 | 5'- CTCATGACAAGAGGATGCATAAATCTACGCACCAAACGTAGATTGCCCA (5'- P5SM overlap) | 120 | Rev |
| DNA70 | 5'- ATGGTTTTCACTCTTTTGGTGTGTAGAGAAGAACTGATGAACTTGTGGAT (3'- P5SM overlap) | 121 | For |
| DNA64 | 5'- atcagtcgacCGCTCTCATATCGATAGTCTTGAAC (3'- PSY) | 122 | Rev, SalI | eGFP- OsP5SM 3-piece ligation

| DNA39 | 5'- gacagatctATGTCTAGAGTGAGCAAGGGCG (5'- eGFP) | 123 | For, BglII |
| | 5'- TGGGATCCAATGCTTCACACTAACATAGGTAAGACCTTTTGATTTAAACAAAAG (overhang 5'- P5SM and OsP5SM P1) | 124 | Rev |
| DNA71 | 5'- GTGTGAAGCATTGGATCCCA (OsP5SM P1 insert) | 125 | For |
| DNA72 | 5'- GCGTGAGGAGGCAATCCTG (OsP5SM P1 insert) | 126 | Rev |
| DNA73 | 5'- CAGGATTGCCTCCTCACGCAATGTTTGAGGTCTGATGTTCAATAGC (overhang 3'- P5SM and OsP5SM P1) | 127 | For |
| DNA42 | 5'- gacgtcgacTTACTTGTACAGCTCGTCCATGC (3'- eGFP) | 128 | Rev, SalI | eGFP- HyP5SM 3-piece ligation

| DNA39 | 5'- gacagatctATGTCTAGAGTGAGCAAGGGCG (5'- eGFP) | 129 | For, BglII |
| DNA74 | 5'- TTTTGGAGTTCTCTCTTTGGGATCCAA (OsP5SM L2 mutation) | 130 | Rev |
| DNA75 | 5'- GGCATTGGATCCCAAAGAGAGAACTC (OsP5SM L2 mutation) | 131 | For |
| DNA42 | 5'- gacgtcgacTTACTTGTACAGCTCGTCCATGC (3'- eGFP) | 132 | Rev, SalI |

P5SM mutant constructs by QuikChange mutagenesis

M1

| DNA76 | 5'-TATGCAGAGTCATTCGCTCAAGGTAGATTTATGCATCCTCTTG | 133 | For |
| DNA77 | 5'-CAAGAGGATGCATAAATCTACCTTGAGCGAATGACTCTGCATA | 134 | Rev |

M2

| DNA78 | 5'-TATGCAGAGTCATTCGCTCCAGGTAGATTTATGCATCCTCTTG | 135 | For |
| DNA79 | 5'-CAAGAGGATGCATAAATCTACCTGGAGCGAATGACTCTGCATA | 136 | Rev |

M3

| DNA80 | 5'-ATATGCAGAGTCATTCGCTCGTGGTAGATTTATGCATCCTCTT | 137 | For |
| DNA81 | 5'-AAGAGGATGCATAAATCTACCACGAGCGAATGACTCTGCATAT | 138 | Rev |

M4

| DNA82 | 5'-ATATGCAGAGTCATTCGCTCGCGGTAGATTTATGCATCCTCTT | 139 | For |
| DNA83 | 5'-AAGAGGATGCATAAATCTACCGCGAGCGAATGACTCTGCATAT | 140 | Rev |

M5

| DNA84 | 5'-ATATGCAGAGTCATTCGCTCGGGGTAGATTTATGCATCCTCTT | 141 | For |
| DNA85 | 5'-AAGAGGATGCATAAATCTACCCCGAGCGAATGACTCTGCATAT | 142 | Rev |

M6

| DNA86 | 5'-CATATGCAGAGTCATTCGCTCTTGGTAGATTTATGCATCCTCTTG | 143 | For |

TABLE 1-continued

Sequence of DNA Primers

| NAME | EXPERIMENT | SEQ ID NO | R.E. USED |
|---|---|---|---|
| DNA87 | 5'-CAAGAGGATGCATAAATCTACCAAGAGCGAATGACTCTGCATATG | 144 | Rev |
| | M7 | | |
| DNA88 | 5'-CATATGCAGAGTCATTCGCTCTCGGTAGATTTATGCATCCTCTTG | 145 | For |
| DNA89 | 5'-CAAGAGGATGCATAAATCTACCGAGAGCGAATGACTCTGCATATG | 146 | Rev |
| | M8 | | |
| DNA90 | 5'-CATATGCAGAGTCATTCGCTCTGCGTAGATTTATGCATCCTCTTG | 147 | For |
| DNA91 | 5'-CAAGAGGATGCATAAATCTACGCAGAGCGAATGACTCTGCATATG | 148 | Rev |
| | M9; M14 | | |
| DNA92 | 5'- TTTCACTCTTTTGGTGTGTAGAGTTCTTTTACTTGCTATGTGG | 149 | For |
| DNA93 | 5'-CCACATAGCAAGTAAAAGAACTCTACACACCAAAAGAGTGAAA | 150 | Rev |
| | M10 | | |
| DNA94 | 5'- TTTCACTCTTTTGGTGTGTAGAGCTCTTTTACTTGCTATGTGG | 151 | For |
| DNA95 | 5'-CCACATAGCAAGTAAAAGAGCTCTACACACCAAAAGAGTGAAA | 152 | Rev |
| | M11 | | |
| DNA96 | 5'-GTTTTCACTCTTTTGGTGTGTAGGTATCTTTTACTTGCTATGTGG | 153 | For |
| DNA97 | 5'-CCACATAGCAAGTAAAAGATACCTACACACCAAAAGAGTGAAAAC | 154 | Rev |
| | M12 | | |
| DNA98 | 5'-GTTTTCACTCTTTTGGTGTGTAGCCATCTTTTACTTGCTATGTGG | 155 | For |
| DNA99 | 5'-CCACATAGCAAGTAAAAGATGGCTACACACCAAAAGAGTGAAAAC | 156 | Rev |
| | M15; M17 | | |
| DNA100 | 5'-GTTTTCACTCTTTTGGTGTGTAGCTATCTTTTACTTGCTATGTGG | 157 | For |
| DNA101 | 5'-CCACATAGCAAGTAAAAGATAGCTACACACCAAAAGAGTGAAAAC | 158 | Rev |

Spliced products were visualized by agarose gel electrophoresis and confirmed by sequencing after gel purification and TOPO cloning. RT-qPCR analysis was performed on the Bio-Rad CFX96 instrument using spliced product-specific primers (see Table 1) and SsoFast EvaGreen Supermix (Bio-Rad). The specificity of spliced product amplification was confirmed by melting curve analysis and visualization of PCR products on an agarose gel. Control samples in which no reverse transcriptase was added to the reaction also were analyzed after PCR to confirm the absence of DNA contamination. Transcript abundances for different samples were calculated using standard curves determined for each target. Primer efficiencies were determined to be within the range of 100±5%. Relative transcript amounts were normalized to the relative amount of DsRed2 transcript and the sample with the control LUC was set to 1. For biological replicates, no more than two leaf samples were taken from the same plan.

Luciferase Assay

Firefly luciferase enzyme activity was measured using the Luciferase Assay System (Promega) according to the manufacturer's instructions. N. benthamiana leaf tissue samples were collected and analyzed 3 days post infiltration. Tissue lysate samples were normalized to total protein content determined by Bradford assay, and relative luminescence was measured in triplicate using a GloMax 96 Microplate Luminometer (Promega). Fold induction was determined relative to samples without co-expression of inducer.

Bioinformatics

The TAIR9 release of 33,201 annotated protein coding sequences for *A. thaliana* was inputted into a MySQL database table. A database query was made for each pair of amino acids (corresponding to the bordering codons) within the first half of protein coding sequences. Next, a database query was made counting the number of protein entries not containing any of the amino acid pairs within the first half of the coding sequence. This number was subtracted from and divided by the total number of protein coding sequences to calculate the proteome coverage percentage. Similar queries were used to calculate the percentage of protein entries containing an E, K, or Q amino acid within the first half of the coding sequence.

Western Blots

Crude protein was extracted from ~100 mg *N. benthamiana* leaf tissue collected 2 days post infiltration as previously described (23). After centrifugation, the total protein concentration of the supernatant was determined using the Coomassie Plus Protein Assay (Pierce) following standard protocols. ~2 μg of total protein for each sample was loaded and run on an SDS-PAGE gel along with a pre-stained molecular weight marker. Semi-dry transfer to the PVDF membrane (Millipore) was performed following standard procedures using an Owl HEP-1 electroblotter. After overnight incubation with SuperBlock blocking buffer (Pierce) with 1% Tween-20, the membrane was probed with 1:20,000 anti-GFP (Millipore) in SuperBlock for 1 hr. Following three washes with TBST (TBS with 0.1% Tween-20), the membrane was incubated with 1:10,000 goat anti-mouse HRP conjugate (Pierce) in SuperBlock for 1 hr. After three more washes with TBST, protein was detected using the SuperSignal West Pico chemiluminescent substrate (Pierce) following standard procedures. Shown is the film image after a 20 min exposure. The membrane was subsequently incubated with GelCode Blue reagent (Pierce) for 5 min before destaining following standard procedures.

Results

Figure 3:
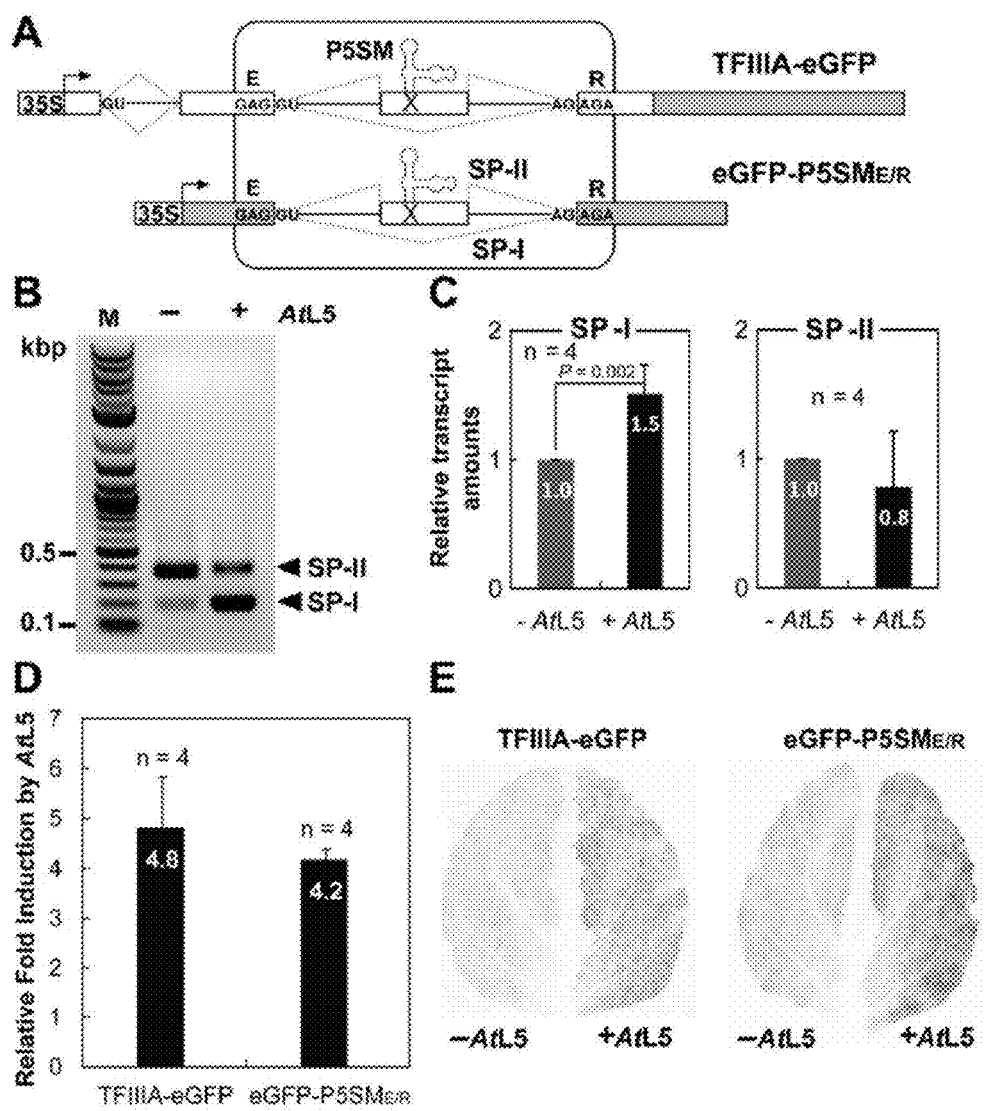
FIG. 3 shows that the P5SM splicing cassette functions in the eGFP coding sequence.

A Natural Splicing Cassette Bearing a Suicide Exon can be Employed to Regulate Other Genes We and others have previously reported the discovery of the plant 5S rRNA mimic (P5SM), an RNA element residing within a highly conserved, alternatively spliced suicide exon that controls expression of transcription factor IIIA (TFIIIA) in land plants (23, 26). We have shown that TFIIIA expression is activated by skipping of the suicide exon, which is induced by ribosomal protein L5 binding to the P5SM RNA element (23). Our initial design for a splicing cassette conservatively included not only the P5SM exon (175 nt in length) and flanking intronic regions (150 and 98 nt in length) from the *Arabidopsis thaliana* TFIIIA gene, but also the two bordering codons, which encode amino acids Glu (E) and Arg (R), respectively (FIG. 3A). This design was intended to balance preserving the relative splice site strengths, in case they were important for alternative splicing activity, with minimizing the gene context requirements.

Using the overlap extension PCR method (24), the above splicing cassette, called P5SM$_{E/R}$, was inserted in place of the codons for E-96 and R-97 within the coding sequence for enhanced green fluorescent protein to generate the reporter construct eGFP-P5SM$_{E/R}$ (FIG. 3A). Thus, outside of the inserted cassette, the only change to the coding sequence of eGFP was a silent mutation of codon 97 from CGC to AGA (both encode Arg). This codon was changed in order to match the sequence surrounding the 3' splice site in TFIIIA.

The function of the splicing cassette in this non-native gene context was compared to that for the control construct, TFIIIA-eGFP, in which the cassette remains in the native TFIIIA context with eGFP fused to the C-terminal end (FIG. 3A). RT-PCR analysis of eGFP-P5SM$_{E/R}$ detected only the expected exon-skipped (SP-I) and exon-retained (SP-II) spliced products (FIG. 3B). The SP-I transcript was identical to the original eGFP coding sequence, except for the silent mutation, and its levels were increased ~1.5-fold by co-expression of *A. thaliana* L5 (AtL5), similar to previous observations for TFIIIA-eGFP (FIG. 3C) (23). The decrease in SP-II does not match the increase in SP-I, most likely because the abundance of the exon-retained spliced product is governed by NMD; this agrees with previous observations that the SP-II of TFIIIA is degraded (27).

Consistent with the RT-PCR analysis, increases in protein fluorescence with AtL5 induction were comparable between eGFP-P5SM$_{E/R}$ and TFIIIA-eGFP (FIG. 3D). The representative leaf scans for each construct (FIG. 3E) show similar AtL5 induction of eGFP fluorescence, as well as some background fluorescence induced by endogenous L5. These results support that the splicing cassette is fully functional within a foreign context—the eGFP coding sequence—with conservation of only the immediate bordering codons.

Figure 4:
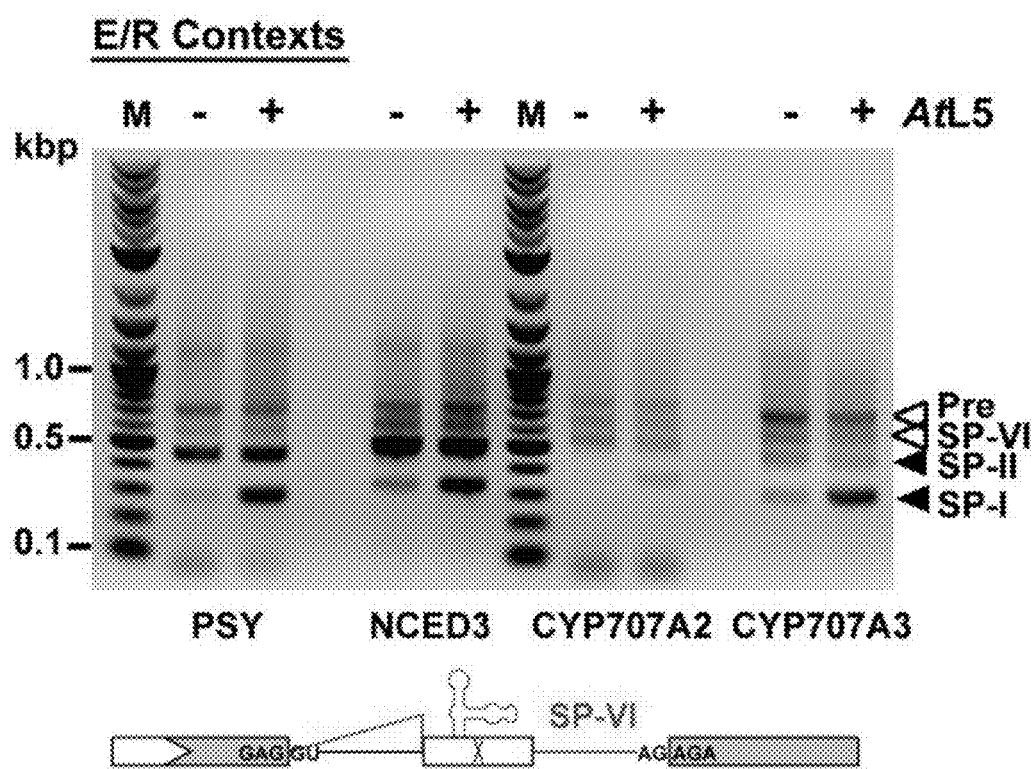
FIG. 4 shows that P5SME/R functions in additional *Arabidopsis* gene contexts. Spliced products detected by RT-PCR for phytoene synthase (PSY), 9-cis-epoxycarotenoid dioxygenase (NCED3), and abscissic acid 8′-hydroxylase (CYP707A2 and CYP707A3) harboring the P5SM cassette inserted within the E/R sequence context, upon induction with AtL5 (+) or LUC as a control (−). In addition to SP-I and SP-II, partially spliced (SP-VI) and unspliced pre-mRNA (Pre) were detected for these constructs. A schematic representation of SP-VI is shown.

We further inserted P5SM$_{E/R}$ into several *A. thaliana* protein-coding sequences, in place of E/R sequences naturally present within the first half of each ORF. In each of these constructs, splicing fidelity and regulation appear to be maintained, although some splicing intermediates were observed that correspond to unspliced and partially spliced pre-mRNA (FIG. 4). It is unclear whether these intermediates build up to detectable levels due to slower spliceosome processing or RNA degradation, but we later determined that they are not observed when the splicing cassette is inserted between other amino acid pairs within these coding sequences.

Determination of the Minimal Gene Context Requirements for the P5SM Splicing Cassette Expands its General Utility Expanding the repertoire of gene contexts beyond the wild-type E/R sequence would enable more facile design of splicing-regulated transgenes. Thus, to define the minimal context required for cassette function, we analyzed the effects of systematically mutating the bordering codons. Mutations upstream of the 5' splice site (ss) at positions −1 to −3 and downstream of the 3' splice site at positions +1 to +3 were performed on the TFIIIA-eGFP reporter (FIG. 5A). Since the amino acid changes are not in the eGFP sequence, the changes in fluorescence reflect the activity of the splicing cassette.

The effect of mutations to the bordering codons on splicing was analyzed by RT-PCR and the effect on gene expression was quantified by fluorescence leaf scanning (FIGS. 5B-5D, and FIG. 6). The results are consistent with the reported conservation pattern for nucleotides proximal to annotated 5' splice sites in *A. thaliana* (28), which we took to reflect the extent of influence on splice site strength. Position −3 had not been found to be highly conserved, and accordingly, the M1 and M2 constructs appear to retain full splicing activity. These mutants were characterized as splicing to SP-I and SP-II only, responding to AtL5 by an increase in SP-I, and exhibiting a similar fluorescence induction to WT. The U substitution at position −3 was not tested because it would generate a premature termination codon within the coding sequence.

Mutations at the more highly conserved positions −2 and −1 lead to partial or full loss of splicing fidelity and regulation. M3-M7 constructs harboring various mutations at position −2 were characterized as semi-functional. These mutants exhibit aberrant splicing but still some splicing to SP-I and SP-II, which leads to overall lower fluorescence induction relative to WT. Sequence analysis of the observed aberrant spliced products, SP-III and SP-IV, showed that they are generated by improper usage of an upstream 5' ss or intron retention, respectively (FIG. 5A). This is consistent with the idea that these mutations weaken recognition of the 5' ss. The M8 construct, which deliberately substitutes the least frequently observed nucleotides at positions −1 through −3, is fully non-functional. This mutant displays no induction of protein expression and only aberrant spliced products (SP-IV and SP-V), consistent with an impaired 5' ss.

Figure 5:
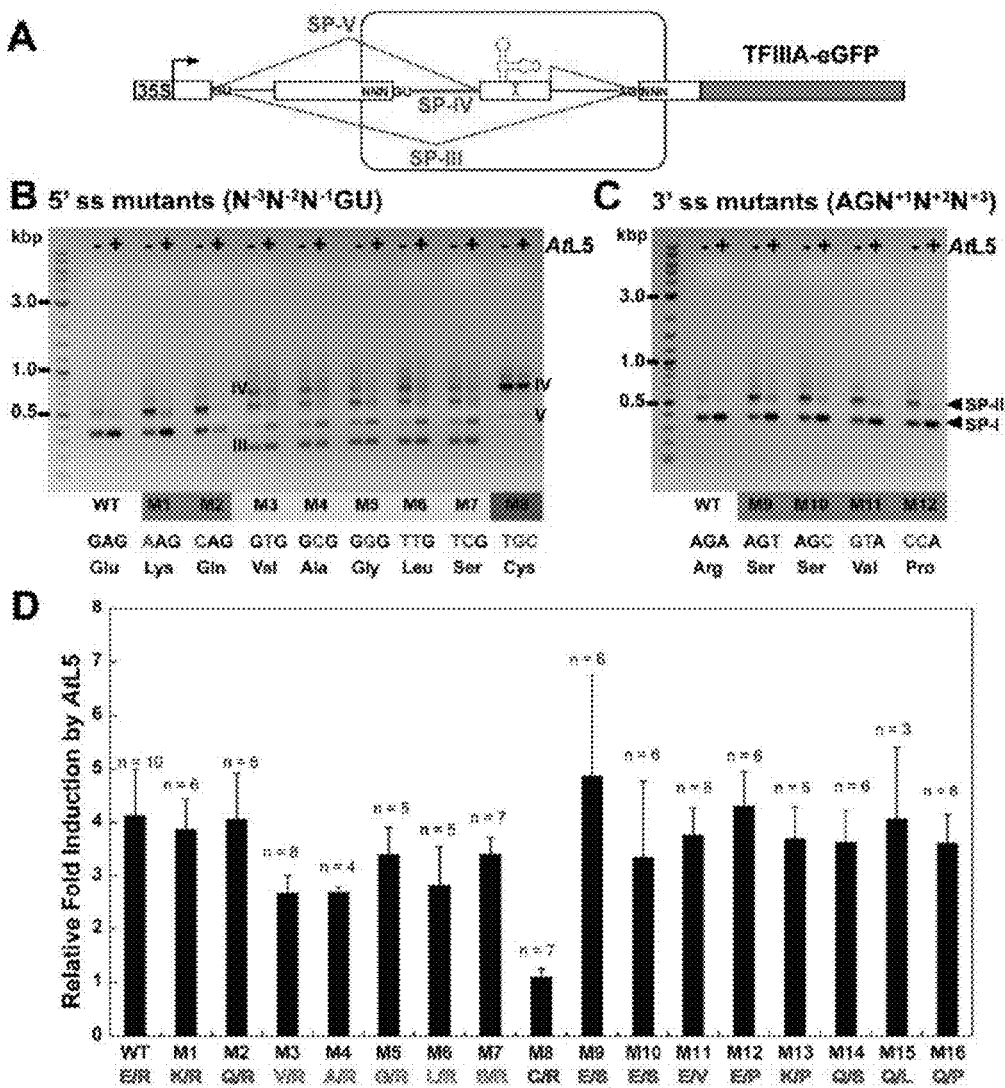
FIG. 5 shows that splicing activity of the cassette tolerates many, but not all, mutations to the bordering codons.
Figure 6:
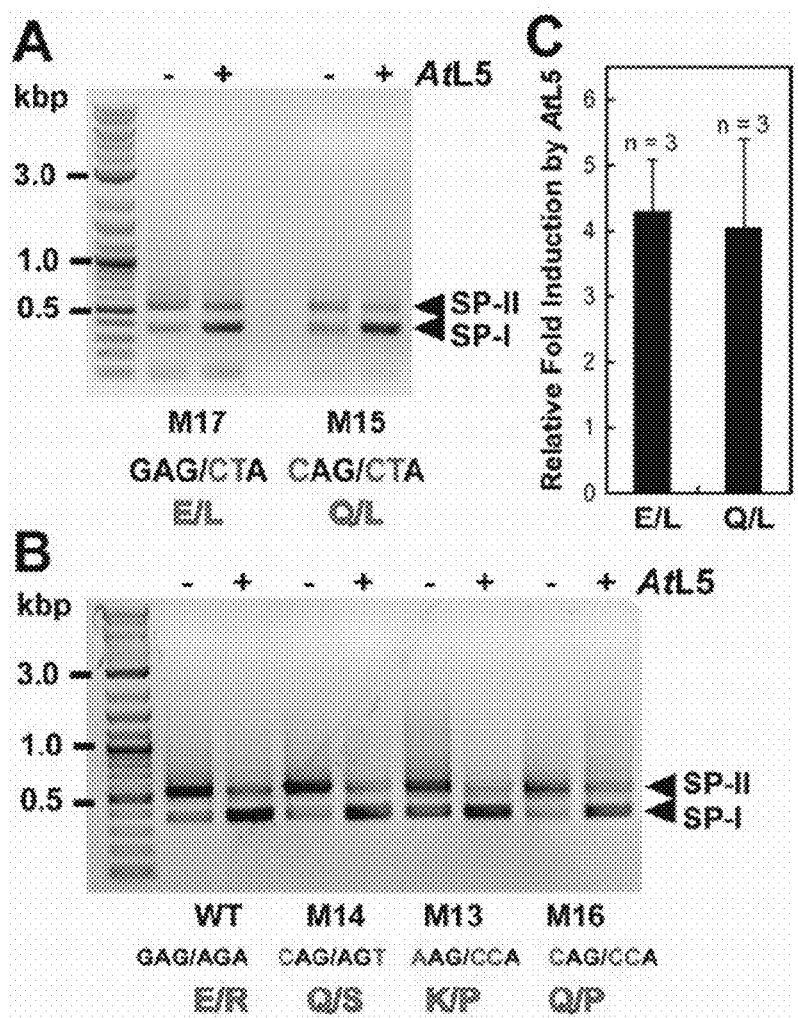
FIG. 6 shows that additional bordering codon mutations tested within TFIIIA-eGFP.

In contrast, alterations near the 3' ss do not appear to affect splicing activity, as evidenced by the M9-M12 constructs. Even the M12 construct, in which positions +1 and +2 are substituted with the least frequently observed nucleotides, maintains full splicing activity. We did not rigorously test mutations to position +3 because no nucleotide conservation was observed at this position (28). In addition, M13-M17 constructs confirm that double mutations to the bordering codons are tolerated as well as the corresponding single mutations (FIG. 5D and FIG. 6).

Figure 7:
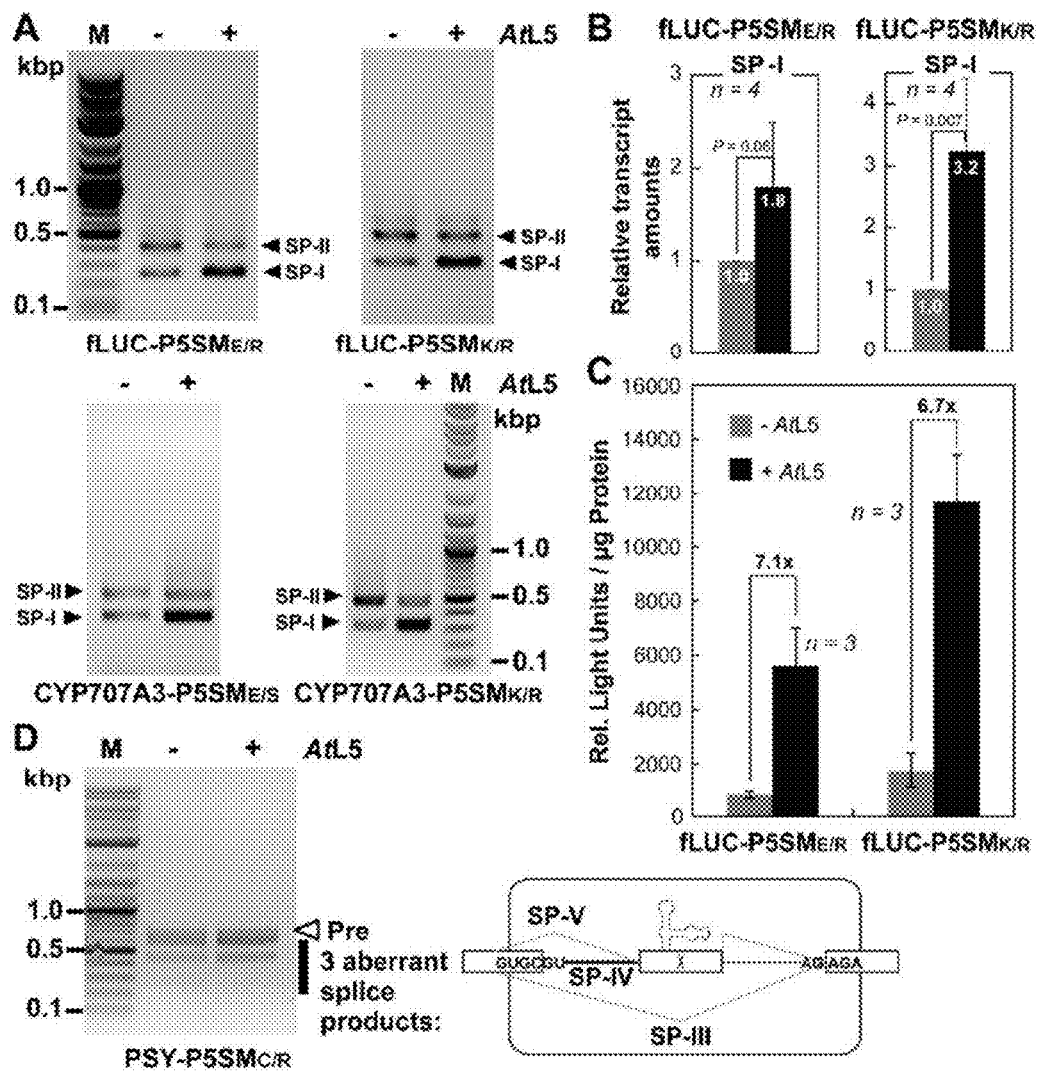
FIG. 7 shows that the cassette functions predictably in different gene contexts.

Taken together, these mutagenesis results suggest that full splicing activity for the splicing cassette requires a 5' context that extends to positions −1 and −2, but that there is no apparent requirement for the 3' context past the canonical 3' ss. In order to validate these surprisingly minimal exonic sequence requirements, we further analyzed the activity of the splicing cassette in ORF contexts corresponding to several of the tested mutations. The predicted functional contexts E/R, K/R, and E/S were tested in the ORFs for firefly luciferase (fLUC) or abscisic acid 8'-hydroxylase (CYP707A3) as a representative plant gene. In good agreement with the results for WT, M1, and M9 constructs, the splicing cassette in these ORFs displayed full splicing activity and (analyzed by enzyme activity for fLUC only) increased protein expression in response to AtL5 (FIGS. 3A-3C). The predicted non-functional context C/R was also tested in the ORF for phytoene synthase (PSY). Similar to the result for the M8 construct, the splicing cassette in this ORF is deregulated and gives related aberrant spliced products (FIG. 7D).

These data provide strong evidence that the mutagenesis results can reliably predict splicing activity for the P5SM cassette in other ORF contexts. If predicted functional contexts are limited to the 12 amino acid pairs that have been validated as giving full splicing activity (FIG. 5 and FIG. 6), bioinformatics analysis suggests that the splicing cassette can be inserted within the first half of 93% of annotated ORFs in the *A. thaliana* genome. However, our results also show that the 3' ss context appears not to influence cassette activity (FIG. 5). The minimal exonic context for full maintenance of splicing fidelity and regulation appears to be an AG immediately upstream of the 5' ss. An in-frame NAG codon would encode any of the amino acids Glu, Lys, or Gln. If we consider all ORFs that contain one of these three amino acids within the first half of their coding regions, the genome coverage estimate rises to 99.7%.

Rational Adaptation of a Species-Divergent P5SM Element Gives Robust, Orthogonal Gene Activation The natural P5SM cassette appears to maintain splicing fidelity and regulation within diverse coding sequences. However, one potential drawback is that basal activation from endogenous L5 contributes to background fluorescence and leads to relatively modest (~4-7 fold) levels of gene induction by AtL5 (FIGS. 3D and 6C). To eliminate basal activation, one might consider knocking out the endogenous protein, but since L5 is a component of the ribosomal machinery, this is expected to be highly detrimental. Also, it is preferable to avoid requiring a specific genotype for use of the splicing cassette.

Figure 8:
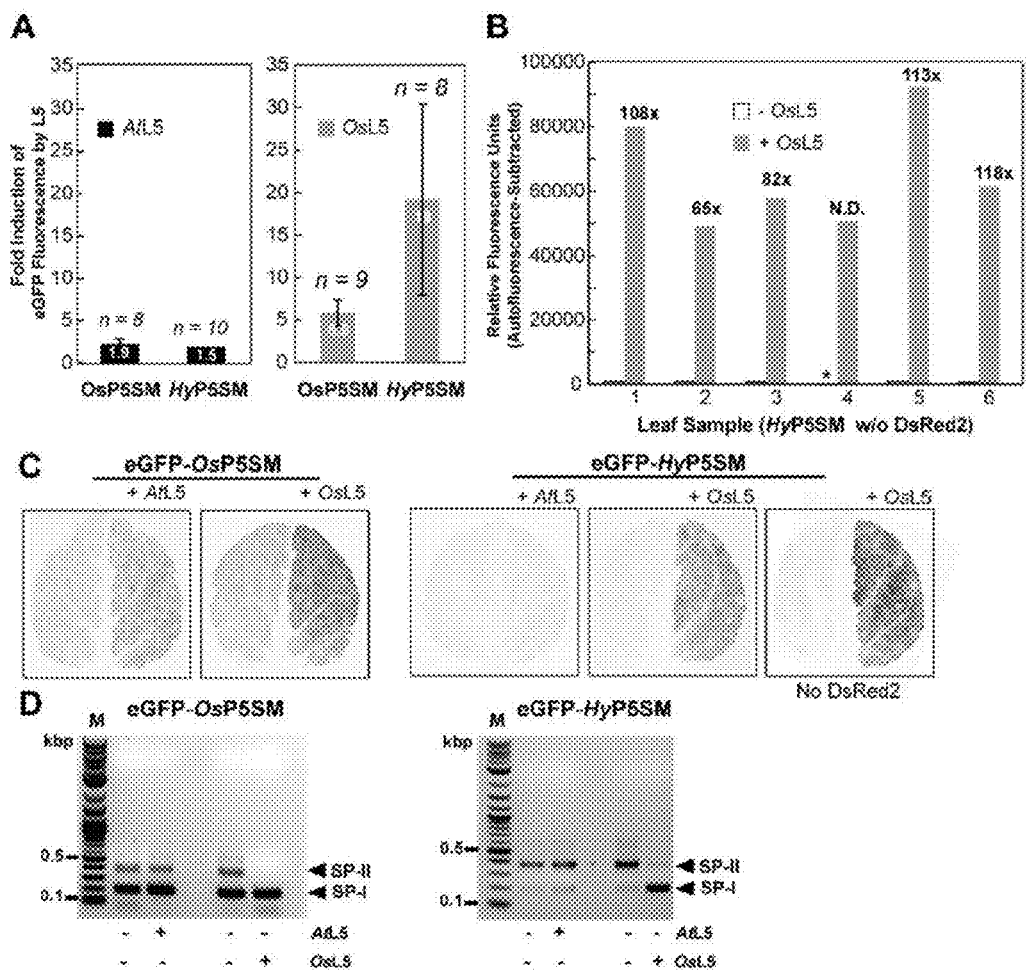
FIG. 8 shows that rational design of the P5SM RNA element leads to generation of an orthogonal splicing cassette.

Alternatively, we reasoned that the P5SM RNA element from a more divergent plant species might be less responsive to the endogenous L5 as compared to the *A. thaliana* P5SM RNA element. Both *A. thaliana* and *Nicotiana benthamiana*, the model species in which the transient expression assays have been performed, are dicots. Thus, we replaced the P5SM RNA element in the reporter construct eGFP-P5SM$_{E/R}$ with the one derived from the monocot *O. sativa*, which was termed OsP5SM. We found that splicing activity is maintained for the new construct eGFP-OsP5SM$_{E/R}$, which also exhibits a higher level of induction by OsL5 than AtL5 (FIG. 8A). This construct was expected to give lower background fluorescence due to reduced activation by the endogenous L5. Instead, higher background fluorescence was observed (FIG. 8C, left side of leaves), corresponding to an increased ratio of SP-I to SP-II in the uninduced sample (FIG. 8D).

Figure 9:
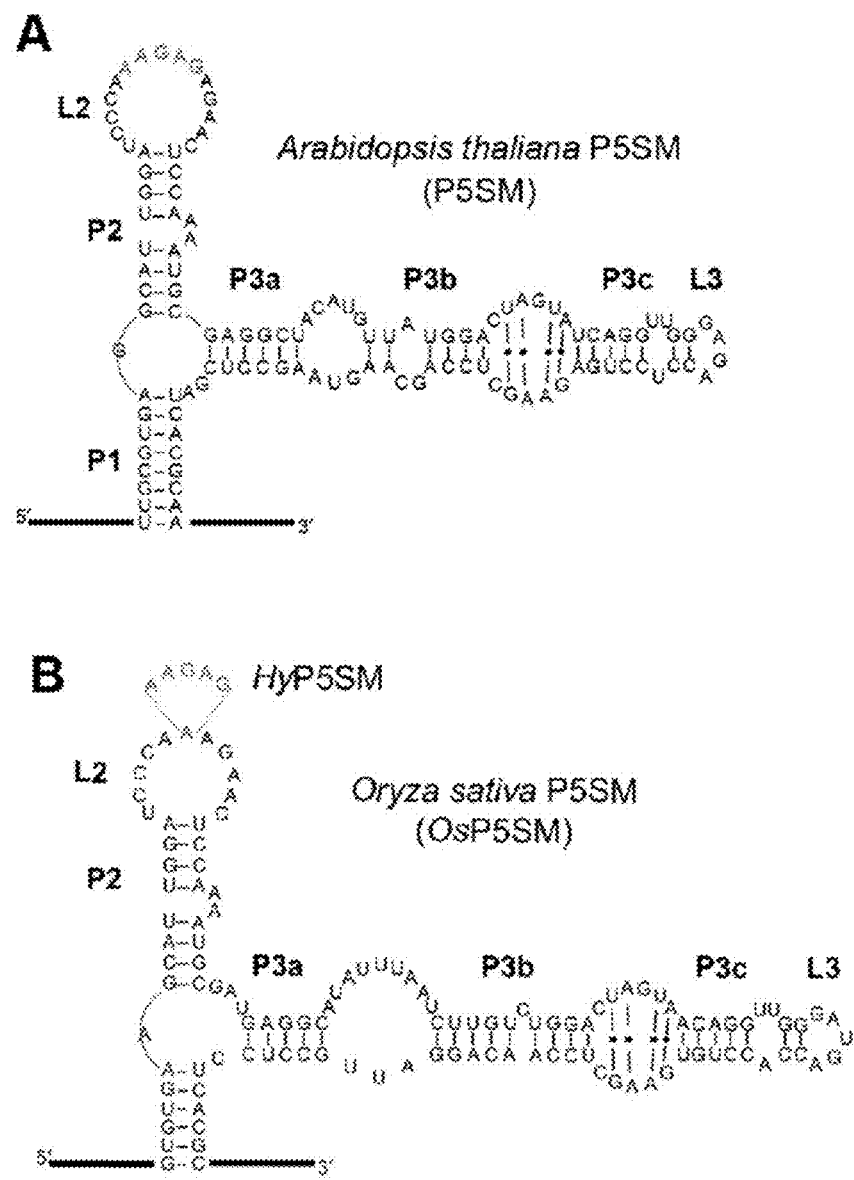
FIG. 9 shows the secondary structures and sequences of AtP5SM, OsP5SM, and HyP5SM.

This unexpected result can be rationalized in light of the proposed regulatory mechanism for how the P5SM-L5 interaction influences alternative splicing (23). Previous data have suggested that L5 protein binding to the P5SM RNA element acts to displace an exon-defining splice factor from the L2 loop, which results in exon skipping. The L2 loop of the *A. thaliana* P5SM RNA element has an extended purine-rich sequence that is shortened in the rice element (FIG. 9). It had been shown that substitution of this purine-rich sequence with the sequence UC leads to constitutive exon skipping (23). Thus, we hypothesized that swapping in the OsP5SM RNA element not only disrupted binding to endogenous L5 but also to the putative splice factor.

Loss of exon definition due to a reduction in splice factor binding or another mechanism involving the L2 loop could explain the increase in SP-I and high background fluorescence. To address this possibility, we converted the sequence of the OsP5SM L2 loop to match the purine-rich *A. thaliana* sequence and tested a construct containing the hybrid P5SM (HyP5SM) sequence, eGFP-HyP5SM (FIG. 9). This construct exhibits strong induction (~19-fold) by OsL5, almost no induction (~1.5-fold) by AtL5, and very low background fluorescence (FIGS. 8A and 8C). With such low background fluorescence, slight variations in this value resulted in a large standard deviation for fold induction between individual leaf samples.

Figure 10:
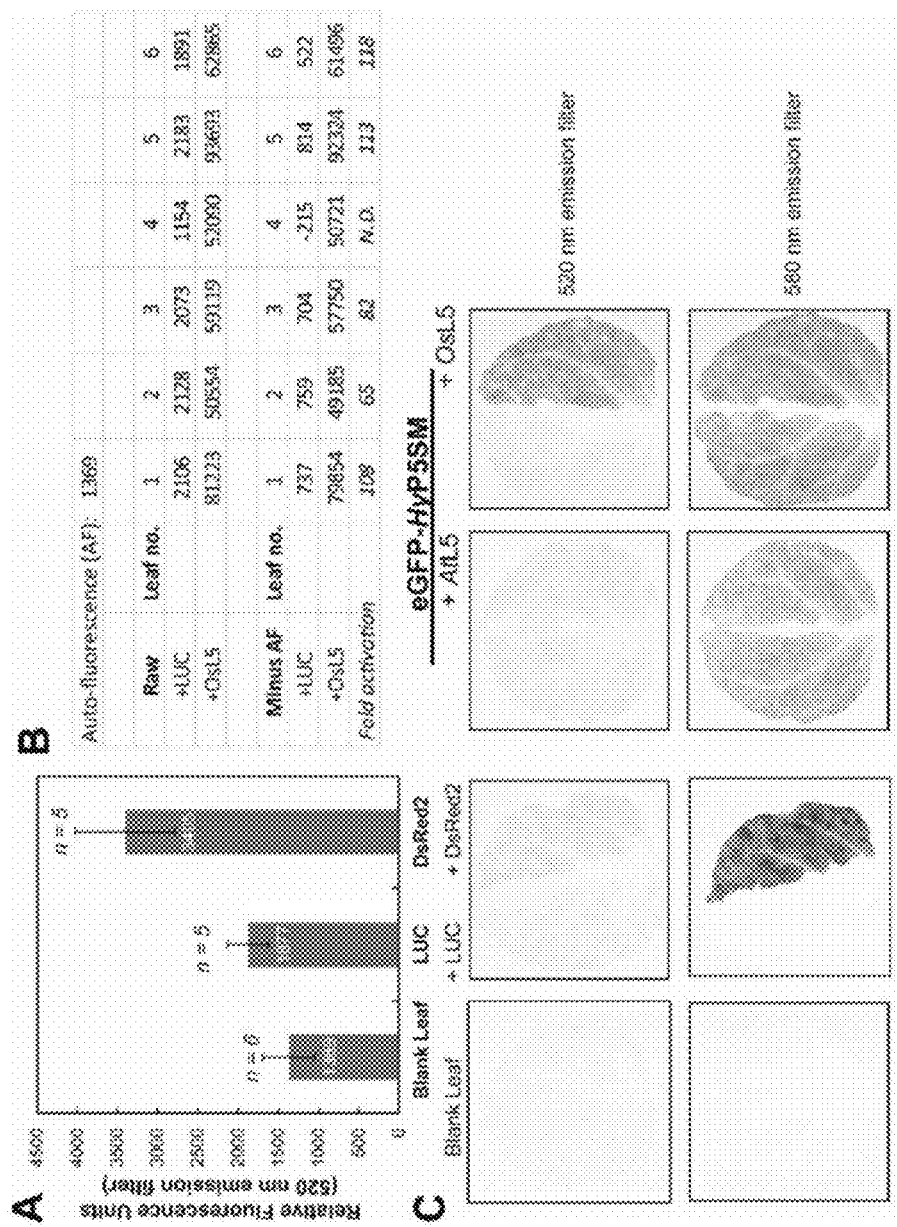
FIG. 10 shows that leaf autofluorescence and DsRed2 expression contributes to background fluorescence.
Figure 11:
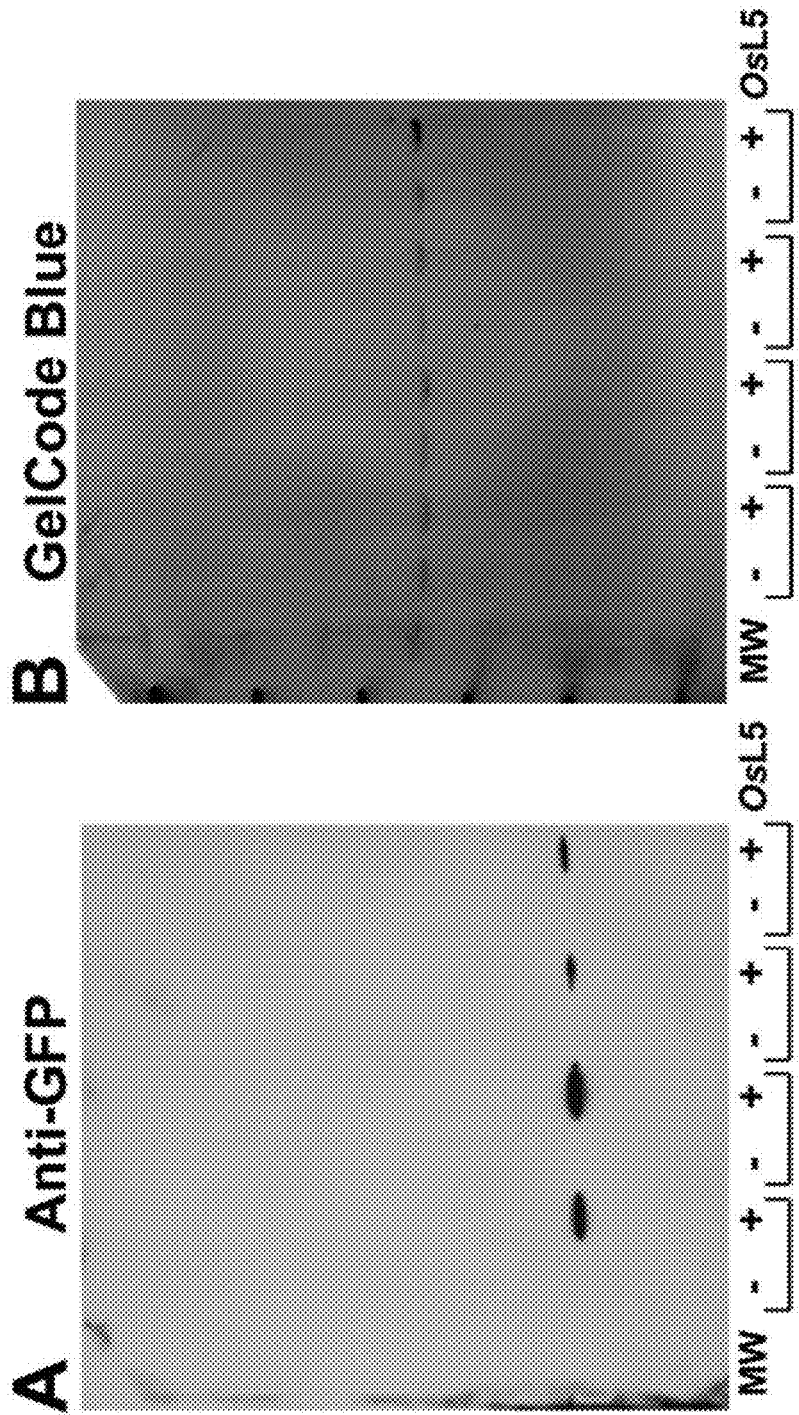
FIG. 11 shows western blot analysis of eGFP-HyP5SM expression.

Furthermore, it was determined that DsRed2, the fluorescent protein used as a normalization standard in all of the experiments, contributed to the residual background fluorescence. In the absence of DsRed2, little to no background above autofluorescence was observed for eGFP-HyP5SM in the absence of OsL5 induction (FIG. 10). With the exclusion of DsRed2 and with subtraction of autofluorescence, both of which had not been done in previous experiments, it was revealed that the activation of gene expression is very strong (~97-fold on average) (FIG. 8B). Correspondingly, western blot analysis with a GFP-specific antibody to measure protein levels detected the expressed protein only in OsL5 induced samples (FIG. 11). Consistent with the protein fluorescence and immunoblot data, RT-PCR analysis revealed an almost complete switch in splicing upon induction by OsL5 but not AtL5 (FIG. 8D).

Discussion

Our construct designs and the associated bioinformatics estimates for genome coverage include two simplifying assumptions which impose conservative restrictions on gene context. First, we artificially limit the site of cassette insertion to within the first half of ORFs, so that even in the absence of NMD mechanisms, the exon-retained spliced product would not generate functional protein. However, premature termination codons have been shown to activate NMD as long as they are upstream of an exon junction by some distance. In *N. benthamiana*, introduction of the well-characterized Ls intron within the 3' UTR of an otherwise stable mRNA triggers NMD when the stop codon is 99 nt but not 28 nt upstream of the location of intron placement (12). This observation is consistent with the general rule established in mammals, which is that NMD is usually triggered if a stop codon is ~50-55 nt upstream of an exon junction (29). The premature termination codon in the P5SM suicide exon is 121 nt upstream of the exon junction, and the exon-retained spliced product of *A. thaliana* TFIIIA is subject to NMD (27). Regardless of gene context, the splicing cassette maintains the suicide exon at the same distance upstream of the exon junction, so its location does not necessarily need to be within the first half of the ORF to trigger NMD. However, cassette insertion at a roughly central location may help ensure that each ORF section is of sufficient length to be recognized as an exon.

Second, we only consider in-frame cassette insertion sites which allow us to generate proper splice site contexts via synonymous codon substitutions. It is very likely that the conserved AG sequence upstream of the 5' ss does not have to be in-frame with the ORF, although this remains to be tested. Our observation that mutations in the extended 3' ss context have no effect is consistent with the spliceosome cycle as elucidated in mammalian systems, in which the 5' ss and branchpoint are first recognized (30). The branchpoint region of the 3' intron can be readily identified, as it is 27 nt upstream of the 3' ss and conforms to the plant consensus, CURAY (31). Thus, it appears that maintenance of the distance between the 3' ss and the strong branchpoint signal is sufficient for proper splice site recognition. Taken together, it is believed that the P5SM splicing cassette will regulate the expression of any gene with the dinucleotide AG in its coding sequence, which effectively would mean that any gene can be regulated in a traceless fashion.

The splicing cassette was reliably engineered into three different ORFs, eGFP, fLUC, and CYP707A3. The targeted ORFs did not originally possess introns at the site of cassette insertion, but in each case the suicide exon was spliced with no observable loss of fidelity. All of the predicted functional contexts we have tested maintain activation of alternative splicing by L5, demonstrating that the splicing cassette retains the necessary cis regulatory elements. A ~2-fold difference in expression level was observed between the E/R and K/R contexts in the fLUC gene, regardless of the presence or absence of AtL5 (FIG. 7C). Thus, there can be a slight sequence context effect that is independent of alternative splicing regulation. Accordingly, two or three different contexts in the same ORF should be tested for optimal function. This strategy is practical because most coding sequences contain multiple candidate sites for cassette insertion, and overlap extension PCR employing different primers can be used to generate all of the desired constructs at the same time.

Essentially no fluorescence was measured for the eGFP-HyP5SM reporter in the absence of OsL5 induction (FIG. 8B), even though the strong, constitutive CaMV 35S promoter was used to drive transcription and the experiment was performed in wild-type plants. This result shows that conditional splicing does not require the use of weak promoters or specialized genotypes. Furthermore, this result demonstrates that a plant-derived regulatory element could be employed in plants with almost no leaky expression. Basal activation by endogenous L5 was eliminated through rational improvements to the P5SM RNA element that were devised from our understanding of its role in alternative splicing. The splicing cassette harboring the HyP5SM RNA element was selectively activated by OsL5 over AtL5 (FIG. 8A). Restoration of the purine-rich L2 loop was required to promote default exon retention, which is consistent with the observation that purine-rich motifs act as exonic splicing enhancers in *A. thaliana* (32). The ribosomal protein L5 for *N. benthamiana* has not been fully sequenced, so a direct assay has not been performed, but the little to no background induction observed in wild-type *N. benthamiana* supports that NbL5 also does not recognize the HyP5SM RNA element.

It is not immediately obvious which nucleotide changes to the RNA element are responsible for the discrimination in binding of OsL5 versus AtL5. There are very few differences in sequence between the original and hybrid P5SM in the regions that are homologous to 5S rRNA (the L2/P2 and P3c/L3 regions, FIG. 9). More differences are observed in the P3a/b stem, which in general exhibits higher sequence variability between representatives (23).

Because L5 is not a general splice factor and instead interacts specifically with the P5SM element, the activation of transgene expression by alternative splicing is highly robust and selective. Co-expression of OsL5 increases the levels of the reporter protein ~97-fold (FIG. 8B) but has no effect on the levels of another fluorescent protein, DsRed2, used as a normalization standard in all other experiments (FIG. 10). This result is particularly impressive given that only a single copy of the P5SM RNA element is present in the splicing cassette. The induction of protein expression is comparable to that obtained using a conditional promoter harboring six copies of the GAL4 upstream activating sequence upon dexamethasone treatment (33).

Figure 12:
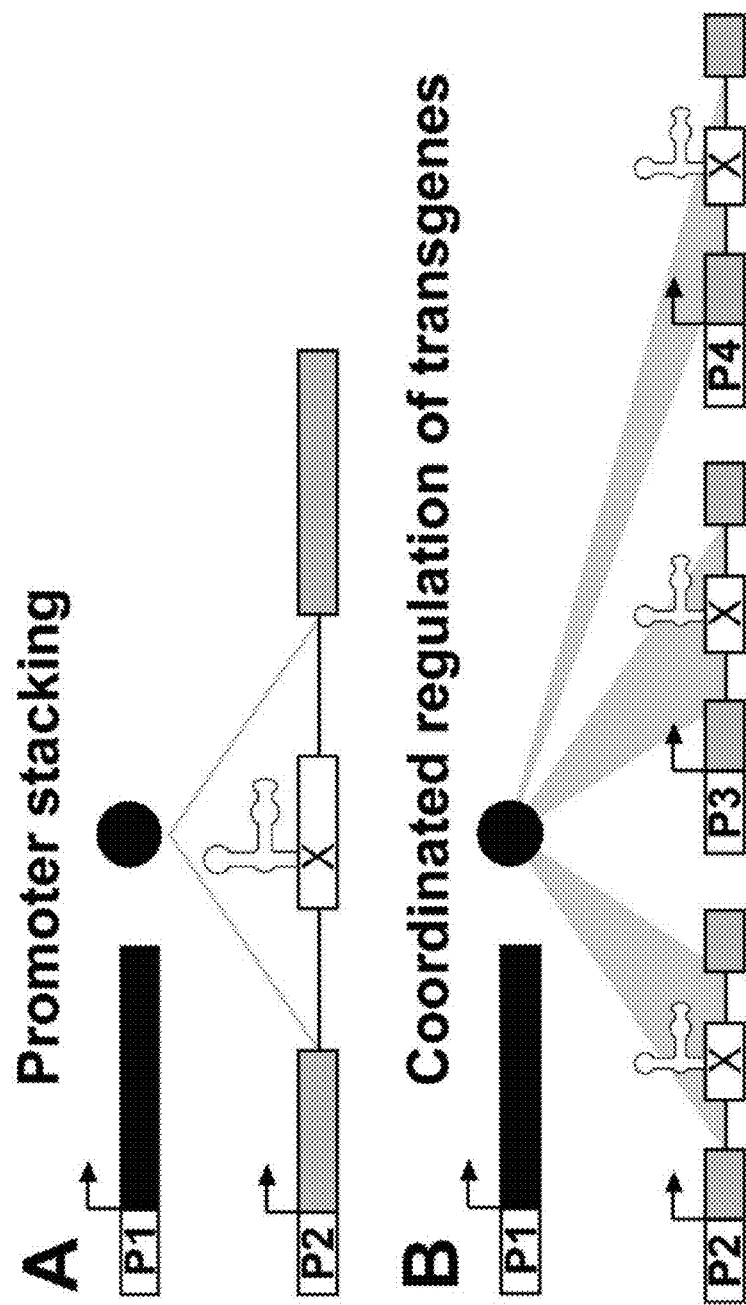
FIG. 12 shows strategies for transgene regulation that combine conditional promoters and splicing cassettes.

In conclusion, we have adapted a natural splicing cassette to serve as a portable regulatory element that robustly controls gene expression via alternative splicing. Gene regulation by the suicide exon is effectively traceless, as induced exon skipping affords the original ORF with at most one or two synonymous codon substitutions. This, along with the minimal requirements for sequence context, makes the regulation of any gene of interest quite facile using the P5SM splicing cassette. Thus, we have shown that conditional splicing can be a general and effective mechanism for transgene regulation. It is envisioned that the ability to combine DNA- and RNA-level regulation will enable novel strategies for controlling the expression of single genes with multiple promoters and for coordinating the expression of genes without the use of homologous promoters (FIG. 12).

Example 2

The following Example relates to the generation and characterization of a chemical-inducible P5SM suicide exon cassette that can activate or inhibit expression of a transgene.

Chemically Activatable Splicing Cassette

Figure 13:
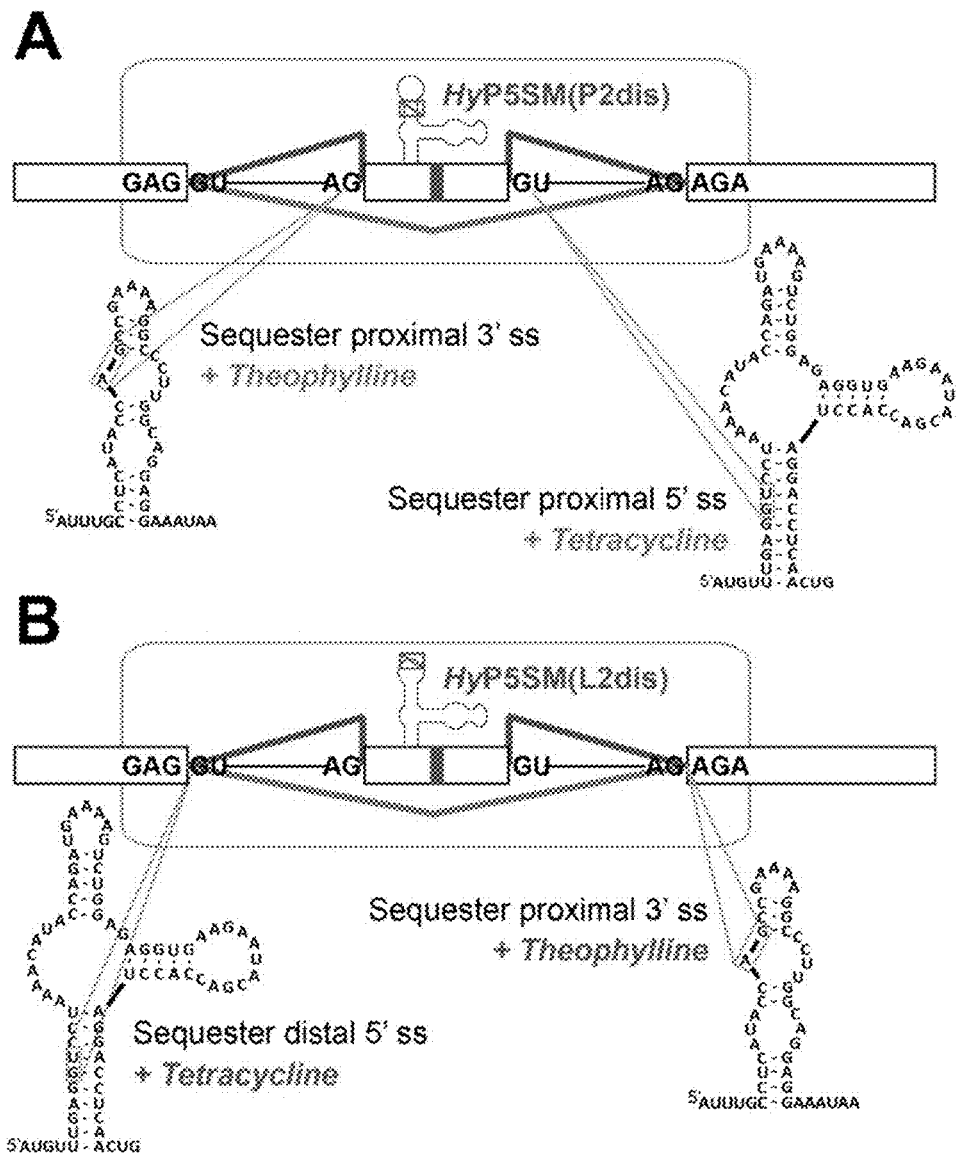
FIG. 13 shows designs of chemical-inducible HyP5SM splicing cassettes (SEQ ID NO: 159 and 160)
Figure 14:
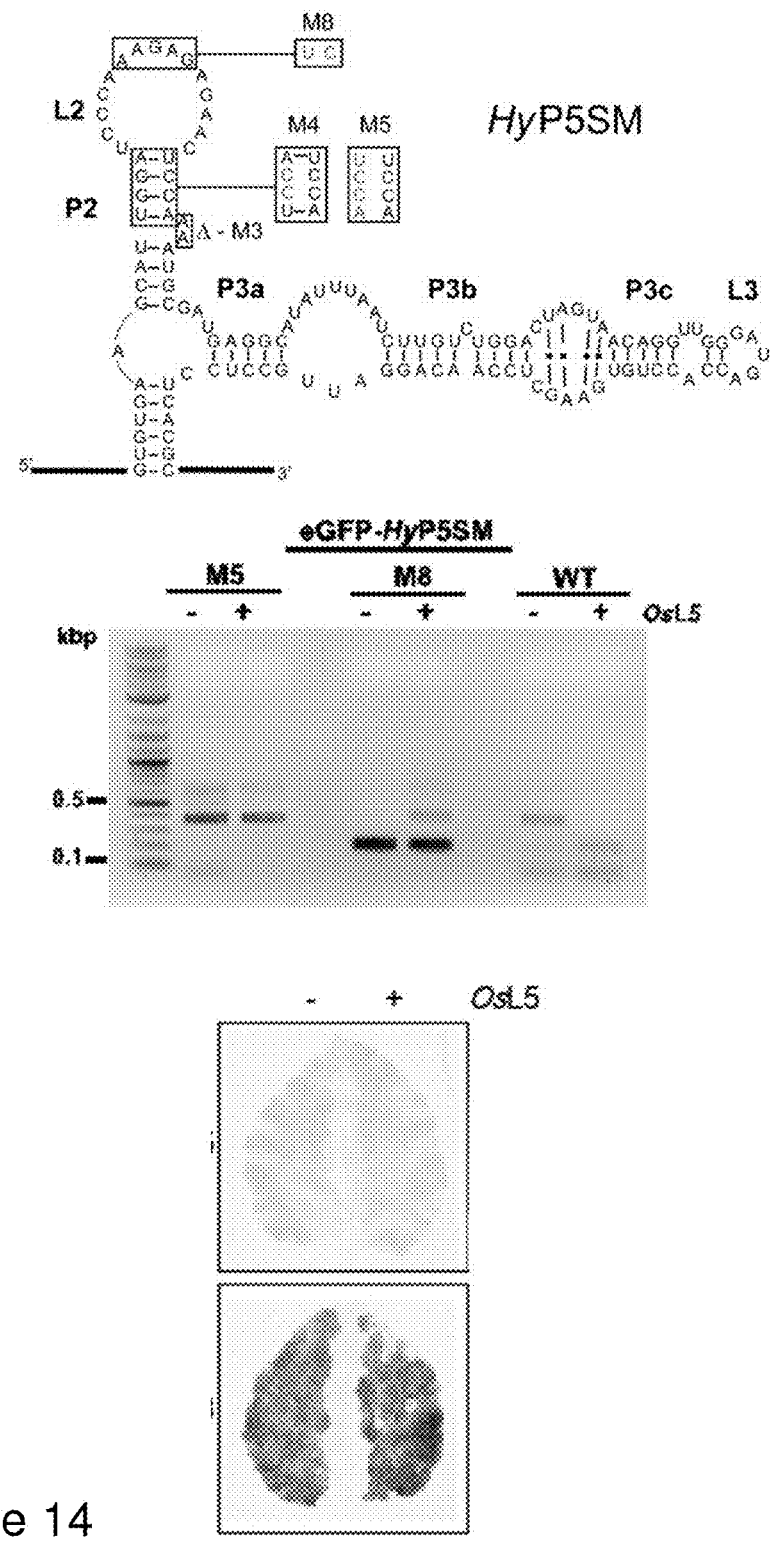
Figure 15:
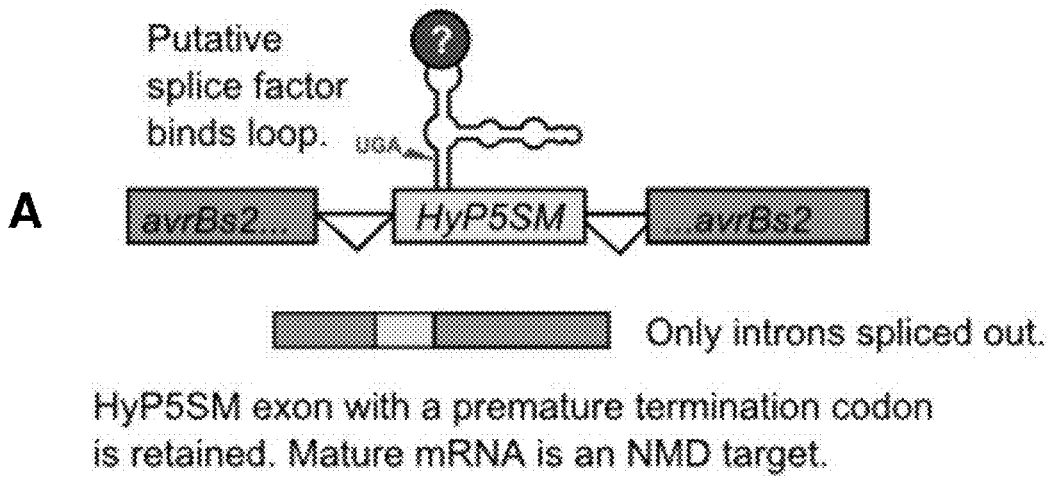
Figure 15:
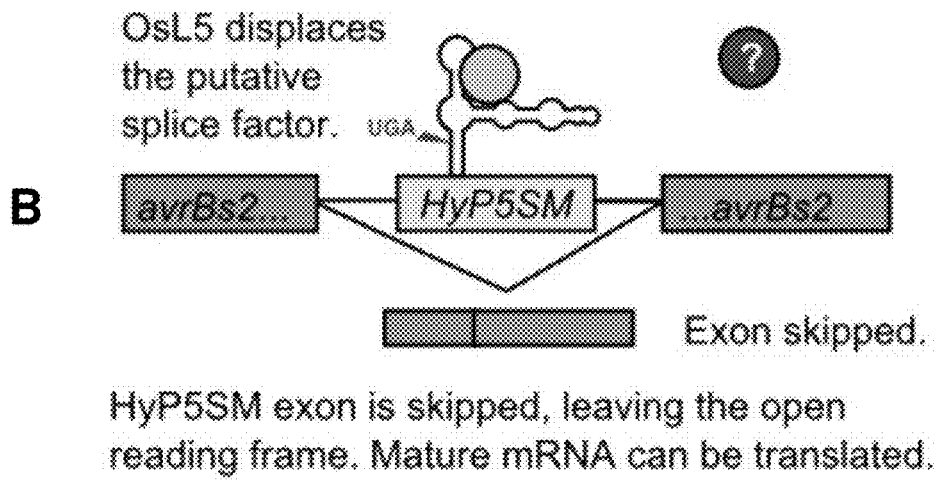
Figure 16:
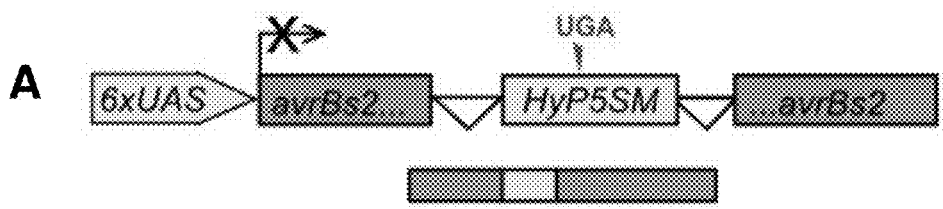
Figure 16:
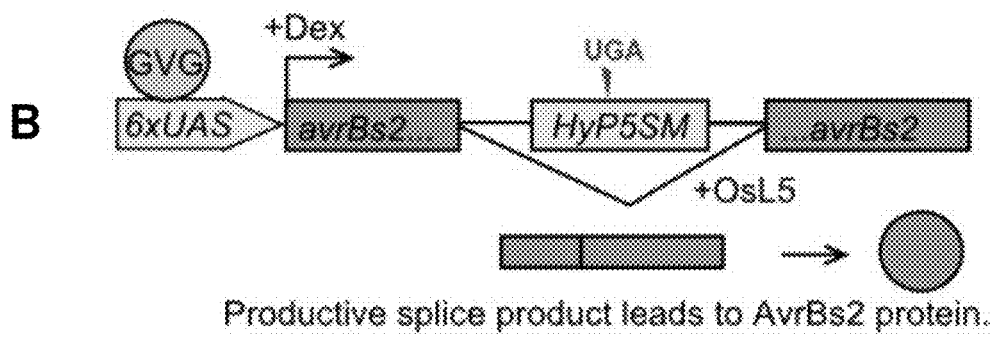

We have shown that mutations to the P2 stem (M4/M5) of HyP5SM eliminate binding to the L5 ribosomal protein and lead to constitutive exon retention within a transgene, i.e., default gene expression is off (FIG. 14). In these mutations by default, the proximal splice sites are used, thus the P5SM element is retained. We will introduce a nucleotide aptamer sequence to overlap the proximal 5' splice site or the proximal 3' splice site (FIG. 13A), so that the addition of a chemical inducer, such as theophylline or tetracycline, will sequester the proximal slice sites. Sequestration of the proximal splice sites will lead to P5SM exon skipping and consequently activate transgene expression, as binding of the chemical inducer to the aptamer forces splicing at the distal splice sites, which leads to excision of the P5SM element from the transgene via exon skipping (FIG. 13A).

Chemically Repressible Splicing Cassette

Figure 18:
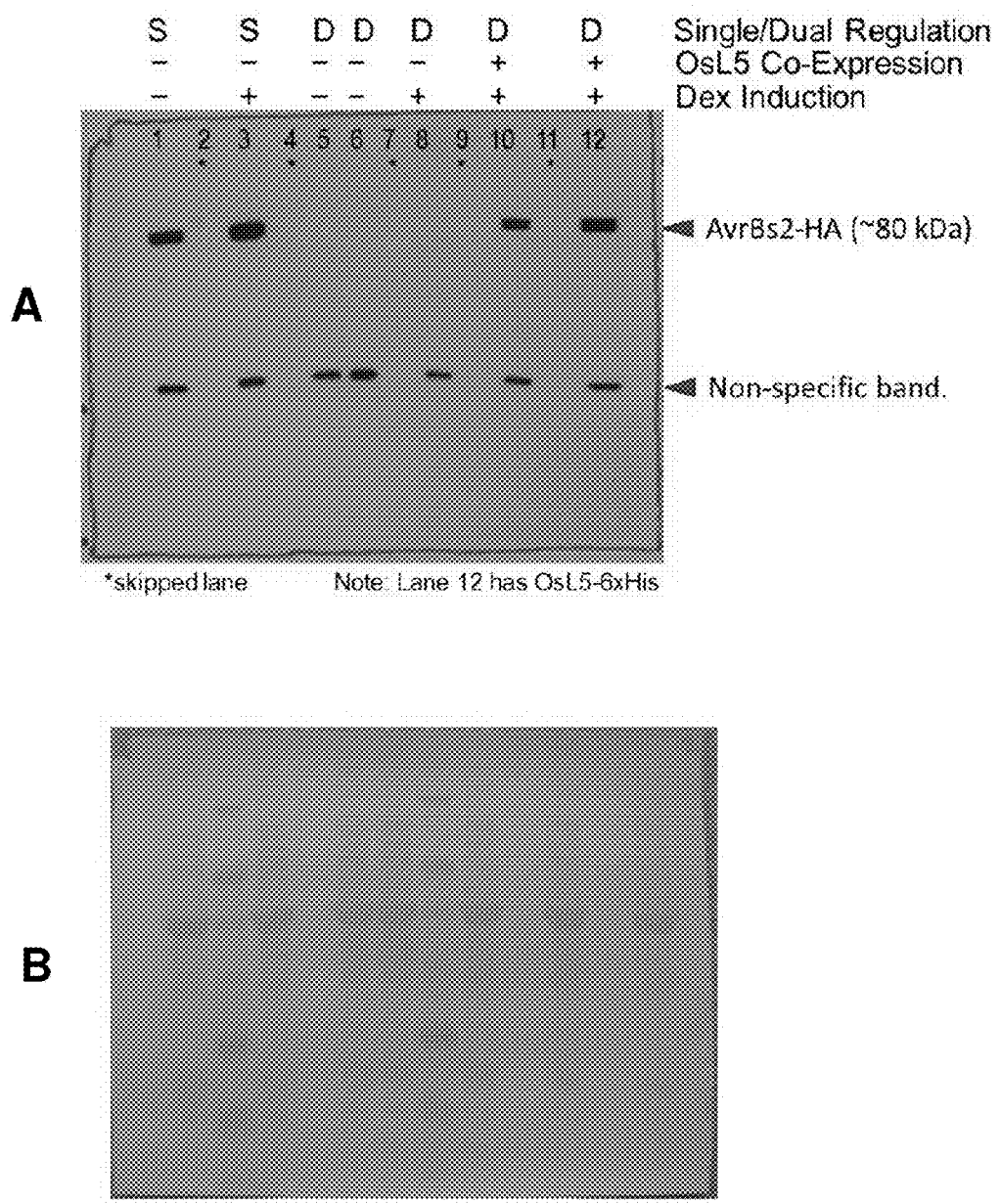

We have shown that mutations to the L2 stem (M8) or the dinucleotide bulge of the P2 stem (M3) of HyP5SM eliminate responsiveness to the L5 ribosomal protein and lead to constitutive excision of the exon from a transgene via exon skipping, i.e., default gene expression is on (FIG. 14). We will introduce a nucleotide aptamer sequence to overlap the distal 5' splice site or the distal 3' splice site (FIG. 13B), so that addition of a chemical inducer, such as theophylline or tetracycline, will sequester the distal splice sites. Sequestration of the distal splice sites will lead to P5SM exon retention within the transgene and consequently inhibit transgene expression, as binding of the chemical inducer to the aptamer forces splicing at the proximal splice sites which leads to retention of the P5SM element (FIG. 13B).

FIG. 13 shows sequences for the theophylline- and tetracycline-specific nucleotide aptamers, which have been previously described (34,35). We will alter these sequences to eliminate any cryptic 5' or 3' splice site sequences that would interfere with the desired function of the splicing cassette. We will also test other arrangements of the sequestered 5' or 3' splice sites within the nucleotide aptamer in order to optimize for chemical inducibility.

Example 3

The following Example relates to the use of the engineered HyP5SM suicide exon cassette to regulate expression of the pathogen effector protein AvrBs2.

Introduction

Effector-triggered immunity (ETI) is a plant innate immune pathway that is activated when plants that possess disease resistance (R) genes recognize specific pathogen effector proteins. The ETI response includes a defensive “hypersensitive response” (HR) that involves localized cell death at the site of pathogen recognition, thereby quarantining the pathogen. Although many R protein and effector protein pairs are known to trigger HR when co-expressed, the immediate and far downstream signaling events remain unclear. Generating transgenic plants that inducibly express effector proteins is problematic due to the very sensitive HR phenotype triggered by low levels of the effector protein.

AvrBs2 is a conserved bacterial effector protein from *Xanthomonas euvesicatoria*, the agent responsible for black spot disease in tomatoes and pepper plants. Mutations of the avrBs2 gene reduce virulence, and supplementation with a plasmid carrying wild-type avrBs2 restores full virulence (36).

Bs2 is a disease resistance protein that recognizes AvrBs2 and initiates the hypersensitive response. Bs2 was found in pepper plants immune to black spot disease and has been shown to function in tomatoes and *Nicotiana benthamiana* (38). Bs2, like almost all discovered disease resistance proteins in plants, has a nucleotide binding (NB) and leucine rich repeat (LRR) domains. Similar domains are also found in the NOD-like receptors of animal innate immune systems.

In the following Example, a dual regulation strategy was used to tightly regulate the bacterial effector protein AvrBs2 by utilizing a chemically-inducible promoter and the alternatively spliced cassette exon called HyP5SM. We engineered the HyP5SM to highly favor a non-productive splice product by default, thus reducing background protein levels. We also engineered the HyP5SM to switch to a productive splice product upon co-expression of the rice L5 protein (OsL5), thus recovering protein expression. The following results demonstrate that, in transiently transformed *Nicotiana benthamiana*, the dual regulation strategy reduces or eliminates detectable background HR. This result is mediated by the splicing of HyP5SM, and by the reduction in AvrBs2 protein levels. Furthermore, plants recovered the HR phenotype when the promoter and HyP5SM exon skipping were induced.

Alternatively Spliced HyP5SM Exon

The HyP5SMexon was generated as described in Example 1. As shown in FIG. 15A, inserting the HyP5SM exon into the avrBs2 gene reduces background protein expression in the absence of the OsL5 protein. However, co-expressing with OsL5 results in a shift to the protein-producing splice product and a recovery of sufficient AvrBs2 protein to induce the hypersensitive response (FIG. 15B). As described in Example 1, HyP5SM is an engineered hybrid of the rice P5SM (OsP5SM) structure with the putative splice factor binding loop of *Arabidopsis thaliana* P5SM (AtP5SM). HyP5SM has low background protein expression in *Nicotiana benthamiana*, and expression is inducible ~97-fold with OsL5 (37).

Dual Regulation Strategy

In order to achieve tight gene regulation, the dexamethasone-inducible promoter system from Aoyama and Chua (23) was used in combination with the HyP5SM exon (FIG. 16).

As shown in FIG. 16B, upon addition of dexamethasone the chimeric transcription factor GVG is localized to the nucleus and binds the 6xUASGAL4 promoter controlling the avrBs2-HyP5SM-HA gene.

Results

As shown in FIGS. 17 and 18, dual regulation eliminated detectable background expression.

RT-PCR for avrBs2-HyP5SM-HA Demonstrates Clear Splice Factor Ratio Shift

Using *Agrobacterium*-mediated transient transformations of *Nicotiana benthamiana* leaves, the avrBs2-HyP5SM-HA gene was co-transformed with the constitutive Luciferase (control) or constitutive OsL5 (to induce HyP5SM skipping) promoters, or the dexamethasone-inducible promoter. The experiment was performed with six leaf halves, three without OsL5 and three with OsL5. As shown in FIG. 17, without OsL5 the HyP5SM exon retaining splice product of the avrBs2-HyP5SM-HA pre-mRNA was highly favored. However, with OsL5 the protein-producing splice product was favored instead (FIG. 17).

The radical shift in splice factor ratios was evident even when avrBs2-HyP5SM-HA was constitutively expressed (FIG. 17). This result suggests that the clean shift in the major splice product for the dexamethasone-inducible avrBs2-HyP5SM-HA samples (lanes 9 & 10) was not simply due to low amounts of template (FIG. 17, lanes 9 and 10).

RT-PCR Also Demonstrates Leaky Transcription

In the leaf samples tested, the dexamethasone-inducible promoters should be “off”, since the leaf was not exposed to the inducer. However, as seen in lanes 9 and 10 of FIG. 17, transcription still occurred. Lane 2 was a positive control that included the inducible avrBs2-HA with dexamethasone.

Leaky Protein Expression is Undetectable As shown in FIG. 18A, protein from dexamethasone-inducible avrBs2-HA lacking HyP5SM (only single regulation) was detectable both with and without dexamethasone (lanes 1 and 3).

Figure 17:
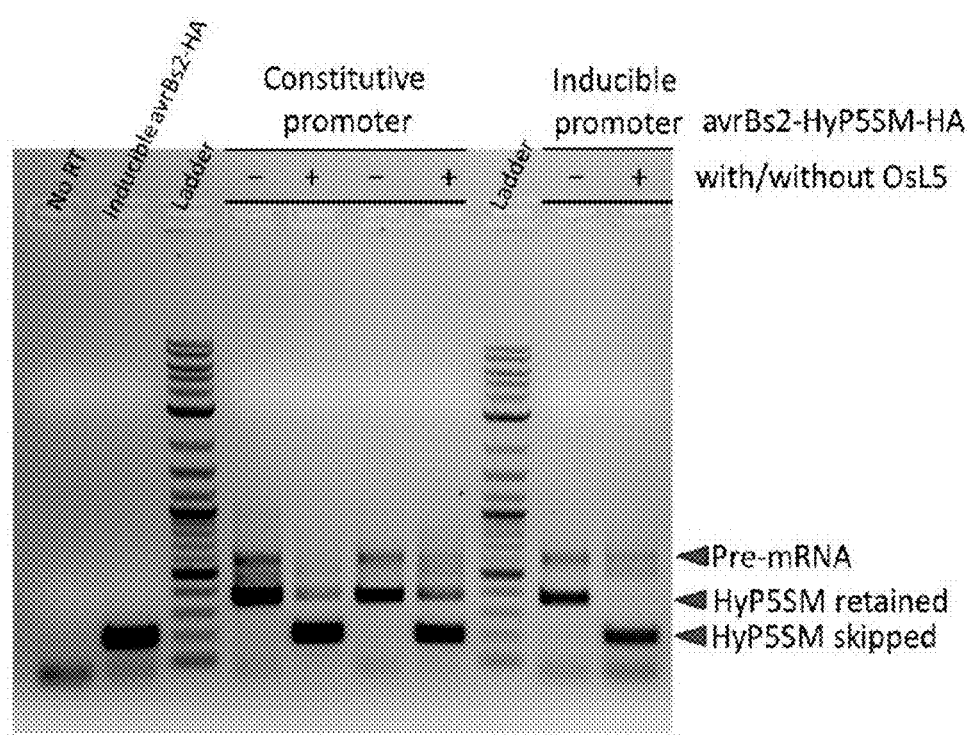

While leaky transcription from the inducible promoter was not eliminated (FIG. 17), the HyP5SM exon of splicing signals and their corresponding splicing factors in eukaryotes. *Genome Res,* 18, 88-103.
29. Maquat, L. E., Tarn, W. Y., and Isken, O. (2010) The pioneer round of translation: features and functions. *Cell* 142, 368-374.
30. Burge, C. B., Tuschl, T., Sharp, P. A. (1999) Splicing of precursors to mRNAs by the spliceosomes. *The RNA World,* ed Gesteland, R. F., Cech, T. R., Atkins, J. F. (Cold Spring Harbor Laboratory Press, Cold Spring Harbor), 2nd Ed, pp 525-560.
31. Schuler, M. A. (2008) Splice site requirements and switches in plants. *Curr Top Microbiol,* 326, 39-59.
32. Egoavil, C., Marton, H. A., Baynton, C. E., McCullough, A. J., and Schuler, M. A. (1997) Structural analysis of elements contributing to 5' splice site selection in plant pre-mRNA transcripts. *Plant J,* 12, 971-980.
33. Aoyama, T. and Chua, N. H. (1997) A glucocorticoid-mediated transcriptional induction system in transgenic plants. *Plant J,* 11, 605-612.
34. Weigand, J. E. and Suess, B. (2007) Tetracycline aptamer-controlled regulation of pre-mRNA splicing in yeast. *Nucleic acids research,* 35, 4179-4185.
35. Gusti, V., Kim, D. S, and Gaur, R. K. (2008) Sequestering of the 3' splice site in a theophylline-responsive riboswitch allows ligand-dependent control of alternative splicing. *Oligonucleotides,* 18, 93-99.
36. Kearney, B. and Staskawicz, B. J. Widespread distribution and fitness contribution of *Xanthomonas campestris* avirulence gene avrBs2. *Nature.* 1990, 346(6282), 385-6.
37. Hickey, S. F., Sridhar, M., Westermann, A. J., Qin, Q., Vijayendra, P., Liou, G., and Hammond, M. C. Transgene regulation in plants by alternative splicing of a suicide exon. *Nucleic Acids Res.* 2012, 40(10), 4701-10.
38. Tai, T. H., Dahlbeck, D., Clark, E. T., Gajiwala, P., Pasion, R., Whalen, M. C., Stall, R. E., and Staskawicz, B. J. Expression of the Bs2 pepper gene confers resistance to bacterial spot disease in tomato. *Proc Natl Acad Sci USA.* 1999, 96(24), 14153-14158.

We claim:

1. A vector comprising a transgene,
    wherein the transgene comprises an isolated DNA encoding a plant 5S rRNA mimic (P5SM), operably linked to a regulatory sequence, and comprises an Adenine nucleotide at position −2 of the 5' splice site of the P5SM, and a Guanine nucleotide at position −1 of the 5' splice site of the P5SM; and
    wherein the P5SM comprises P1, P2, P3a, P3b, and P3c pairing elements and a L3 loop derived from a first plant species; and a L2 loop derived from a second plant species,
wherein the L2 loop comprises an extended purine-rich region; and
wherein the first plant species and second plant species are angiosperms.

2. The vector of claim 1, wherein the first plant species is a monocotyledonous plant species.

3. The vector of claim 1, wherein the first plant species is selected from the group consisting of *Festuca arundinacea, Hordeum vulgare, Oryza sativa, Triticum aestivim*, and *Zea mays*.

4. The vector of claim 1, wherein the first plant species is *Oryza sativa*.

5. The vector of claim 1, wherein the second plant species is a dicotyledonous plant species.

6. The vector of claim 1, wherein the second plant species is selected from the group consisting of *Arabidopsis thaliana, Brassica oleracea, Brassica napus, Glycine max, Lycopersicon esculentum, Mesembryanthemum crystallinum, Medicago trunculata, Phaseolus vulgaris*, and *Solanum tuberosum*.

7. The vector of claim 1, wherein the L2 loop comprises the extended purine-rich sequence from *Arabidopsis thaliana*.

8. The vector of claim 1, wherein the extended purine-rich region comprises at least four purine nucleotides.

9. The vector of claim 1, wherein the extended purine-rich region comprises at least five purine nucleotides.

10. The vector of claim 1, wherein the L2 loop comprises nucleotides 217 to 221 of SEQ ID NO: 1 (HyP5SM).

11. The vector of claim 1, wherein the regulatory sequence is selected from the group consisting of a constitutive promoter sequence, an inducible promoter sequence, and the endogenous promoter sequence of the transgene.

12. The vector of claim 1, wherein the P5SM comprises a nucleotide sequence at least 90% identical to nucleotides 197 to 320 of SEQ ID NO: 1 (HyP5SM).

13. The vector of claim 1, wherein the P5SM comprises nucleotides 197 to 320 of SEQ ID NO: 1 (HyP5SM).

14. The vector of claim 1, wherein the isolated DNA comprises a nucleotide aptamer that binds a chemical inducer.

15. The vector of claim 14, wherein binding of the chemical inducer to the nucleotide aptamer induces excision of the P5SM from a gene transcript when the P5SM is incorporated into a gene in a host organism.

16. The vector of claim 14, wherein binding of the chemical inducer to the nucleotide aptamer inhibits excision of the P5SM from a gene transcript when the P5SM is incorporated into a gene in a host organism.

17. A host cell comprising the vector of claim 1.

18. The host cell of claim 17, wherein the P5SM inhibits transgene protein expression.

19. The host cell of claim 18, further comprising a second vector, wherein the second vector comprises an inducible promoter sequence and a recombinant nucleotide encoding an L5 ribosomal protein.

20. The host cell of claim 19, wherein the L5 ribosomal protein is derived from the first plant species.

21. The host cell of claim 19, wherein the L5 ribosomal protein induces excision of the P5SM.

22. A transgenic plant comprising the vector of claim 1.

23. The transgenic plant of claim 22, further comprising a second vector, wherein the second vector comprises an inducible promoter sequence and a recombinant nucleotide encoding an L5 ribosomal protein.

24. Seed comprising the vector of claim 1.

25. The seed of claim 24, further comprising a second vector, wherein the second vector comprises an inducible promoter sequence and a recombinant nucleotide encoding an L5 ribosomal protein.

26. A method of regulating transgene expression in a plant, comprising:
    (a) providing a plant comprising a first vector and a second vector, wherein the first vector is the vector of claim 1, and the second vector comprises an inducible promoter sequence and a recombinant polynucleotide encoding an L5 ribosomal protein;
    (b) growing the plant under conditions whereby the first vector is expressed to produce mRNA comprising the P5SM; and
    (c) inducing the expression of the L5 ribosomal protein in the plant, wherein the L5 ribosomal protein induces excision of the P5SM from the mRNA, thereby allowing expression of the protein encoded by the transgene in the first vector.

* * * * *

SEQUENCE LISTING

<160> NUMBER OF SEQ ID NOS: 161

<210> SEQ ID NO 1
<211> LENGTH: 428
<212> TYPE: DNA
<213> ORGANISM: Artificial Sequence
<220> FEATURE:
<223> OTHER INFORMATION: HyP5SM

<400> SEQUENCE: 1

```
gtagatttat gcatcctctt gtcatgagaa gtcgaattgt tcccattctg tgtgttgcag      60
ctacagatgg agatacatag agatactcgt ggattttgct tagtgttgag ttttgttctg     120
gttgtgaact aaaagtttat acatttgcag gaaataaata gccttttgtt taaatcaaaa     180
ggtcttacct atgttagtgt gaagcattgg atcccaaaga gagaactcca aaatgcgatg     240
aggcatattt aatcttgtct ggactagtaa caggttggga tgaccacctg tgaagctcca     300
acaggattgc ctcctcacgc aatgtttgag gtctgatgtt caatagcttg ttttgtttca     360
ctttgctttg gactttcttt tcgccaatga gctatgtttc tgatggtttt cactcttttg     420
gtgtgtag                                                              428
```

<210> SEQ ID NO 2
<211> LENGTH: 127
<212> TYPE: RNA
<213> ORGANISM: Arabidopsis thaliana

<400> SEQUENCE: 2

```
uauugcguga ggcauuggau cccaaagaga gaacuccaaa augcgaggcu acauguuaug      60
gacuaguauc agguugggag accuccugag aagcuccagc aaguaagccu cgaucacgca     120
aaauguu                                                               127
```

<210> SEQ ID NO 3
<211> LENGTH: 132
<212> TYPE: RNA
<213> ORGANISM: Oryza sativa

<400> SEQUENCE: 3

```
aacuguguga agcauuggau cccaaagaac uccaaaaugc gaugaggcau auuuaaucuu      60
gucuggacua guaacagguu gggaugacca ccugugaagc uccaacagga uugccuccuc     120
```
acgcucuuuc ag                                                           132

<210> SEQ ID NO 4
<211> LENGTH: 125
<212> TYPE: RNA
<213> ORGANISM: Oryza sativa

<400> SEQUENCE: 4
ggauguguga agcauuggau cccagagaac uccaaaaugc gagaaggccu ugaguggacu        60
aguaccagga uggggagacc cuucugggaa gcuccuucaa gaaugccucu uucacgcucu       120
ucuuc                                                                   125

<210> SEQ ID NO 5
<211> LENGTH: 125
<212> TYPE: RNA
<213> ORGANISM: Oryza sativa

<400> SEQUENCE: 5
gacugcguga agcauuggau cccaaagaac uccaaaaugc gugaaggcuu ugaauggacu        60
aguaucagga uggggagacu cuccugagaa gcuccaucaa gaaugccucg uucacacacu       120
uuuuc                                                                   125

<210> SEQ ID NO 6
<211> LENGTH: 137
<212> TYPE: RNA
<213> ORGANISM: Glycine max

<400> SEQUENCE: 6
aauaguguga agcauuggau cccagagaaa gaucuccaaa augcgcgagg cagcauauau        60
ggacuugaug gauuaguauc agguagggug accuccugug aagcuccauc aaggaugccu       120
cggucacgcu cuguuca                                                      137

<210> SEQ ID NO 7
<211> LENGTH: 137
<212> TYPE: RNA
<213> ORGANISM: Phaseolus vulgaris

<400> SEQUENCE: 7
aauuguguga agcauuggau cccagacaaa gaacuccaaa augcacgagg cagcgaguuu        60
agacuugaug gaucaguauc agguagggag accuccugug aagcuccauc aaggaugccu       120
cagucacgcu cuugaa                                                       137

<210> SEQ ID NO 8
<211> LENGTH: 140
<212> TYPE: RNA
<213> ORGANISM: Medicago truncatula

<400> SEQUENCE: 8
uauaguguga aagcauugga ucccagacaa agaacuccaa uaugcgcgag gcauuacgcu        60
uggccuuggu ggauuaguau cagguuggga gaccuccuga gaagcuucau caaggauaug       120
ccucggucac gcucaauuca                                                   140

<210> SEQ ID NO 9
<211> LENGTH: 141
<212> TYPE: RNA
<213> ORGANISM: Cucumis melo

<400> SEQUENCE: 9

```
cucagcguga agcauuggau cccacauuaa gaacuccaaa augcaugagg cuggauuuug      60
ucguugcuug acuggaucag uaucagguug ggagaccacc ugagaagcuc caucaagugg    120
gccucgguca cgcuacagua g                                              141
```

<210> SEQ ID NO 10
<211> LENGTH: 136
<212> TYPE: RNA
<213> ORGANISM: Populus tremula

<400> SEQUENCE: 10

```
uaaugcguga gcauuggauc ccacacagag aacuccaaaa ugcgagaggc uuccauuuug     60
gcuugaaugg acuaguauca gacugggaga ccuccugaga agcuccauca agugagccuc   120
gaucacgcac cuguug                                                   136
```

<210> SEQ ID NO 11
<211> LENGTH: 136
<212> TYPE: RNA
<213> ORGANISM: Populus trichocarpa

<400> SEQUENCE: 11

```
uaaugcguga gcauuggauc ccacacagug aacuccaaaa ugcaagaggc uuccauuuug     60
gcuugaaugg acuaguauca ggcugggaga ccuccugaga agcuccauca agugagccuc   120
gaucacgcac cuguug                                                   136
```

<210> SEQ ID NO 12
<211> LENGTH: 123
<212> TYPE: RNA
<213> ORGANISM: Zinnia violacea

<400> SEQUENCE: 12

```
uuuugcguga agcauuggau cccaacagag aacuccaaaa ugcgagaccu ugauuggauu     60
aguaucaggc agggugaccu ccugagaagc uccgucaagu acacucaau cacgccuucg    120 aag                                                                 123
```

<210> SEQ ID NO 13
<211> LENGTH: 123
<212> TYPE: RNA
<213> ORGANISM: Helianthus argophyllus

<400> SEQUENCE: 13

```
uguugcguga ggcauuggau cccaacagag aacuccaaaa ugcgagaccu ugauuggauu     60
aguaucaggc aggggaccu ccugagaagc uccaucaagu gagacucaau cacgcuuuca    120
aag                                                                 123
```

<210> SEQ ID NO 14
<211> LENGTH: 124
<212> TYPE: RNA
<213> ORGANISM: Carthamus tinctorius

<400> SEQUENCE: 14

```
aauggcguga ggcauuggau cccacacaga gaacuccaaa augcgagacc uugauuggau     60
uaguaucagg uagggcgacc uccugagaag cuccaucaag ugagucccaa ucacgcgcug   120
aagu                                                                124
```

<210> SEQ ID NO 15

-continued

```
<211> LENGTH: 128
<212> TYPE: RNA
<213> ORGANISM: Brassica oleracea

<400> SEQUENCE: 15
uauugcguga ggcauuggau cccaaaagag agaacuccaa aaugcgaggc uacauguuau    60
ggacuaguau cagguaggga gaccuccuga gaagcuccag caaguaagcc uccaucacgc   120
ugaagaga                                                            128

<210> SEQ ID NO 16
<211> LENGTH: 128
<212> TYPE: RNA
<213> ORGANISM: Brassica napus

<400> SEQUENCE: 16
uauugcguga ggcauuggau cccaaaagag agaacuccaa aaugcgaggc uacauguuau    60
ggacuaguau cagguaggga gaccuccuga gaagcuccag caaguaagcc uccaucacgc   120
ugaagaga                                                            128

<210> SEQ ID NO 17
<211> LENGTH: 123
<212> TYPE: RNA
<213> ORGANISM: Lactuca serriola

<400> SEQUENCE: 17
guuuguguga aagcauugga ucccaugaag aacuccaaaa ugcgagaccu ugauuggaau    60
aguaucaggu ugggcgaccu ccugagaagc uccaucaagc gacccucaau cacgccacca   120
aua                                                                 123

<210> SEQ ID NO 18
<211> LENGTH: 122
<212> TYPE: RNA
<213> ORGANISM: Cichorium intybus

<400> SEQUENCE: 18
guugugugaa agcauuggau cccaagaaga acuccaaaau gcgagaccuu gauuggauua    60
guaucaggua gggcgaccuc cugagaagcu ccaucaagug acccucaauc acgccuucaa   120
ug                                                                  122

<210> SEQ ID NO 19
<211> LENGTH: 123
<212> TYPE: RNA
<213> ORGANISM: Centaurea maculosa

<400> SEQUENCE: 19
aaugcgugag gcauuggauc ccacacagag aacuccaaaa ugcgagaccu ugauuggauu    60
aguaucaggc agggcgaccu ccugagaagc uccgucaagu gagucccaau cacgcgcuga   120
agu                                                                 123

<210> SEQ ID NO 20
<211> LENGTH: 125
<212> TYPE: RNA
<213> ORGANISM: Liriodendron tulipifera

<400> SEQUENCE: 20
auuagcguga agcauuggau cccaucuaaa gaacuccaaa augcgaaggu cuugaaugga    60
cuaguaucag ggugggggac cuccugugaa gcuccuucaa gcuagccuca gucacgcacc   120
```

-continued

```
guguu                                                              125

<210> SEQ ID NO 21
<211> LENGTH: 123
<212> TYPE: RNA
<213> ORGANISM: Senecio cambrensis

<400> SEQUENCE: 21
uguugcguga agcauuggau cccaacaaug aacuccaaaa ugugagaccu ugauuggauu    60
aguaucaggu agggagaccu ccugagaagu ccgucaagu gacccucagu cacgcgcuaa   120
aaa                                                                123

<210> SEQ ID NO 22
<211> LENGTH: 137
<212> TYPE: RNA
<213> ORGANISM: Solanum lycopersicum

<400> SEQUENCE: 22
gaagguguga cgcauuggau cccaaauaaa gaacuccaaa augcaagagg cagguauauu    60
uccuugacug gauuaguauc aggaaggggg accuccugag aagcuccauc aagugagccu   120
caaucacgcc uuauaau                                                 137

<210> SEQ ID NO 23
<211> LENGTH: 137
<212> TYPE: RNA
<213> ORGANISM: Solanum tuberosum

<400> SEQUENCE: 23
gaagguguga cgcauuggau cccaaauaaa gaacuccaaa augcaagagg cagguauauu    60
uccuugacug gauuaguauc aggaaggggg accuccugag aagcuccauc aagugagccu   120
caaucacgcc uuauaau                                                 137

<210> SEQ ID NO 24
<211> LENGTH: 136
<212> TYPE: RNA
<213> ORGANISM: Nicotiana benthamiana

<400> SEQUENCE: 24
gaagguggaa gcauuggauc ccauauaaag aacuccaaaa ugcaagaggc agguauuuu    60 ccucgacugg aucaguauca ggaaggggga ccuccugaga agcuccauca agugagccuc   120
aaucacgccu uaucau                                                  136

<210> SEQ ID NO 25
<211> LENGTH: 138
<212> TYPE: RNA
<213> ORGANISM: Nicotiana tabacum

<400> SEQUENCE: 25
gaagguguga agcauuggau cccacauaaa gaacuccaaa augcaagagg cagguaucuu    60
uuccuugacu ggaucaguau caggaagggg gaccuccuga gaagcuccau caagugagcc   120
ucaaucacgc cuuauaau                                                138

<210> SEQ ID NO 26
<211> LENGTH: 139
<212> TYPE: RNA
<213> ORGANISM: Mesembryanthemum crystallinum
```

```
<400> SEQUENCE: 26
aagugugugu agcauuggau cccaaagauc gaacuccaaa augcgaagag gcuuuguuua      60
uaucuugacu ggacuaguau caggaugggg gaccuccuga gaagcuccgu caaguaaagc     120
cucugacacg cacuaauuu                                                  139

<210> SEQ ID NO 27
<211> LENGTH: 137
<212> TYPE: RNA
<213> ORGANISM: Hordeum vulgare

<400> SEQUENCE: 27
aacagcguga agcauuggau cccauuacag aacuccaaaa ugcauggagg cacauuuuaa      60
ucuugguugg acuaguaaca gguugggaug accuccugug aagcuccaac aagauugccu     120
ccuucacgcu uauugaa                                                    137

<210> SEQ ID NO 28
<211> LENGTH: 136
<212> TYPE: RNA
<213> ORGANISM: Aquilegia formos

<400> SEQUENCE: 28
gaaggcguga agcauuggau cccauguaca gaacuccaaa augcgaaaag uggcauuauu      60
agcuugaaug gacuaguaac agguuggggg accuccugug aagcuccaca agugagccuc     120
acucacgcaa aguacu                                                     136

<210> SEQ ID NO 29
<211> LENGTH: 123
<212> TYPE: RNA
<213> ORGANISM: Senecio cambrensis

<400> SEQUENCE: 29
uguugcguga agcauuggau ccccauagag aacuccaaua ugcgagagcu ugauuggauu      60
aguaucaggc ugggagaccu ccgagaagu ucuaucaagu caucccacu cacgcguuga      120 agu                                                                   123

<210> SEQ ID NO 30
<211> LENGTH: 126
<212> TYPE: RNA
<213> ORGANISM: Euphorbia esula

<400> SEQUENCE: 30
aauggcguga agcauuggau cccacuaaac gaacuccaaa augcgaggac uugaauggac      60
uaguaucagg uugggagacc uccugagaag cuccaucaag cuagugccuc auucacgcac     120
ugguau                                                                126

<210> SEQ ID NO 31
<211> LENGTH: 134
<212> TYPE: RNA
<213> ORGANISM: Zea mays

<400> SEQUENCE: 31
gaaugcguga agcauuggau cccaaagaac uccaaaaugc gauaagguau uuuuauucu       60 ugccugaacu aguaacaggu ugggaugacc uccugugaag cuucaacaag auugccucag     120
ucacgcucac ugag                                                       134
```

```
<210> SEQ ID NO 32
<211> LENGTH: 126
<212> TYPE: RNA
<213> ORGANISM: Zea mays

<400> SEQUENCE: 32
agauguguga agcauuggau cucaaagaac uccaaaaugc gagaaggccu ugaauggacu    60
aguaccagga uggggagacc cuccugagaa gcuccaucaa gaguuccuuc auucacgcua   120
uucuuc                                                              126

<210> SEQ ID NO 33
<211> LENGTH: 125
<212> TYPE: RNA
<213> ORGANISM: Zea mays

<400> SEQUENCE: 33
gaaugcguga agcauuggau cccaaagaac uccaaaaugc gauaaggccu ugaauggacu    60
aguaucagga uugggagacc auccugagaa gcuccaucaa gcaugccuug uucacgcguu   120
ucuua                                                               125

<210> SEQ ID NO 34
<211> LENGTH: 125
<212> TYPE: RNA
<213> ORGANISM: Festuca arundinacea

<400> SEQUENCE: 34
gaaugcguga agcauuggau cccaaagaac uccaaaaugc cagaaggccu ugaguggacu    60
aguaucagga aggggagacc cuccugagaa gcuccaucaa gaaugccuug gucacacgcu   120
ucuuc                                                               125

<210> SEQ ID NO 35
<211> LENGTH: 137
<212> TYPE: RNA
<213> ORGANISM: Triticum aestivum

<400> SEQUENCE: 35
aacagcguga agcauuggau cccauuacag aacuccaaaa ugcauggagg cacauuuuaa    60
ucuugguugg acuaguaaca gguugggaug accuccugug aagcuccaac aagauugccu   120
ccuucacgcu uacucag                                                  137

<210> SEQ ID NO 36
<211> LENGTH: 124
<212> TYPE: RNA
<213> ORGANISM: Triticum aestivum

<400> SEQUENCE: 36
gaauguguga agcauuggau cccaagaacu ccaaaaugcc agaaggccuu gaauggacca    60
guaucaggaa ggggagaccc uccugagaag cuccaucaag aaugcccaau ucacgcgcuu   120
ccuc                                                                124

<210> SEQ ID NO 37
<211> LENGTH: 124
<212> TYPE: RNA
<213> ORGANISM: Triticum aestivum

<400> SEQUENCE: 37
aauuguguga agcauuggau cccaaagaac uccaaaaugc gagagggccc ugaauggacu    60
```

```
aguaccagga ugggagacc cuccugggaa gcuccuucag gaagccucuu ucacgcccuu    120
cuuc                                                                124

<210> SEQ ID NO 38
<211> LENGTH: 131
<212> TYPE: RNA
<213> ORGANISM: Malus domestica

<400> SEQUENCE: 38
gauagcguga cgcauuggau cccacacaaa gcacuccaaa augcgagagg uuuuugacuu    60
gaauggacca guaucaggug ggagaccucc ugugaagcuc caucaagcga gccucaguca   120
cguaccuuuc a                                                        131

<210> SEQ ID NO 39
<211> LENGTH: 136
<212> TYPE: RNA
<213> ORGANISM: Vitis vinifera

<400> SEQUENCE: 39
uauaguguga agcauuggau cccacagaaa gaacuccaaa augcgcgagg cugcauuuuc    60
uaccuugaau ggacuaguau caggcggggg accuccugag aagcuccauc aagcggccuc   120
aaucacgcac uacuug                                                   136

<210> SEQ ID NO 40
<211> LENGTH: 117
<212> TYPE: RNA
<213> ORGANISM: Physcomitrella patens

<400> SEQUENCE: 40
gcagcgaaau ccaaaggccu accagauccc auccgaacuc ugaagucaag gugccuuugg    60
ccggauuagu ucgggagguu cgcacccucu uggaacuucc ggugcugcuu uauuauu      117

<210> SEQ ID NO 41
<211> LENGTH: 52
<212> TYPE: DNA
<213> ORGANISM: Artificial Sequence
<220> FEATURE:
<223> OTHER INFORMATION: Primer

<400> SEQUENCE: 41
atggttttca ctcttttggt gtgtagagat atgggctgaa tacaaatcac ag            52

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
ttttggagtt ctctctttgg gatccaa                                       27

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
tttcatgtat tcgagggtgt tgat                                          24
```

<210> SEQ ID NO 44
<211> LENGTH: 43
<212> TYPE: DNA
<213> ORGANISM: Artificial Sequence
<220> FEATURE:
<223> OTHER INFORMATION: Primer

<400> SEQUENCE: 44
tttcactctt ttggtgtgta gagttctttt acttgctatg tgg                43

<210> SEQ ID NO 45
<211> LENGTH: 43
<212> TYPE: DNA
<213> ORGANISM: Artificial Sequence
<220> FEATURE:
<223> OTHER INFORMATION: Primer

<400> SEQUENCE: 45
tttcactctt ttggtgtgta gagctctttt acttgctatg tgg                43

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
ttgagttcca tcccaagaat tga                                       23

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
ttgagcaatt ctctctcatt ataaatg                                   27

<210> SEQ ID NO 48
<211> LENGTH: 54
<212> TYPE: DNA
<213> ORGANISM: Artificial Sequence
<220> FEATURE:
<223> OTHER INFORMATION: Primer

<400> SEQUENCE: 48
tgggatccaa tgcttcacac taacataggt aagacctttt gatttaaaca aaag     54

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49
tgcctgatgc aatcagaaac atggt                                     25

<210> SEQ ID NO 50
<211> LENGTH: 20
<212> TYPE: DNA
<213> ORGANISM: Artificial Sequence
<220> FEATURE:

<223> OTHER INFORMATION: Primer

<400> SEQUENCE: 50
tgcaacccct ttttggaaac                                           20

<210> SEQ ID NO 51
<211> LENGTH: 37
<212> TYPE: DNA
<213> ORGANISM: Artificial Sequence
<220> FEATURE:
<223> OTHER INFORMATION: Primer

<400> SEQUENCE: 51
tgattgatca atgtcttctt ctgtagcagt gttatgg                        37

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
tgattgatca atgtcttctt ctgtagcagt gttatgg                        37

<210> SEQ ID NO 53
<211> LENGTH: 32
<212> TYPE: DNA
<213> ORGANISM: Artificial Sequence
<220> FEATURE:
<223> OTHER INFORMATION: Primer

<400> SEQUENCE: 53
tgattgatca atggatttct ccggtttgtt tc                             32

<210> SEQ ID NO 54
<211> LENGTH: 32
<212> TYPE: DNA
<213> ORGANISM: Artificial Sequence
<220> FEATURE:
<223> OTHER INFORMATION: Primer

<400> SEQUENCE: 54
tgattgatca atggatttct ccggtttgtt tc                             32

<210> SEQ ID NO 55
<211> LENGTH: 32
<212> TYPE: DNA
<213> ORGANISM: Artificial Sequence
<220> FEATURE:
<223> OTHER INFORMATION: Primer

<400> SEQUENCE: 55
tgattgatca atggatttct ccggtttgtt tc                             32

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
tgatagatct atggcttctt tcacggcaac                                30

```
<210> SEQ ID NO 57
<211> LENGTH: 33
<212> TYPE: DNA
<213> ORGANISM: Artificial Sequence
<220> FEATURE:
<223> OTHER INFORMATION: Primer

<400> SEQUENCE: 57
tgatagatct atgcaaatct catcttcatc gtc                          33

<210> SEQ ID NO 58
<211> LENGTH: 43
<212> TYPE: DNA
<213> ORGANISM: Artificial Sequence
<220> FEATURE:
<223> OTHER INFORMATION: Primer

<400> SEQUENCE: 58
tatgcagagt cattcgctcc aggtagattt atgcatcctc ttg               43

<210> SEQ ID NO 59
<211> LENGTH: 43
<212> TYPE: DNA
<213> ORGANISM: Artificial Sequence
<220> FEATURE:
<223> OTHER INFORMATION: Primer

<400> SEQUENCE: 59
tatgcagagt cattcgctca aggtagattt atgcatcctc ttg               43

<210> SEQ ID NO 60
<211> LENGTH: 45
<212> TYPE: DNA
<213> ORGANISM: Artificial Sequence
<220> FEATURE:
<223> OTHER INFORMATION: Primer

<400> SEQUENCE: 60
gttttcactc ttttggtgtg taggtatctt ttacttgcta tgtgg             45

<210> SEQ ID NO 61
<211> LENGTH: 45
<212> TYPE: DNA
<213> ORGANISM: Artificial Sequence
<220> FEATURE:
<223> OTHER INFORMATION: Primer

<400> SEQUENCE: 61
gttttcactc ttttggtgtg tagctatctt ttacttgcta tgtgg             45

<210> SEQ ID NO 62
<211> LENGTH: 45
<212> TYPE: DNA
<213> ORGANISM: Artificial Sequence
<220> FEATURE:
<223> OTHER INFORMATION: Primer

<400> SEQUENCE: 62
gttttcactc ttttggtgtg tagccatctt ttacttgcta tgtgg             45

<210> SEQ ID NO 63
<211> LENGTH: 20
<212> TYPE: DNA
<213> ORGANISM: Artificial Sequence
<220> FEATURE:
<223> OTHER INFORMATION: Primer
```

```
<400> SEQUENCE: 63
gtgtgaagca ttggatccca                                              20

<210> SEQ ID NO 64
<211> LENGTH: 28
<212> TYPE: DNA
<213> ORGANISM: Artificial Sequence
<220> FEATURE:
<223> OTHER INFORMATION: Primer

<400> SEQUENCE: 64
gtagatttat gcatcctctt gtcatgag                                     28

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gtagatgaga tgtgacgaac gt                                           22

<210> SEQ ID NO 66
<211> LENGTH: 26
<212> TYPE: DNA
<213> ORGANISM: Artificial Sequence
<220> FEATURE:
<223> OTHER INFORMATION: Primer

<400> SEQUENCE: 66
ggctatttat ttccttcata gcttct                                       26

<210> SEQ ID NO 67
<211> LENGTH: 28
<212> TYPE: DNA
<213> ORGANISM: Artificial Sequence
<220> FEATURE:
<223> OTHER INFORMATION: Primer

<400> SEQUENCE: 67
ggctatttat ttcctcatta taaatgtc                                     28

<210> SEQ ID NO 68
<211> LENGTH: 26
<212> TYPE: DNA
<213> ORGANISM: Artificial Sequence
<220> FEATURE:
<223> OTHER INFORMATION: Primer

<400> SEQUENCE: 68
ggcattggat cccaaagaga gaactc                                       26

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
gcgtgaggag gcaatcctg                                               19

<210> SEQ ID NO 70
<211> LENGTH: 20
```

<212> TYPE: DNA
<213> ORGANISM: Artificial Sequence
<220> FEATURE:
<223> OTHER INFORMATION: Primer

<400> SEQUENCE: 70
gatgatctcg agccctgaag                                                    20

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
gaggtagatg agatgtgacg a                                                  21

<210> SEQ ID NO 72
<211> LENGTH: 32
<212> TYPE: DNA
<213> ORGANISM: Artificial Sequence
<220> FEATURE:
<223> OTHER INFORMATION: Primer

<400> SEQUENCE: 72
gacgtcgact tacttgtaca gctcgtccat gc                                      32

<210> SEQ ID NO 73
<211> LENGTH: 32
<212> TYPE: DNA
<213> ORGANISM: Artificial Sequence
<220> FEATURE:
<223> OTHER INFORMATION: Primer

<400> SEQUENCE: 73
gacgtcgact tacttgtaca gctcgtccat gc                                      32

<210> SEQ ID NO 74
<211> LENGTH: 32
<212> TYPE: DNA
<213> ORGANISM: Artificial Sequence
<220> FEATURE:
<223> OTHER INFORMATION: Primer

<400> SEQUENCE: 74
gacgtcgact tacttgtaca gctcgtccat gc                                      32

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
gacatcactt acgctgagta ct                                                 22

<210> SEQ ID NO 76
<211> LENGTH: 22
<212> TYPE: DNA
<213> ORGANISM: Artificial Sequence
<220> FEATURE:
<223> OTHER INFORMATION: Primer

<400> SEQUENCE: 76

-continued gacatcactt acgctgagta ct                                      22

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
gacatcactt acgctgagta ct                                      22

<210> SEQ ID NO 78
<211> LENGTH: 31
<212> TYPE: DNA
<213> ORGANISM: Artificial Sequence
<220> FEATURE:
<223> OTHER INFORMATION: Primer

<400> SEQUENCE: 78
gacagatcta tgtctagagt gagcaagggc g                            31

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
gacagatcta tgtctagagt gagcaagggc g                            31

<210> SEQ ID NO 80
<211> LENGTH: 31
<212> TYPE: DNA
<213> ORGANISM: Artificial Sequence
<220> FEATURE:
<223> OTHER INFORMATION: Primer

<400> SEQUENCE: 80
gacagatcta tgtctagagt gagcaagggc g                            31

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
cttggagccg tactggaact g                                       21

<210> SEQ ID NO 82
<211> LENGTH: 25
<212> TYPE: DNA
<213> ORGANISM: Artificial Sequence
<220> FEATURE:
<223> OTHER INFORMATION: Primer

<400> SEQUENCE: 82
cttgatgtga agaaaccaca agatg                                   25

<210> SEQ ID NO 83
<211> LENGTH: 26
<212> TYPE: DNA
<213> ORGANISM: Artificial Sequence

```
<220> FEATURE:
<223> OTHER INFORMATION: Primer

<400> SEQUENCE: 83
cttgaagaag atggttctct caaaca                                          26

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
ctgcttgtcg gccatgatat ag                                              22

<210> SEQ ID NO 85
<211> LENGTH: 52
<212> TYPE: DNA
<213> ORGANISM: Artificial Sequence
<220> FEATURE:
<223> OTHER INFORMATION: Primer

<400> SEQUENCE: 85
ctcatgacaa gaggatgcat aaatctacct ctttgcttgg aggataagtt gg             52

<210> SEQ ID NO 86
<211> LENGTH: 49
<212> TYPE: DNA
<213> ORGANISM: Artificial Sequence
<220> FEATURE:
<223> OTHER INFORMATION: Primer

<400> SEQUENCE: 86
ctcatgacaa gaggatgcat aaatctacgc accaaacgta gattgccca                 49

<210> SEQ ID NO 87
<211> LENGTH: 60
<212> TYPE: DNA
<213> ORGANISM: Artificial Sequence
<220> FEATURE:
<223> OTHER INFORMATION: Primer

<400> SEQUENCE: 87
ctcatgacaa gaggatgcat aaatctacct ttagatcttc tcggtaataa acttcgtctt     60

<210> SEQ ID NO 88
<211> LENGTH: 49
<212> TYPE: DNA
<213> ORGANISM: Artificial Sequence
<220> FEATURE:
<223> OTHER INFORMATION: Primer

<400> SEQUENCE: 88
ctcatgacaa gaggatgcat aaatctacct tcatagcttc tgccaaccg                 49

<210> SEQ ID NO 89
<211> LENGTH: 50
<212> TYPE: DNA
<213> ORGANISM: Artificial Sequence
<220> FEATURE:
<223> OTHER INFORMATION: Primer

<400> SEQUENCE: 89
ctcatgacaa gaggatgcat aaatctacct ctttactggc cggaaaagtc                50
```

<210> SEQ ID NO 90
<211> LENGTH: 51
<212> TYPE: DNA
<213> ORGANISM: Artificial Sequence
<220> FEATURE:
<223> OTHER INFORMATION: Primer

<400> SEQUENCE: 90
ctcatgacaa gaggatgcat aaatctacct cgggtgtcat aagcaaagtt c         51

<210> SEQ ID NO 91
<211> LENGTH: 48
<212> TYPE: DNA
<213> ORGANISM: Artificial Sequence
<220> FEATURE:
<223> OTHER INFORMATION: Primer

<400> SEQUENCE: 91
ctcatgacaa gaggatgcat aaatctacct cctggacgta gccttcgg              48

<210> SEQ ID NO 92
<211> LENGTH: 52
<212> TYPE: DNA
<213> ORGANISM: Artificial Sequence
<220> FEATURE:
<223> OTHER INFORMATION: Primer

<400> SEQUENCE: 92
ctcatgacaa gaggatgcat aaatctacct cctgaacaaa ccggttagtc tg         52

<210> SEQ ID NO 93
<211> LENGTH: 51
<212> TYPE: DNA
<213> ORGANISM: Artificial Sequence
<220> FEATURE:
<223> OTHER INFORMATION: Primer

<400> SEQUENCE: 93
ctcatgacaa gaggatgcat aaatctacct cattataaat gtcgttcgcg g          51

<210> SEQ ID NO 94
<211> LENGTH: 58
<212> TYPE: DNA
<213> ORGANISM: Artificial Sequence
<220> FEATURE:
<223> OTHER INFORMATION: Primer

<400> SEQUENCE: 94
ctcatgacaa gaggatgcat aaatctacct caatgtgagg gaccatgttt ctgattgc   58

<210> SEQ ID NO 95
<211> LENGTH: 26
<212> TYPE: DNA
<213> ORGANISM: Artificial Sequence
<220> FEATURE:
<223> OTHER INFORMATION: Primer

<400> SEQUENCE: 95
ctacacacca aaagagtgaa aaccat                                      26

<210> SEQ ID NO 96
<211> LENGTH: 23
<212> TYPE: DNA
<213> ORGANISM: Artificial Sequence
<220> FEATURE:
<223> OTHER INFORMATION: Primer -continued

<400> SEQUENCE: 96
cgtccaggag gaaataaata gcc                                       23

<210> SEQ ID NO 97
<211> LENGTH: 22
<212> TYPE: DNA
<213> ORGANISM: Artificial Sequence
<220> FEATURE:
<223> OTHER INFORMATION: Primer

<400> SEQUENCE: 97
cgtccaggag agaaccatct tc                                        22

<210> SEQ ID NO 98
<211> LENGTH: 17
<212> TYPE: DNA
<213> ORGANISM: Artificial Sequence
<220> FEATURE:
<223> OTHER INFORMATION: Primer

<400> SEQUENCE: 98
cgatgccctt cagctcg                                              17

<210> SEQ ID NO 99
<211> LENGTH: 29
<212> TYPE: DNA
<213> ORGANISM: Artificial Sequence
<220> FEATURE:
<223> OTHER INFORMATION: Primer

<400> SEQUENCE: 99
cgacatttat aatgaggaaa taaatagcc                                 29

<210> SEQ ID NO 100
<211> LENGTH: 26
<212> TYPE: DNA
<213> ORGANISM: Artificial Sequence
<220> FEATURE:
<223> OTHER INFORMATION: Primer

<400> SEQUENCE: 100
cgacatttat aatgagagag aattgc                                    26

<210> SEQ ID NO 101
<211> LENGTH: 18
<212> TYPE: DNA
<213> ORGANISM: Artificial Sequence
<220> FEATURE:
<223> OTHER INFORMATION: Primer

<400> SEQUENCE: 101
ccgagaacgt catcaccg                                             18

<210> SEQ ID NO 102
<211> LENGTH: 45
<212> TYPE: DNA
<213> ORGANISM: Artificial Sequence
<220> FEATURE:
<223> OTHER INFORMATION: Primer

<400> SEQUENCE: 102
ccacatagca agtaaaagat ggctacacac caaaagagtg aaaac               45

<210> SEQ ID NO 103

```
<211> LENGTH: 45
<212> TYPE: DNA
<213> ORGANISM: Artificial Sequence
<220> FEATURE:
<223> OTHER INFORMATION: Primer

<400> SEQUENCE: 103
ccacatagca agtaaaagat agctacacac caaaagagtg aaaac            45

<210> SEQ ID NO 104
<211> LENGTH: 45
<212> TYPE: DNA
<213> ORGANISM: Artificial Sequence
<220> FEATURE:
<223> OTHER INFORMATION: Primer

<400> SEQUENCE: 104
ccacatagca agtaaaagat acctacacac caaaagagtg aaaac            45

<210> SEQ ID NO 105
<211> LENGTH: 43
<212> TYPE: DNA
<213> ORGANISM: Artificial Sequence
<220> FEATURE:
<223> OTHER INFORMATION: Primer

<400> SEQUENCE: 105
ccacatagca agtaaaagag ctctacacac caaaagagtg aaa              43

<210> SEQ ID NO 106
<211> LENGTH: 43
<212> TYPE: DNA
<213> ORGANISM: Artificial Sequence
<220> FEATURE:
<223> OTHER INFORMATION: Primer

<400> SEQUENCE: 106
ccacatagca agtaaaagaa ctctacacac caaaagagtg aaa              43

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107
catatgcaga gtcattcgct cttggtagat ttatgcatcc tcttg            45

<210> SEQ ID NO 108
<211> LENGTH: 45
<212> TYPE: DNA
<213> ORGANISM: Artificial Sequence
<220> FEATURE:
<223> OTHER INFORMATION: Primer

<400> SEQUENCE: 108
catatgcaga gtcattcgct ctgcgtagat ttatgcatcc tcttg            45

<210> SEQ ID NO 109
<211> LENGTH: 45
<212> TYPE: DNA
<213> ORGANISM: Artificial Sequence
<220> FEATURE:
<223> OTHER INFORMATION: Primer

<400> SEQUENCE: 109
```
catatgcaga gtcattcgct ctcggtagat ttatgcatcc tcttg    45

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
cataaagaaa ggcccggc    18

<210> SEQ ID NO 111
<211> LENGTH: 18
<212> TYPE: DNA
<213> ORGANISM: Artificial Sequence
<220> FEATURE:
<223> OTHER INFORMATION: Primer

<400> SEQUENCE: 111
cataaagaaa ggcccggc    18

<210> SEQ ID NO 112
<211> LENGTH: 18
<212> TYPE: DNA
<213> ORGANISM: Artificial Sequence
<220> FEATURE:
<223> OTHER INFORMATION: Primer

<400> SEQUENCE: 112
cataaagaaa ggcccggc    18

<210> SEQ ID NO 113
<211> LENGTH: 46
<212> TYPE: DNA
<213> ORGANISM: Artificial Sequence
<220> FEATURE:
<223> OTHER INFORMATION: Primer

<400> SEQUENCE: 113
caggattgcc tcctcacgca atgtttgagg tctgatgttc aatagc    46

<210> SEQ ID NO 114
<211> LENGTH: 23
<212> TYPE: DNA
<213> ORGANISM: Artificial Sequence
<220> FEATURE:
<223> OTHER INFORMATION: Primer

<400> SEQUENCE: 114
cagcccatat ctcttcatag ctt    23

<210> SEQ ID NO 115
<211> LENGTH: 18
<212> TYPE: DNA
<213> ORGANISM: Artificial Sequence
<220> FEATURE:
<223> OTHER INFORMATION: Primer

<400> SEQUENCE: 115
caccctgacc tacggcgt    18

<210> SEQ ID NO 116
<211> LENGTH: 24
<212> TYPE: DNA

```
<213> ORGANISM: Artificial Sequence
<220> FEATURE:
<223> OTHER INFORMATION: Primer

<400> SEQUENCE: 116
caattctctc tcaaacattt tgcg                                           24

<210> SEQ ID NO 117
<211> LENGTH: 45
<212> TYPE: DNA
<213> ORGANISM: Artificial Sequence
<220> FEATURE:
<223> OTHER INFORMATION: Primer

<400> SEQUENCE: 117
caagaggatg cataaatcta cgcagagcga atgactctgc atatg                    45

<210> SEQ ID NO 118
<211> LENGTH: 43
<212> TYPE: DNA
<213> ORGANISM: Artificial Sequence
<220> FEATURE:
<223> OTHER INFORMATION: Primer

<400> SEQUENCE: 118
caagaggatg cataaatcta ccttgagcga atgactctgc ata                      43

<210> SEQ ID NO 119
<211> LENGTH: 43
<212> TYPE: DNA
<213> ORGANISM: Artificial Sequence
<220> FEATURE:
<223> OTHER INFORMATION: Primer

<400> SEQUENCE: 119
caagaggatg cataaatcta cctggagcga atgactctgc ata                      43

<210> SEQ ID NO 120
<211> LENGTH: 45
<212> TYPE: DNA
<213> ORGANISM: Artificial Sequence
<220> FEATURE:
<223> OTHER INFORMATION: Primer

<400> SEQUENCE: 120
caagaggatg cataaatcta ccgagagcga atgactctgc atatg                    45

<210> SEQ ID NO 121
<211> LENGTH: 45
<212> TYPE: DNA
<213> ORGANISM: Artificial Sequence
<220> FEATURE:
<223> OTHER INFORMATION: Primer

<400> SEQUENCE: 121
caagaggatg cataaatcta ccaagagcga atgactctgc atatg                    45

<210> SEQ ID NO 122
<211> LENGTH: 25
<212> TYPE: DNA
<213> ORGANISM: Artificial Sequence
<220> FEATURE:
<223> OTHER INFORMATION: Primer

<400> SEQUENCE: 122
caaaatgttt gagagagaat tgctc                                          25
```

<210> SEQ ID NO 123
<211> LENGTH: 48
<212> TYPE: DNA
<213> ORGANISM: Artificial Sequence
<220> FEATURE:
<223> OTHER INFORMATION: Primer

<400> SEQUENCE: 123
atggttttca ctcttttggt gtgtagagaa tgattggacc agaggctc                48

<210> SEQ ID NO 124
<211> LENGTH: 59
<212> TYPE: DNA
<213> ORGANISM: Artificial Sequence
<220> FEATURE:
<223> OTHER INFORMATION: Primer

<400> SEQUENCE: 124
atggttttca ctcttttggt gtgtagagta ttgctcaaga atcactcaat tcttgggat     59

<210> SEQ ID NO 125
<211> LENGTH: 60
<212> TYPE: DNA
<213> ORGANISM: Artificial Sequence
<220> FEATURE:
<223> OTHER INFORMATION: Primer

<400> SEQUENCE: 125
atggttttca ctcttttggt gtgtagagat gctactacat tctagagaaa ggttacaatt    60

<210> SEQ ID NO 126
<211> LENGTH: 50
<212> TYPE: DNA
<213> ORGANISM: Artificial Sequence
<220> FEATURE:
<223> OTHER INFORMATION: Primer

<400> SEQUENCE: 126
atggttttca ctcttttggt gtgtagagag aattgctcaa cagtatgggc               50

<210> SEQ ID NO 127
<211> LENGTH: 45
<212> TYPE: DNA
<213> ORGANISM: Artificial Sequence
<220> FEATURE:
<223> OTHER INFORMATION: Primer

<400> SEQUENCE: 127
atggttttca ctcttttggt gtgtagagac gaaaggcgat ttggg                    45

<210> SEQ ID NO 128
<211> LENGTH: 48
<212> TYPE: DNA
<213> ORGANISM: Artificial Sequence
<220> FEATURE:
<223> OTHER INFORMATION: Primer

<400> SEQUENCE: 128
atggttttca ctcttttggt gtgtagagac aattgggtcg accggttt                 48

<210> SEQ ID NO 129
<211> LENGTH: 47
<212> TYPE: DNA
<213> ORGANISM: Artificial Sequence
<220> FEATURE:

<223> OTHER INFORMATION: Primer

<400> SEQUENCE: 129
atggttttca ctcttttggt gtgtagagaa tgcttggaaa acaagcc                47

<210> SEQ ID NO 130
<211> LENGTH: 50
<212> TYPE: DNA
<213> ORGANISM: Artificial Sequence
<220> FEATURE:
<223> OTHER INFORMATION: Primer

<400> SEQUENCE: 130
atggttttca ctcttttggt gtgtagagaa gaactgatga acttgtggat             50

<210> SEQ ID NO 131
<211> LENGTH: 50
<212> TYPE: DNA
<213> ORGANISM: Artificial Sequence
<220> FEATURE:
<223> OTHER INFORMATION: Primer

<400> SEQUENCE: 131
atggttttca ctcttttggt gtgtagagaa ccatcttctt caaggacgac             50

<210> SEQ ID NO 132
<211> LENGTH: 28
<212> TYPE: DNA
<213> ORGANISM: Artificial Sequence
<220> FEATURE:
<223> OTHER INFORMATION: Primer

<400> SEQUENCE: 132
atgcggatcc gtgcggcgtc ttgatgga                                     28

<210> SEQ ID NO 133
<211> LENGTH: 35
<212> TYPE: DNA
<213> ORGANISM: Artificial Sequence
<220> FEATURE:
<223> OTHER INFORMATION: Primer

<400> SEQUENCE: 133
atcagtcgac cttaaatcgg ggttactctt attgg                             35

<210> SEQ ID NO 134
<211> LENGTH: 31
<212> TYPE: DNA
<213> ORGANISM: Artificial Sequence
<220> FEATURE:
<223> OTHER INFORMATION: Primer

<400> SEQUENCE: 134
atcagtcgac ctatggtttt cgttccaagg c                                 31

<210> SEQ ID NO 135
<211> LENGTH: 31
<212> TYPE: DNA
<213> ORGANISM: Artificial Sequence
<220> FEATURE:
<223> OTHER INFORMATION: Primer

<400> SEQUENCE: 135
atcagtcgac ctatggtttt cgttccaagg c                                 31

<210> SEQ ID NO 136
<211> LENGTH: 31
<212> TYPE: DNA
<213> ORGANISM: Artificial Sequence
<220> FEATURE:
<223> OTHER INFORMATION: Primer

<400> SEQUENCE: 136
atcagtcgac ctatggtttt cgttccaagg c                                  31

<210> SEQ ID NO 137
<211> LENGTH: 35
<212> TYPE: DNA
<213> ORGANISM: Artificial Sequence
<220> FEATURE:
<223> OTHER INFORMATION: Primer

<400> SEQUENCE: 137
atcagtcgac cgctctcata tcgatagtct tgaac                              35

<210> SEQ ID NO 138
<211> LENGTH: 35
<212> TYPE: DNA
<213> ORGANISM: Artificial Sequence
<220> FEATURE:
<223> OTHER INFORMATION: Primer

<400> SEQUENCE: 138
atcagtcgac cgctctcata tcgatagtct tgaac                              35

<210> SEQ ID NO 139
<211> LENGTH: 31
<212> TYPE: DNA
<213> ORGANISM: Artificial Sequence
<220> FEATURE:
<223> OTHER INFORMATION: Primer

<400> SEQUENCE: 139
atcactcgag gaactcacac gacctgcttc g                                  31

<210> SEQ ID NO 140
<211> LENGTH: 43
<212> TYPE: DNA
<213> ORGANISM: Artificial Sequence
<220> FEATURE:
<223> OTHER INFORMATION: Primer

<400> SEQUENCE: 140
atatgcagag tcattcgctc gtggtagatt tatgcatcct ctt                     43

<210> SEQ ID NO 141
<211> LENGTH: 43
<212> TYPE: DNA
<213> ORGANISM: Artificial Sequence
<220> FEATURE:
<223> OTHER INFORMATION: Primer

<400> SEQUENCE: 141
atatgcagag tcattcgctc ggggtagatt tatgcatcct ctt                     43

<210> SEQ ID NO 142
<211> LENGTH: 43
<212> TYPE: DNA
<213> ORGANISM: Artificial Sequence
<220> FEATURE:
<223> OTHER INFORMATION: Primer

<400> SEQUENCE: 142
atatgcagag tcattcgctc gcggtagatt tatgcatcct ctt        43

<210> SEQ ID NO 143
<211> LENGTH: 25
<212> TYPE: DNA
<213> ORGANISM: Artificial Sequence
<220> FEATURE:
<223> OTHER INFORMATION: Primer

<400> SEQUENCE: 143
aggagatctg tgtgtgatga tgggt        25

<210> SEQ ID NO 144
<211> LENGTH: 31
<212> TYPE: DNA
<213> ORGANISM: Artificial Sequence
<220> FEATURE:
<223> OTHER INFORMATION: Primer

<400> SEQUENCE: 144
agcttctaga atccacatag caagtaaaag a        31

<210> SEQ ID NO 145
<211> LENGTH: 22
<212> TYPE: DNA
<213> ORGANISM: Artificial Sequence
<220> FEATURE:
<223> OTHER INFORMATION: Primer

<400> SEQUENCE: 145
actgcaactc cgataaataa cg        22

<210> SEQ ID NO 146
<211> LENGTH: 29
<212> TYPE: DNA
<213> ORGANISM: Artificial Sequence
<220> FEATURE:
<223> OTHER INFORMATION: Primer

<400> SEQUENCE: 146
acgtgtcgac ttacacggcg atctttccg        29

<210> SEQ ID NO 147
<211> LENGTH: 29
<212> TYPE: DNA
<213> ORGANISM: Artificial Sequence
<220> FEATURE:
<223> OTHER INFORMATION: Primer

<400> SEQUENCE: 147
acgtgtcgac ttacacggcg atctttccg        29

<210> SEQ ID NO 148
<211> LENGTH: 32
<212> TYPE: DNA
<213> ORGANISM: Artificial Sequence
<220> FEATURE:
<223> OTHER INFORMATION: Primer

<400> SEQUENCE: 148
acgtagatct atggaagacg ccaaaaacat aa        32

<210> SEQ ID NO 149
<211> LENGTH: 32

<212> TYPE: DNA
<213> ORGANISM: Artificial Sequence
<220> FEATURE:
<223> OTHER INFORMATION: Primer

<400> SEQUENCE: 149
acgtagatct atggaagacg ccaaaaacat aa                          32

<210> SEQ ID NO 150
<211> LENGTH: 24
<212> TYPE: DNA
<213> ORGANISM: Artificial Sequence
<220> FEATURE:
<223> OTHER INFORMATION: Primer

<400> SEQUENCE: 150
accctaatgt gttctttgca gcaa                                   24

<210> SEQ ID NO 151
<211> LENGTH: 24
<212> TYPE: DNA
<213> ORGANISM: Artificial Sequence
<220> FEATURE:
<223> OTHER INFORMATION: Primer

<400> SEQUENCE: 151
acactccgcc tctacacaga aaat                                   24

<210> SEQ ID NO 152
<211> LENGTH: 22
<212> TYPE: DNA
<213> ORGANISM: Artificial Sequence
<220> FEATURE:
<223> OTHER INFORMATION: Primer

<400> SEQUENCE: 152
aagcatatcg aaaggacgac ca                                     22

<210> SEQ ID NO 153
<211> LENGTH: 43
<212> TYPE: DNA
<213> ORGANISM: Artificial Sequence
<220> FEATURE:
<223> OTHER INFORMATION: Primer

<400> SEQUENCE: 153
aagaggatgc ataaatctac cgcgagcgaa tgactctgca tat              43

<210> SEQ ID NO 154
<211> LENGTH: 43
<212> TYPE: DNA
<213> ORGANISM: Artificial Sequence
<220> FEATURE:
<223> OTHER INFORMATION: Primer

<400> SEQUENCE: 154
aagaggatgc ataaatctac cccgagcgaa tgactctgca tat              43

```
<210> SEQ ID NO 155
<211> LENGTH: 43
<212> TYPE: DNA
<213> ORGANISM: Artificial Sequence
<220> FEATURE:
<223> OTHER INFORMATION: Primer

<400> SEQUENCE: 155
aagaggatgc ataaatctac cacgagcgaa tgactctgca tat              43

<210> SEQ ID NO 156
<211> LENGTH: 22
<212> TYPE: DNA
<213> ORGANISM: Artificial Sequence
<220> FEATURE:
<223> OTHER INFORMATION: Primer

<400> SEQUENCE: 156
aacttcccga ttccatcaaa gg                                      22

<210> SEQ ID NO 157
<211> LENGTH: 25
<212> TYPE: DNA
<213> ORGANISM: Artificial Sequence
<220> FEATURE:
<223> OTHER INFORMATION: Primer

<400> SEQUENCE: 157
aacctttctc tagaatgtag tagca                                   25

<210> SEQ ID NO 158
<211> LENGTH: 22
<212> TYPE: DNA
<213> ORGANISM: Artificial Sequence
<220> FEATURE:
<223> OTHER INFORMATION: Primer

<400> SEQUENCE: 158
aaatagacca aaccggcgtt ag                                      22

<210> SEQ ID NO 159
<211> LENGTH: 45
<212> TYPE: RNA
<213> ORGANISM: Artificial Sequence
<220> FEATURE:
<223> OTHER INFORMATION: Splicing Cassette

<400> SEQUENCE: 159
auuugccuca uaccagccga aaaggcccuu ggcaggagga aauaa             45

<210> SEQ ID NO 160
<211> LENGTH: 75
<212> TYPE: RNA
<213> ORGANISM: Artificial Sequence
<220> FEATURE:
<223> OTHER INFORMATION: Splicing Cassette

<400> SEQUENCE: 160
auguuugagg uccuaaaaca uaccagauga aaagucugga gaggugaaga auacgaccac   60
cuaggaccuc aacug                                              75

<210> SEQ ID NO 161
<211> LENGTH: 124
<212> TYPE: RNA
<213> ORGANISM: Artificial Sequence
<220> FEATURE:
```

```
<223> OTHER INFORMATION: HyP5SM

<400> SEQUENCE: 161
gugugaagca uuggauccca aagagagaac uccaaaaugc gaugaggcau auuuaaucuu        60
gucuggacua guaacagguu gggaugacca ccugugaagc uccaacagga uugccuccuc       120
acgc                                                                   124
```